(12) United States Patent
Donovan et al.

(10) Patent No.: US 11,123,103 B2
(45) Date of Patent: Sep. 21, 2021

(54) INTRODUCER SYSTEMS FOR BONE ACCESS

(71) Applicant: Relievant Medsystems, Inc., Minneapolis, MN (US)

(72) Inventors: Brian W. Donovan, Minneapolis, MN (US); Alexander Pruitt, San Jose, CA (US); Michael Willink, Sunnyvale, CA (US)

(73) Assignee: Relievant Medsystems, Inc., Minneapolis, MN (US)

( * ) Notice: Subject to any disclaimer, the term of this patent is extended or adjusted under 35 U.S.C. 154(b) by 0 days.

(21) Appl. No.: 17/138,203

(22) Filed: Dec. 30, 2020

(65) Prior Publication Data

US 2021/0113238 A1 Apr. 22, 2021

Related U.S. Application Data

(63) Continuation of application No. PCT/US2020/050249, filed on Sep. 10, 2020.
(Continued)

(51) Int. Cl.
*A61B 17/34* (2006.01)
*A61B 17/16* (2006.01)
(Continued)

(52) U.S. Cl.
CPC ...... *A61B 17/3423* (2013.01); *A61B 17/1633* (2013.01); *A61B 17/1671* (2013.01);
(Continued)

(58) Field of Classification Search
CPC ............ A61B 17/3423; A61B 17/1633; A61B 17/1671; A61B 17/3472; A61B 17/3445;
(Continued)

(56) References Cited

U.S. PATENT DOCUMENTS 3,054,881 A 9/1962 Metz et al.
3,062,876 A 11/1962 Pons, Jr. et al.
(Continued)

FOREIGN PATENT DOCUMENTS

EP 0040658 12/1981
EP 0584959 3/1994
(Continued)

OTHER PUBLICATIONS

Bailey, Jeannie F., "Innervation Patterns of PGP 9.5—Positive Nerve Fibers within the Human Lumbar Vertebra," Journal of Anatomy, (2011) 218, pp. 263-270, San Francisco, California.
(Continued)

*Primary Examiner* — Marcela I. Shirsat
(74) *Attorney, Agent, or Firm* — Knobbe Martens Olson & Bear LLP

(57) ABSTRACT

Described herein are various implementations of systems and methods for accessing and modulating tissue (for example, systems and methods for accessing and ablating nerves or other tissue within or surrounding a vertebral body to treat chronic lower back pain). Assessment of vertebral endplate degeneration or defects (e.g., pre-Modic changes) to facilitate identification of treatment sites and protocols are also provided in several embodiments. Several embodiments comprise the use of biomarkers to confirm or otherwise assess ablation, pain relief, efficacy of treatment, etc. Some embodiments include robotic elements for, as an example, facilitating robotically controlled access, navigation, imaging, and/or treatment.

21 Claims, 24 Drawing Sheets

Related U.S. Application Data

(60) Provisional application No. 62/899,622, filed on Sep. 12, 2019.

(51) Int. Cl.
*A61B 18/14* (2006.01)
*A61B 5/00* (2006.01)
*A61B 17/00* (2006.01)
*A61B 18/00* (2006.01)

(52) U.S. Cl.
CPC ...... *A61B 17/3472* (2013.01); *A61B 18/1492* (2013.01); *A61B 5/4848* (2013.01); *A61B 2017/00867* (2013.01); *A61B 2017/3445* (2013.01); *A61B 2018/0044* (2013.01)

(58) Field of Classification Search
CPC ............ A61B 17/1757; A61B 17/3478; A61B 17/1642; A61B 17/34; A61B 17/8816; A61B 18/1492
USPC ....................................................... 606/86 R
See application file for complete search history.

(56) References Cited

U.S. PATENT DOCUMENTS

| | | |
|---|---|---|
| 3,565,062 A | 2/1971 | Kuris |
| 3,822,708 A | 7/1974 | Zilber |
| 3,845,771 A | 11/1974 | Vise |
| 3,920,021 A | 11/1975 | Hiltebrandt |
| 3,938,502 A | 2/1976 | Bom |
| 3,977,408 A | 8/1976 | MacKew |
| 4,044,774 A | 8/1977 | Corbin et al. |
| 4,116,198 A | 9/1978 | Roos |
| 4,311,154 A | 1/1982 | Sterzer et al. |
| 4,312,364 A | 1/1982 | Convert et al. |
| 4,378,806 A | 4/1983 | Henley-Cohn |
| 4,448,198 A | 5/1984 | Turner |
| 4,449,528 A | 5/1984 | Auth et al. |
| 4,462,408 A | 7/1984 | Silverstein et al. |
| 4,528,979 A | 7/1985 | Marchenko et al. |
| 4,530,360 A | 7/1985 | Duarte |
| 4,541,423 A | 9/1985 | Barber |
| 4,569,351 A | 2/1986 | Tang |
| 4,573,448 A | 3/1986 | Kambin |
| 4,586,512 A | 5/1986 | Do-huu |
| 4,601,296 A | 7/1986 | Yerushalmi |
| 4,612,940 A | 9/1986 | Kasevich et al. |
| 4,657,017 A | 4/1987 | Sorochenko |
| 4,662,383 A | 5/1987 | Sogawa et al. |
| 4,671,293 A | 6/1987 | Shaulov |
| 4,676,258 A | 6/1987 | Inokuchi et al. |
| 4,679,561 A | 7/1987 | Doss |
| 4,681,122 A | 7/1987 | Winters et al. |
| 4,750,499 A | 6/1988 | Hoffer |
| 4,754,757 A | 7/1988 | Feucht |
| 4,757,820 A | 7/1988 | Itoh |
| 4,774,967 A | 10/1988 | Zanakis et al. |
| 4,800,899 A | 1/1989 | Elliott |
| 4,813,429 A | 3/1989 | Eshel et al. |
| 4,841,977 A | 6/1989 | Griffith et al. |
| 4,907,589 A | 3/1990 | Cosman |
| 4,924,863 A | 5/1990 | Sterzer |
| 4,936,281 A | 6/1990 | Stasz |
| 4,941,466 A | 7/1990 | Romano |
| 4,950,267 A | 8/1990 | Ishihara et al. |
| 4,951,677 A | 8/1990 | Crowley et al. |
| 4,955,377 A | 9/1990 | Lennox et al. |
| 4,959,063 A | 9/1990 | Kojima |
| 4,961,435 A | 10/1990 | Kitagawa et al. |
| 4,963,142 A | 10/1990 | Loertscher |
| 4,966,144 A | 10/1990 | Rochkind et al. |
| 4,967,765 A | 11/1990 | Turner et al. |
| 4,976,711 A | 12/1990 | Parins et al. |
| 4,977,902 A | 12/1990 | Sekino et al. |
| 5,000,185 A | 3/1991 | Yock |
| 5,002,058 A | 3/1991 | Marinelli |
| 5,002,059 A | 3/1991 | Crowley et al. |
| 5,007,437 A | 4/1991 | Sterzer |
| 5,025,778 A | 6/1991 | Silverstein et al. |
| 5,031,618 A | 7/1991 | Mullet |
| 5,061,266 A | 10/1991 | Hakky |
| 5,070,879 A | 12/1991 | Herres |
| RE33,791 E | 1/1992 | Carr |
| 5,078,736 A | 1/1992 | Behl |
| 5,080,660 A | 1/1992 | Buelna |
| 5,084,043 A | 1/1992 | Hertzmann et al. |
| 5,090,414 A | 2/1992 | Takano |
| 5,098,431 A | 3/1992 | Rydell |
| 5,106,376 A | 4/1992 | Mononen et al. |
| 5,108,404 A | 4/1992 | Scholten et al. |
| 5,131,397 A | 7/1992 | Crowley |
| 5,147,355 A | 9/1992 | Cravalho et al. |
| 5,156,157 A | 10/1992 | Nappholz et al. |
| 5,158,536 A | 10/1992 | Sekins et al. |
| 5,161,533 A | 11/1992 | Prass et al. |
| 5,167,231 A | 12/1992 | Matsui |
| 5,186,177 A | 2/1993 | O'Donnell et al. |
| 5,190,540 A | 3/1993 | Lee |
| 5,190,546 A | 3/1993 | Jervis |
| 5,201,729 A | 4/1993 | Hertzmann et al. |
| 5,207,672 A | 5/1993 | Martinelli et al. |
| 5,209,748 A | 5/1993 | Daikuzono |
| 5,222,953 A | 6/1993 | Dowlatshahi |
| 5,226,430 A | 7/1993 | Bourgelais et al. |
| 5,242,439 A | 9/1993 | Larsen et al. |
| 5,255,679 A | 10/1993 | Imran |
| 5,271,408 A | 12/1993 | Breyer et al. |
| 5,273,026 A | 12/1993 | Wilk |
| 5,281,213 A | 1/1994 | Milder et al. |
| 5,281,215 A | 1/1994 | Milder |
| 5,282,468 A | 2/1994 | Klepinski |
| 5,292,321 A | 3/1994 | Lee |
| 5,295,484 A | 3/1994 | Hynynen et al. |
| 5,300,085 A | 4/1994 | Yock |
| 5,304,214 A | 4/1994 | DeFord et al. |
| 5,305,756 A | 4/1994 | Entrekin et al. |
| 5,314,463 A | 5/1994 | Camps et al. |
| 5,320,617 A | 6/1994 | Leach |
| 5,324,255 A | 6/1994 | Gesswein et al. |
| 5,325,860 A | 7/1994 | Seward et al. |
| 5,342,292 A | 8/1994 | Nita et al. |
| 5,342,357 A | 8/1994 | Nardella |
| 5,342,409 A | 8/1994 | Mullett |
| 5,344,435 A | 9/1994 | Schaefermeyer et al. |
| 5,345,940 A | 9/1994 | Seward et al. |
| 5,348,554 A | 9/1994 | Imran et al. |
| 5,350,377 A | 9/1994 | Winston et al. |
| 5,351,691 A | 10/1994 | Brommersma |
| 5,366,443 A | 11/1994 | Eggers et al. |
| 5,366,490 A | 11/1994 | Edwards et al. |
| 5,368,031 A | 11/1994 | Cline et al. |
| 5,368,035 A | 11/1994 | Crowley et al. |
| 5,368,557 A | 11/1994 | Mills et al. |
| 5,368,558 A | 11/1994 | Nita |
| 5,370,675 A | 12/1994 | Edwards et al. |
| 5,370,678 A | 12/1994 | Edwards et al. |
| 5,372,138 A | 12/1994 | Abele et al. |
| 5,374,265 A | 12/1994 | Sand |
| 5,383,876 A | 1/1995 | Nardella |
| 5,385,148 A | 1/1995 | Jackson et al. |
| 5,385,544 A | 1/1995 | Edwards et al. |
| 5,391,197 A | 2/1995 | Burdette et al. |
| 5,391,199 A | 2/1995 | Ben-Haim |
| 5,405,376 A | 4/1995 | Mulier et al. |
| 5,411,527 A | 5/1995 | Alt |
| 5,417,719 A | 5/1995 | Hull et al. |
| 5,419,767 A | 5/1995 | Eggers et al. |
| 5,421,338 A | 6/1995 | Crowley et al. |
| 5,423,811 A | 6/1995 | Imran et al. |
| 5,431,649 A | 7/1995 | Mulier et al. |
| 5,433,739 A | 7/1995 | Sluijter et al. |
| D361,555 S | 8/1995 | Bettin et al. |
| 5,437,661 A | 8/1995 | Rieser |

(56) References Cited

U.S. PATENT DOCUMENTS

| | | |
|---|---|---|
| 5,441,499 A | 8/1995 | Fritzsch |
| 5,441,527 A | 8/1995 | Erickson et al. |
| 5,443,463 A | 8/1995 | Stern et al. |
| 5,447,509 A | 9/1995 | Mills et al. |
| 5,449,380 A | 9/1995 | Chin |
| 5,454,373 A | 10/1995 | Crowley |
| 5,458,596 A | 10/1995 | Lax et al. |
| 5,458,597 A | 10/1995 | Edwards et al. |
| 5,471,988 A | 12/1995 | Fujio et al. |
| 5,472,441 A | 12/1995 | Edwards et al. |
| 5,474,530 A | 12/1995 | Gesswein et al. |
| 5,484,432 A | 1/1996 | Sand |
| 5,486,170 A | 1/1996 | Winston et al. |
| 5,501,703 A | 3/1996 | Holsheimer et al. |
| 5,505,730 A | 4/1996 | Edwards |
| 5,514,130 A | 5/1996 | Baker |
| 5,524,624 A | 6/1996 | Tepper et al. |
| 5,526,815 A | 6/1996 | Granz et al. |
| 5,529,580 A | 6/1996 | Hagino et al. |
| 5,540,679 A | 7/1996 | Berns et al. |
| 5,540,681 A | 7/1996 | Stru et al. |
| 5,540,684 A | 7/1996 | Hassler, Jr. |
| 5,545,161 A | 8/1996 | Imran |
| 5,560,362 A | 10/1996 | Curley et al. |
| 5,565,005 A | 10/1996 | Bertin et al. |
| 5,569,242 A | 10/1996 | Lax et al. |
| 5,571,088 A | 11/1996 | Beaudet et al. |
| 5,571,147 A | 11/1996 | Sluijter et al. |
| 5,575,772 A | 11/1996 | Lennox |
| 5,575,788 A | 11/1996 | Baker et al. |
| 5,588,432 A | 12/1996 | Crowley |
| 5,596,988 A | 1/1997 | Markle et al. |
| 5,601,526 A | 2/1997 | Blanc et al. |
| 5,606,974 A | 3/1997 | Castellano et al. |
| 5,609,151 A | 3/1997 | Mulier et al. |
| 5,620,479 A | 4/1997 | Diederich |
| 5,628,317 A | 5/1997 | Starkebaum et al. |
| 5,630,426 A | 5/1997 | Shmulewitz et al. |
| 5,630,837 A | 5/1997 | Crowley |
| 5,643,319 A | 7/1997 | Green et al. |
| 5,643,330 A | 7/1997 | Holsheimer et al. |
| 5,647,361 A | 7/1997 | Damadian |
| 5,647,871 A | 7/1997 | Levine et al. |
| 5,658,278 A | 8/1997 | Imran et al. |
| 5,672,173 A | 9/1997 | Gough et al. |
| 5,681,282 A | 10/1997 | Eggers et al. |
| 5,683,366 A | 11/1997 | Eggers et al. |
| 5,685,839 A | 11/1997 | Baker et al. |
| 5,687,729 A | 11/1997 | Schaetzle |
| 5,688,267 A | 11/1997 | Panescu |
| 5,693,052 A | 12/1997 | Weaver |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,697,927 A | 12/1997 | Imran et al. |
| 5,700,262 A | 12/1997 | Acosta et al. |
| 5,718,231 A | 2/1998 | Chen et al. |
| 5,720,286 A | 2/1998 | Blanc et al. |
| 5,720,287 A | 2/1998 | Chapelon et al. |
| 5,722,403 A | 3/1998 | McGee et al. |
| 5,725,494 A | 3/1998 | Brisken |
| 5,728,062 A | 3/1998 | Brisken |
| 5,730,706 A | 3/1998 | Garnies |
| 5,733,315 A | 3/1998 | Burdette et al. |
| 5,735,280 A | 4/1998 | Sherman et al. |
| 5,735,811 A | 4/1998 | Brisken |
| 5,735,846 A | 4/1998 | Fleischman et al. |
| 5,735,847 A | 4/1998 | Gough et al. |
| 5,738,680 A | 4/1998 | Mueller et al. |
| 5,741,249 A | 4/1998 | Moss et al. |
| 5,743,904 A | 4/1998 | Edwards |
| 5,746,737 A | 5/1998 | Saadat |
| 5,752,969 A | 5/1998 | Cunci et al. |
| 5,755,663 A | 5/1998 | Johnson et al. |
| 5,762,066 A | 6/1998 | Law et al. |
| 5,762,616 A | 6/1998 | Talish |
| 5,766,153 A | 6/1998 | Eggers et al. |
| 5,766,231 A | 6/1998 | Bettin |
| 5,776,092 A | 7/1998 | Farin et al. |
| 5,785,705 A | 7/1998 | Baker |
| 5,800,378 A | 9/1998 | Edwards et al. |
| 5,800,429 A | 9/1998 | Edwards |
| 5,800,432 A | 9/1998 | Swanson |
| 5,807,237 A | 9/1998 | Tindel |
| 5,807,391 A | 9/1998 | Cornelius et al. |
| 5,807,392 A | 9/1998 | Eggers |
| 5,807,395 A | 9/1998 | Mulier et al. |
| 5,810,764 A | 9/1998 | Eggers et al. |
| 5,817,021 A | 10/1998 | Reichenberger |
| 5,824,021 A | 10/1998 | Rise |
| 5,840,031 A | 11/1998 | Crowley |
| 5,843,019 A | 12/1998 | Eggers et al. |
| 5,843,021 A | 12/1998 | Edwards et al. |
| 5,844,092 A | 12/1998 | Presta et al. |
| 5,846,218 A | 12/1998 | Brisken et al. |
| 5,849,011 A | 12/1998 | Jones et al. |
| 5,855,576 A | 1/1999 | LeVeen et al. |
| 5,860,951 A | 1/1999 | Eggers et al. |
| 5,865,788 A | 2/1999 | Edwards et al. |
| 5,865,801 A | 2/1999 | Houser |
| 5,868,740 A | 2/1999 | LeVeen et al. |
| 5,871,469 A | 2/1999 | Eggers et al. |
| 5,871,470 A | 2/1999 | MeWha |
| 5,871,481 A | 2/1999 | Kannenberg et al. |
| 5,873,855 A | 2/1999 | Eggers et al. |
| 5,873,877 A | 2/1999 | McGaffigan et al. |
| 5,876,398 A | 3/1999 | Mulier et al. |
| 5,888,198 A | 3/1999 | Eggers et al. |
| 5,891,095 A | 4/1999 | Eggers et al. |
| 5,895,370 A | 4/1999 | Edwards et al. |
| 5,902,272 A | 5/1999 | Eggers |
| 5,902,308 A | 5/1999 | Murphy |
| 5,904,681 A | 5/1999 | West, Jr. |
| 5,906,613 A | 5/1999 | Mulier et al. |
| 5,916,213 A | 6/1999 | Haissaguerre et al. |
| 5,916,214 A | 6/1999 | Cosio |
| 5,919,188 A | 7/1999 | Shearon et al. |
| 5,931,805 A | 8/1999 | Brisken |
| 5,935,123 A | 8/1999 | Edwards et al. |
| 5,938,582 A | 8/1999 | Ciamacco et al. |
| 5,941,722 A | 8/1999 | Chen |
| 5,941,876 A | 8/1999 | Nardella et al. |
| 5,944,715 A | 8/1999 | Goble et al. |
| 5,948,007 A | 9/1999 | Starkebaum et al. |
| 5,948,008 A | 9/1999 | Daikuzono |
| 5,954,716 A | 9/1999 | Sharkey et al. |
| 5,964,727 A | 10/1999 | Edwards et al. |
| 5,967,988 A | 10/1999 | Briscoe et al. |
| 5,972,015 A | 10/1999 | Scribner et al. |
| 5,976,105 A | 11/1999 | Casson et al. |
| 5,983,141 A | 11/1999 | Sluijter et al. |
| 5,997,497 A | 12/1999 | Nita et al. |
| 6,001,095 A | 12/1999 | de la Rama et al. |
| 6,007,533 A | 12/1999 | Casscells et al. |
| 6,007,570 A | 12/1999 | Sharkey et al. |
| 6,012,457 A | 1/2000 | Lesh |
| 6,014,588 A | 1/2000 | Fitz |
| 6,016,452 A | 1/2000 | Kasevich |
| 6,016,809 A | 1/2000 | Mulier et al. |
| 6,017,356 A | 1/2000 | Frederick et al. |
| 6,019,776 A | 2/2000 | Preissman et al. |
| 6,022,334 A | 2/2000 | Edwards et al. |
| 6,024,733 A | 2/2000 | Eggers et al. |
| 6,024,740 A | 2/2000 | Langberg et al. |
| 6,030,374 A | 2/2000 | McDaniel |
| 6,030,402 A | 2/2000 | Thompson et al. |
| 6,032,673 A | 3/2000 | Alden et al. |
| 6,032,674 A | 3/2000 | Eggers et al. |
| 6,033,411 A | 3/2000 | Preissman et al. |
| 6,035,238 A | 3/2000 | Ingle et al. |
| 6,045,532 A | 4/2000 | Eggers et al. |
| 6,046,187 A | 4/2000 | Berde et al. |
| 6,047,214 A | 4/2000 | Gyurcsik et al. |

(56) References Cited

U.S. PATENT DOCUMENTS

| | | |
|---|---|---|
| 6,050,995 A | 4/2000 | Durgin |
| 6,053,172 A | 4/2000 | Hovda et al. |
| 6,053,909 A | 4/2000 | Shadduck |
| 6,038,480 A | 5/2000 | Hrdlicka et al. |
| 6,063,078 A | 5/2000 | Wittkampf |
| 6,063,079 A | 5/2000 | Hovda et al. |
| 6,066,134 A | 5/2000 | Eggers et al. |
| 6,066,139 A | 5/2000 | Ryan et al. |
| 6,068,642 A | 5/2000 | Johnson et al. |
| 6,071,279 A | 6/2000 | Fleishman et al. |
| 6,073,051 A | 6/2000 | Sharkey et al. |
| 6,074,352 A | 6/2000 | Foldes et al. |
| 6,086,585 A | 7/2000 | Hovda et al. |
| 6,090,105 A | 7/2000 | Zepeda et al. |
| 6,095,149 A | 8/2000 | Sharkey et al. |
| 6,099,499 A | 8/2000 | Ciamacco |
| 6,099,514 A | 8/2000 | Sharkey et al. |
| 6,099,524 A | 8/2000 | Lipson et al. |
| 6,102,046 A | 8/2000 | Weinstein et al. |
| 6,104,957 A | 8/2000 | Alo et al. |
| 6,105,581 A | 8/2000 | Eggers et al. |
| 6,106,454 A | 8/2000 | Berg et al. |
| 6,109,268 A | 8/2000 | Thapliyal et al. |
| 6,112,122 A | 8/2000 | Schwardt et al. |
| 6,113,597 A | 9/2000 | Eggers et al. |
| 6,117,101 A | 9/2000 | Diederich et al. |
| 6,117,109 A | 9/2000 | Eggers et al. |
| 6,117,128 A | 9/2000 | Gregory |
| 6,120,467 A | 9/2000 | Schallhorn |
| 6,120,502 A | 9/2000 | Michelson |
| 6,122,549 A | 9/2000 | Sharkey et al. |
| 6,126,682 A | 10/2000 | Ashley et al. |
| 6,137,209 A | 10/2000 | Dahlberg et al. |
| 6,139,545 A | 10/2000 | Utley et al. |
| 6,142,992 A | 11/2000 | Cheng et al. |
| 6,143,019 A | 11/2000 | Motamedi et al. |
| 6,146,380 A | 11/2000 | Racz et al. |
| 6,149,620 A | 11/2000 | Baker et al. |
| 6,159,194 A | 12/2000 | Eggers et al. |
| 6,159,208 A | 12/2000 | Hovda et al. |
| 6,161,048 A | 12/2000 | Sluitjer et al. |
| 6,164,283 A | 12/2000 | Lesh |
| 6,165,172 A | 12/2000 | Farley et al. |
| 6,168,593 B1 | 1/2001 | Sharkey et al. |
| 6,169,924 B1 | 1/2001 | Meloy et al. |
| 6,171,239 B1 | 1/2001 | Humphrey |
| 6,176,857 B1 | 1/2001 | Ashley |
| 6,179,824 B1 | 1/2001 | Eggers et al. |
| 6,179,836 B1 | 1/2001 | Eggers et al. |
| 6,179,858 B1 | 1/2001 | Squire et al. |
| 6,183,469 B1 | 2/2001 | Thapliyal et al. |
| 6,190,381 B1 | 2/2001 | Olsen et al. |
| 6,190,383 B1 | 2/2001 | Schmaltz et al. |
| 6,193,715 B1 | 2/2001 | Wrublewski et al. |
| 6,203,542 B1 | 3/2001 | Ellsberry et al. |
| 6,206,842 B1 | 3/2001 | Tu et al. |
| 6,210,393 B1 | 4/2001 | Brisken |
| 6,210,402 B1 | 4/2001 | Olsen et al. |
| 6,210,415 B1 | 4/2001 | Bester |
| 6,216,704 B1 | 4/2001 | Ingle et al. |
| 6,221,038 B1 | 4/2001 | Brisken |
| 6,224,592 B1 | 5/2001 | Eggers et al. |
| 6,228,046 B1 | 5/2001 | Brisken |
| 6,228,078 B1 | 5/2001 | Eggers et al. |
| 6,228,082 B1 | 5/2001 | Baker et al. |
| 6,231,516 B1 | 5/2001 | Keilman et al. |
| 6,231,528 B1 | 5/2001 | Kaufman et al. |
| 6,231,571 B1 | 5/2001 | Ellman et al. |
| 6,231,615 B1 | 5/2001 | Preissman |
| 6,233,488 B1 | 5/2001 | Hess |
| 6,235,020 B1 | 5/2001 | Cheng et al. |
| 6,235,024 B1 | 5/2001 | Tu |
| 6,237,604 B1 | 5/2001 | Burnside et al. |
| 6,238,391 B1 | 5/2001 | Olsen et al. |
| 6,238,393 B1 | 5/2001 | Mulier et al. |
| 6,241,665 B1 | 6/2001 | Negus et al. |
| 6,241,725 B1 | 6/2001 | Cosman |
| 6,241,734 B1 | 6/2001 | Scribner et al. |
| 6,245,064 B1 | 6/2001 | Lesh |
| 6,246,912 B1 | 6/2001 | Sluijter et al. |
| 6,248,110 B1 | 6/2001 | Reiley et al. |
| 6,248,345 B1 | 6/2001 | Goldenheim et al. |
| 6,253,086 B1 | 7/2001 | Ashley et al. |
| 6,254,553 B1 | 7/2001 | Lidgren et al. |
| 6,254,599 B1 | 7/2001 | Lesh et al. |
| 6,254,600 B1 | 7/2001 | Willink et al. |
| 6,259,952 B1 | 7/2001 | Sluigter |
| 6,261,311 B1 | 7/2001 | Sharkey et al. |
| 6,264,650 B1 | 7/2001 | Hovda et al. |
| 6,264,651 B1 | 7/2001 | Underwood et al. |
| 6,264,652 B1 | 7/2001 | Eggers et al. |
| 6,264,659 B1 | 7/2001 | Ross et al. |
| 6,267,770 B1 | 7/2001 | Truwit |
| 6,270,498 B1 | 8/2001 | Michelson |
| 6,277,112 B1 | 8/2001 | Underwood et al. |
| 6,277,122 B1 | 8/2001 | McGahan et al. |
| 6,280,441 B1 | 8/2001 | Ryan |
| 6,280,456 B1 | 8/2001 | Scribner et al. |
| 6,283,961 B1 | 9/2001 | Underwood et al. |
| 6,287,114 B1 | 9/2001 | Meller et al. |
| 6,287,272 B1 | 9/2001 | Brisken et al. |
| 6,287,304 B1 | 9/2001 | Eggers et al. |
| 6,290,715 B1 | 9/2001 | Sharkey et al. |
| 6,292,699 B1 | 9/2001 | Simon et al. |
| 6,296,619 B1 | 10/2001 | Brisken et al. |
| 6,296,636 B1 | 10/2001 | Cheng et al. |
| 6,296,638 B1 | 10/2001 | Davison et al. |
| 6,305,378 B1 | 10/2001 | Lesh et al. |
| 6,309,387 B1 | 10/2001 | Eggers et al. |
| 6,309,420 B1 | 10/2001 | Preissman |
| 6,312,408 B1 | 11/2001 | Eggers et al. |
| 6,312,425 B1 | 11/2001 | Simpson et al. |
| 6,312,426 B1 | 11/2001 | Goldberg et al. |
| 6,319,241 B1 | 11/2001 | King et al. |
| 6,322,549 B1 | 11/2001 | Eggers et al. |
| 6,348,055 B1 | 2/2002 | Preissman |
| 6,355,032 B1 | 3/2002 | Hovda et al. |
| 6,356,790 B1 | 3/2002 | Maguire et al. |
| 6,361,531 B1 | 3/2002 | Hissang |
| 6,363,937 B1 | 4/2002 | Hovda et al. |
| 6,368,292 B1 | 4/2002 | Ogden et al. |
| 6,379,351 B1 | 4/2002 | Thapliyal et al. |
| 6,383,190 B1 | 5/2002 | Preissman |
| 6,391,025 B1 | 5/2002 | Weinstein et al. |
| 6,398,782 B1 | 6/2002 | Pecor et al. |
| 6,416,507 B1 | 7/2002 | Eggers et al. |
| 6,416,508 B1 | 7/2002 | Eggers et al. |
| 6,423,057 B1 | 7/2002 | He et al. |
| 6,423,059 B1 | 7/2002 | Hanson et al. |
| 6,425,887 B1 | 7/2002 | McGuckin et al. |
| 6,426,339 B1 | 7/2002 | Berde et al. |
| 6,428,491 B1 | 8/2002 | Weiss |
| 6,432,103 B1 | 8/2002 | Ellsberry et al. |
| 6,436,060 B1 | 8/2002 | Talish |
| 6,436,098 B1 | 8/2002 | Michelson |
| 6,440,138 B1 | 8/2002 | Reiley et al. |
| 6,447,448 B1 | 9/2002 | Ishikawa et al. |
| 6,451,013 B1 | 9/2002 | Bays et al. |
| 6,454,727 B1 | 9/2002 | Bubank et al. |
| 6,461,350 B1 | 10/2002 | Underwood et al. |
| 6,461,354 B1 | 10/2002 | Olsen et al. |
| 6,464,695 B2 | 10/2002 | Hovda et al. |
| 6,468,270 B1 | 10/2002 | Hovda et al. |
| 6,468,274 B1 | 10/2002 | Alleyne et al. |
| 6,470,220 B1 | 10/2002 | Kraus et al. |
| 6,478,793 B1 | 11/2002 | Cosman et al. |
| 6,482,201 B1 | 11/2002 | Olsen et al. |
| 6,485,271 B1 | 11/2002 | Tack |
| 6,487,446 B1 | 11/2002 | Hill et al. |
| 6,491,893 B1 | 12/2002 | Babich |
| 6,493,592 B1 | 12/2002 | Leonard et al. |
| 6,494,902 B2 | 12/2002 | Hoey et al. |
| 6,500,173 B2 | 12/2002 | Underwood et al. |
| 6,505,075 B1 | 1/2003 | Weiner |

(56) References Cited

U.S. PATENT DOCUMENTS

| | | |
|---|---|---|
| 6,508,839 B1 | 1/2003 | Lambrecht et al. |
| 6,524,261 B2 | 2/2003 | Talish et al. |
| 6,527,759 B1 | 3/2003 | Tachibana et al. |
| 6,537,306 B1 | 3/2003 | Burdette et al. |
| 6,540,741 B1 | 4/2003 | Underwood et al. |
| 6,544,261 B2 | 4/2003 | Ellsberry et al. |
| 6,557,559 B1 | 5/2003 | Eggers et al. |
| 6,558,385 B1 | 5/2003 | McClurken et al. |
| 6,558,390 B2 | 5/2003 | Cragg |
| 6,560,486 B1 | 5/2003 | Osorio et al. |
| 6,562,033 B2 | 5/2003 | Shah et al. |
| 6,575,919 B1 * | 6/2003 | Reiley .................. A61B 17/34 600/567 |
| 6,575,968 B1 | 6/2003 | Eggers et al. |
| 6,575,969 B1 | 6/2003 | Rittman et al. |
| 6,575,979 B1 | 6/2003 | Cragg |
| 6,578,579 B2 | 6/2003 | Burnside et al. |
| 6,582,423 B1 | 6/2003 | Thapliyai et al. |
| 6,585,656 B2 | 7/2003 | Masters |
| 6,589,237 B2 | 7/2003 | Woloszko et al. |
| 6,592,559 B1 | 7/2003 | Pakter et al. |
| 6,595,990 B1 | 7/2003 | Weinstein et al. |
| 6,599,288 B2 | 7/2003 | Maguire et al. |
| 6,602,248 B1 | 8/2003 | Sharps et al. |
| 6,604,003 B2 | 8/2003 | Fredricks et al. |
| 6,607,502 B1 | 8/2003 | Maguire et al. |
| 6,607,529 B1 | 8/2003 | Jones et al. |
| 6,608,502 B2 | 8/2003 | Aoki et al. |
| 6,622,731 B2 | 9/2003 | Daniel et al. |
| 6,623,505 B2 | 9/2003 | Scribner et al. |
| 6,632,193 B1 | 10/2003 | Davison et al. |
| 6,632,220 B1 | 10/2003 | Eggers et al. |
| 6,645,202 B1 | 11/2003 | Pless et al. |
| 6,648,883 B2 | 11/2003 | Francischelli et al. |
| 6,651,669 B1 | 11/2003 | Burnside |
| 6,659,106 B1 | 12/2003 | Hovda et al. |
| 6,663,627 B2 | 12/2003 | Francischelli et al. |
| 6,663,647 B2 | 12/2003 | Relley et al. |
| 6,673,063 B2 | 1/2004 | Brett |
| 6,689,086 B1 | 2/2004 | Nita et al. |
| 6,689,125 B1 | 2/2004 | Keith et al. |
| 6,692,450 B1 | 2/2004 | Coleman |
| 6,699,240 B2 | 3/2004 | Francischelli |
| 6,699,242 B2 | 3/2004 | Heggeness |
| 6,709,432 B2 | 3/2004 | Ferek-Patric |
| 6,718,208 B2 | 4/2004 | Hill et al. |
| 6,719,761 B1 | 4/2004 | Reiley et al. |
| 6,723,087 B2 | 4/2004 | O'Neill et al. |
| 6,723,094 B1 | 4/2004 | Desinger |
| 6,726,684 B1 | 4/2004 | Woloszko et al. |
| 6,736,810 B2 | 5/2004 | Hoey et al. |
| 6,736,835 B2 | 5/2004 | Pellegrino et al. |
| 6,745,079 B2 | 6/2004 | King |
| 6,746,447 B2 | 6/2004 | Davison et al. |
| 6,746,451 B2 | 6/2004 | Middleton et al. |
| 6,749,604 B1 | 6/2004 | Eggers et al. |
| 6,758,846 B2 | 7/2004 | Goble et al. |
| 6,770,071 B2 | 8/2004 | Woioszko et al. |
| 6,772,012 B2 | 8/2004 | Ricart et al. |
| 6,773,431 B2 | 8/2004 | Eggers et al. |
| 6,795,737 B2 | 9/2004 | Gielen et al. |
| 6,805,697 B1 | 10/2004 | Helm et al. |
| 6,827,715 B2 | 12/2004 | Francischelli et al. |
| 6,827,716 B2 | 12/2004 | Ryan et al. |
| 6,832,996 B2 | 12/2004 | Woloszko et al. |
| 6,837,887 B2 | 1/2005 | Woloszko et al. |
| 6,837,888 B2 | 1/2005 | Ciarrocca et al. |
| 6,852,091 B2 | 2/2005 | Edwards et al. |
| 6,863,672 B2 | 3/2005 | Reiley et al. |
| 6,875,219 B2 | 4/2005 | Arramon et al. |
| 6,881,214 B2 | 4/2005 | Cosman et al. |
| 6,896,674 B1 | 5/2005 | Woloszko et al. |
| 6,896,675 B2 | 5/2005 | Leung et al. |
| 6,907,884 B2 | 6/2005 | Pellegrino et al. |
| 6,915,806 B2 | 7/2005 | Pacek et al. |
| 6,922,579 B2 | 7/2005 | Taimisto et al. |
| 6,923,813 B2 | 8/2005 | Phillips et al. |
| 6,936,046 B2 | 8/2005 | Hissong et al. |
| 6,955,674 B2 | 10/2005 | Eick et al. |
| 6,960,204 B2 | 11/2005 | Eggers et al. |
| 6,962,589 B2 | 11/2005 | Mulier et al. |
| 6,974,453 B2 | 12/2005 | Woloszko et al. |
| 6,980,849 B2 | 12/2005 | Sasso |
| 6,981,981 B2 | 1/2006 | Reiley et al. |
| 6,989,010 B2 | 1/2006 | Francischelli et al. |
| 6,997,941 B2 | 2/2006 | Sharkey et al. |
| 7,001,383 B2 | 2/2006 | Keidar |
| 7,041,096 B2 | 5/2006 | Malis et al. |
| 7,044,954 B2 | 5/2006 | Reiley et al. |
| 7,048,743 B2 | 5/2006 | Miller et al. |
| 7,065,408 B2 | 6/2006 | Herman et al. |
| 7,081,122 B1 | 7/2006 | Reiley et al. |
| 7,090,672 B2 | 8/2006 | Underwood et al. |
| 7,104,989 B2 | 9/2006 | Skarda |
| 7,118,574 B2 | 10/2006 | Patel et al. |
| 7,131,969 B1 | 11/2006 | Hovda et al. |
| 7,153,307 B2 | 12/2006 | Scribner et al. |
| 7,163,536 B2 | 1/2007 | Godara |
| 7,177,678 B1 | 2/2007 | Osorio et al. |
| 7,179,255 B2 | 2/2007 | Lettice et al. |
| 7,186,234 B2 | 3/2007 | Dahla et al. |
| 7,192,428 B2 | 3/2007 | Eggers et al. |
| 7,201,731 B1 | 4/2007 | Lundquist et al. |
| 7,201,750 B1 | 4/2007 | Eggers et al. |
| 7,211,055 B2 | 5/2007 | Diederich et al. |
| 7,217,268 B2 | 5/2007 | Eggers et al. |
| 7,238,184 B2 | 7/2007 | Megerman et al. |
| 7,241,297 B2 | 7/2007 | Shaolian et al. |
| 7,250,048 B2 | 7/2007 | Francischelli et al. |
| 7,258,690 B2 | 8/2007 | Sutton et al. |
| 7,270,659 B2 | 9/2007 | Ricart et al. |
| 7,270,661 B2 | 9/2007 | Dahla et al. |
| 7,276,063 B2 | 10/2007 | Davison et al. |
| 7,294,127 B2 | 11/2007 | Leung et al. |
| 7,305,264 B2 | 12/2007 | Larson et al. |
| 7,306,596 B2 | 12/2007 | Hillier et al. |
| 7,306,598 B2 | 12/2007 | Truckai et al. |
| 7,318,823 B2 | 1/2008 | Sharps et al. |
| 7,318,826 B2 | 1/2008 | Teitelbaum et al. |
| 7,326,203 B2 | 2/2008 | Papineau et al. |
| 7,331,956 B2 | 2/2008 | Hovda et al. |
| 7,331,957 B2 | 2/2008 | Woloszko et al. |
| RE40,156 E | 3/2008 | Sharps et al. |
| 7,346,391 B1 | 3/2008 | Osorio et al. |
| 7,386,350 B2 | 6/2008 | Vilims |
| 7,387,625 B2 | 6/2008 | Hovda et al. |
| 7,393,351 B2 | 7/2008 | Woloszko et al. |
| 7,399,306 B2 | 7/2008 | Reiley et al. |
| 7,422,585 B1 | 9/2008 | Eggers et al. |
| 7,429,262 B2 | 9/2008 | Woloszko et al. |
| 7,435,247 B2 | 10/2008 | Woloszko et al. |
| 7,435,250 B2 | 10/2008 | Francischelli et al. |
| 7,442,191 B2 | 10/2008 | Hovda et al. |
| 7,468,059 B2 | 12/2008 | Eggers et al. |
| 7,480,533 B2 | 1/2009 | Cosman et al. |
| 7,502,652 B2 | 3/2009 | Gaunt et al. |
| 7,503,920 B2 | 3/2009 | Siegal |
| 7,503,921 B2 | 3/2009 | Siegal |
| 7,507,236 B2 | 3/2009 | Eggers et al. |
| 7,546,164 B2 | 6/2009 | King |
| 7,553,307 B2 | 6/2009 | Bleich et al. |
| 7,553,309 B2 | 6/2009 | Buysse et al. |
| 7,555,343 B2 | 6/2009 | Bleich |
| 7,559,932 B2 | 7/2009 | Truckai et al. |
| 7,569,626 B2 | 8/2009 | Truckai |
| 7,574,257 B2 | 8/2009 | Rittman, III |
| 7,585,300 B2 | 9/2009 | Cha |
| 7,593,778 B2 | 9/2009 | Chandran et al. |
| 7,594,913 B2 | 9/2009 | Ormsby et al. |
| 7,604,636 B1 | 10/2009 | Walters et al. |
| 7,621,952 B2 | 11/2009 | Truckai et al. |
| 7,645,277 B2 | 1/2010 | McClurken et al. |
| 7,678,111 B2 | 3/2010 | Mulier et al. |
| 7,678,116 B2 | 3/2010 | Truckai et al. |

(56) References Cited

U.S. PATENT DOCUMENTS

| | | | |
|---|---|---|---|
| 7,682,378 B2 | 3/2010 | Truckai et al. |
| 7,708,733 B2 | 5/2010 | Sanders et al. |
| 7,722,620 B2 | 5/2010 | Truckai et al. |
| 7,731,720 B2 | 6/2010 | Truckai et al. |
| 7,738,968 B2 | 6/2010 | Bleich |
| 7,740,631 B2 | 6/2010 | Bleich et al. |
| 7,749,218 B2 | 7/2010 | Pellegrino et al. |
| 7,749,220 B2 | 7/2010 | Schmaltz et al. |
| 7,792,588 B2 | 9/2010 | Harding |
| 7,799,021 B2 | 9/2010 | Leung et al. |
| 7,819,826 B2 | 10/2010 | Diederich et al. |
| 7,819,869 B2 | 10/2010 | Godara et al. |
| 7,824,398 B2 | 11/2010 | Woloszko et al. |
| 7,824,404 B2 | 11/2010 | Godara et al. |
| 7,828,804 B2 | 11/2010 | Li et al. |
| 7,846,156 B2 | 12/2010 | Malis et al. |
| 7,850,685 B2 | 12/2010 | Kunis et al. |
| 7,853,326 B2 | 12/2010 | Rittman, III |
| 7,857,813 B2 | 12/2010 | Schmitz et al. |
| 7,879,032 B1 | 2/2011 | Garito et al. |
| 7,887,543 B2 | 2/2011 | Sand et al. |
| 7,892,235 B2 * | 2/2011 | Ellis ............... B23B 51/00 606/80 |
| 7,896,870 B2 | 3/2011 | Arless et al. |
| 7,896,909 B2 | 3/2011 | Sharkey et al. |
| 7,901,403 B2 | 3/2011 | Woloszko et al. |
| 7,909,827 B2 | 3/2011 | Reiley et al. |
| 7,909,873 B2 | 3/2011 | Tan-Melecki et al. |
| 7,914,526 B2 | 3/2011 | Lehmann et al. |
| 7,914,535 B2 | 3/2011 | Assell et al. |
| 7,917,222 B1 | 3/2011 | Osorio et al. |
| 7,918,849 B2 | 4/2011 | Bleich et al. |
| 7,918,874 B2 | 4/2011 | Siegal |
| 7,938,835 B2 * | 5/2011 | Boucher ............ A61B 17/8816 606/93 |
| 7,945,331 B2 | 5/2011 | Vilims |
| 7,951,140 B2 | 5/2011 | Arless et al. |
| 7,959,634 B2 | 6/2011 | Sennett |
| 7,963,915 B2 | 6/2011 | Bleich |
| 7,967,827 B2 | 6/2011 | Osorio et al. |
| 7,972,340 B2 | 7/2011 | Sand et al. |
| 8,000,785 B2 | 8/2011 | Ritmann, III |
| 8,021,401 B2 | 9/2011 | Carl et al. |
| 8,025,688 B2 | 9/2011 | Diederich et al. |
| 8,034,052 B2 | 10/2011 | Podhajsky |
| 8,034,071 B2 | 10/2011 | Scribner et al. |
| 8,043,287 B2 | 10/2011 | Conquergood et al. |
| 8,048,030 B2 | 11/2011 | Conquergood et al. |
| 8,048,071 B2 | 11/2011 | Youssef et al. |
| 8,048,083 B2 | 11/2011 | Shadduck et al. |
| 8,052,661 B2 | 11/2011 | McGuckin, Jr. et al. |
| 8,062,290 B2 | 11/2011 | Buysse et al. |
| 8,066,702 B2 | 11/2011 | Rittman, III et al. |
| 8,066,712 B2 | 11/2011 | Truckai et al. |
| 8,070,753 B2 | 12/2011 | Truckai et al. |
| 8,082,043 B2 | 12/2011 | Sharkey et al. |
| 8,083,736 B2 | 12/2011 | McClurken et al. |
| 8,096,957 B2 | 1/2012 | Conquergood et al. |
| 8,100,896 B2 | 1/2012 | Podhajsky |
| 8,109,933 B2 | 2/2012 | Truckai et al. |
| 8,123,750 B2 | 2/2012 | Norton et al. |
| 8,123,756 B2 | 2/2012 | Miller et al. |
| 8,128,619 B2 | 3/2012 | Sharkey et al. |
| 8,128,633 B2 | 3/2012 | Linderman et al. |
| 8,162,933 B2 | 4/2012 | Francischelli et al. |
| 8,163,031 B2 | 4/2012 | Truckai et al. |
| 8,172,846 B2 | 5/2012 | Brunnett et al. |
| 8,182,477 B2 | 5/2012 | Orszulak et al. |
| 8,187,312 B2 | 5/2012 | Sharkey et al. |
| 8,192,424 B2 | 6/2012 | Woloszko et al. |
| 8,192,435 B2 | 6/2012 | Bleich et al. |
| 8,216,223 B2 | 7/2012 | Wham et al. |
| 8,226,697 B2 | 7/2012 | Sharkey et al. |
| 8,231,616 B2 | 7/2012 | McPherson et al. |
| 8,241,335 B2 | 8/2012 | Truckai et al. |
| 8,246,627 B2 | 8/2012 | Vanleeuwen et al. |
| 8,265,747 B2 | 9/2012 | Rittman, III et al. |
| 8,282,628 B2 | 10/2012 | Paul et al. |
| 8,292,882 B2 | 10/2012 | Danek et al. |
| 8,292,887 B2 | 10/2012 | Woloszko et al. |
| 8,323,277 B2 | 12/2012 | Vilims |
| 8,323,279 B2 | 12/2012 | Dahla et al. |
| 8,343,146 B2 | 1/2013 | Godara |
| 8,348,946 B2 | 1/2013 | McClurken et al. |
| 8,348,955 B2 | 1/2013 | Truckai et al. |
| 8,355,799 B2 | 1/2013 | Marion et al. |
| 8,361,063 B2 | 1/2013 | Godara |
| 8,361,067 B2 | 1/2013 | Pellegrino et al. |
| 8,406,886 B2 | 3/2013 | Gaunt et al. |
| 8,409,289 B2 | 4/2013 | Truckai et al. |
| 8,414,509 B2 | 4/2013 | Diederich et al. |
| 8,414,571 B2 | 4/2013 | Pellegrino et al. |
| 8,419,730 B2 | 4/2013 | Pellegrino et al. |
| 8,419,731 B2 | 4/2013 | Pellegrino et al. |
| 8,425,507 B2 | 4/2013 | Pellegrino et al. |
| 8,430,887 B2 | 4/2013 | Truckai et al. |
| 8,444,636 B2 | 5/2013 | Shadduck et al. |
| 8,444,640 B2 | 5/2013 | Demarais et al. |
| 8,454,594 B2 | 6/2013 | Demarais et al. |
| 8,460,382 B2 | 6/2013 | Helm et al. |
| 8,475,449 B2 | 7/2013 | Werneth et al. |
| 8,486,063 B2 | 7/2013 | Werneth et al. |
| 8,487,021 B2 | 7/2013 | Truckai et al. |
| 8,504,147 B2 | 8/2013 | Deem et al. |
| 8,505,545 B2 | 8/2013 | Conquergood et al. |
| 8,518,036 B2 | 8/2013 | Leung et al. |
| 8,523,871 B2 | 9/2013 | Truckai et al. |
| 8,535,309 B2 | 9/2013 | Pellegrino et al. |
| 8,540,723 B2 | 9/2013 | Shadduck |
| 8,556,910 B2 | 10/2013 | Truckai et al. |
| 8,556,911 B2 | 10/2013 | Mehta et al. |
| 8,560,062 B2 | 10/2013 | Ritman, III et al. |
| 8,562,593 B2 | 10/2013 | Falkenstein et al. |
| 8,562,607 B2 | 10/2013 | Truckai et al. |
| 8,562,620 B2 | 10/2013 | Truckai et al. |
| 8,579,903 B2 | 11/2013 | Carl |
| 8,585,694 B2 | 11/2013 | Amoah et al. |
| 8,591,507 B2 | 11/2013 | Kramer et al. |
| 8,597,301 B2 | 12/2013 | Mitchell |
| 8,603,083 B2 | 12/2013 | Stern et al. |
| 8,613,744 B2 | 12/2013 | Pellegrino et al. |
| 8,617,156 B2 | 12/2013 | Werneth et al. |
| 8,623,014 B2 | 1/2014 | Pellegrino et al. |
| 8,623,025 B2 | 1/2014 | Tan-Malecki et al. |
| 8,628,528 B2 | 1/2014 | Pellegrino et al. |
| 8,636,736 B2 | 1/2014 | Yates et al. |
| 8,644,941 B2 | 2/2014 | Rooney et al. |
| 8,657,814 B2 | 2/2014 | Werneth et al. |
| 8,663,266 B1 | 3/2014 | Obsuth |
| 8,672,934 B2 | 3/2014 | Benamou et al. |
| 8,676,309 B2 | 3/2014 | Deem et al. |
| 8,679,023 B2 | 3/2014 | Kobayashi et al. |
| 8,690,884 B2 | 4/2014 | Linderman et al. |
| 8,696,679 B2 | 4/2014 | Shadduck et al. |
| RE44,883 E | 5/2014 | Cha |
| 8,740,897 B2 | 6/2014 | Leung et al. |
| 8,747,359 B2 | 6/2014 | Pakter et al. |
| 8,747,398 B2 | 6/2014 | Behnke |
| 8,758,349 B2 | 6/2014 | Germain et al. |
| 8,764,761 B2 | 7/2014 | Truckai et al. |
| 8,771,265 B2 | 7/2014 | Truckai |
| 8,771,276 B2 | 7/2014 | Linderman |
| 8,774,913 B2 | 7/2014 | Demarais et al. |
| 8,774,924 B2 | 7/2014 | Weiner |
| 8,777,479 B2 | 7/2014 | Kwan et al. |
| 8,784,411 B2 | 7/2014 | Leuthardt et al. |
| 8,795,270 B2 | 8/2014 | Drake |
| 8,808,161 B2 | 8/2014 | Gregg et al. |
| 8,808,284 B2 | 8/2014 | Pellegrino et al. |
| 8,814,873 B2 | 8/2014 | Schaller et al. |
| 8,818,503 B2 | 8/2014 | Rittman, III |
| 8,821,488 B2 | 9/2014 | Stewart et al. |
| 8,845,631 B2 | 9/2014 | Werneth et al. |
| 8,864,759 B2 | 10/2014 | Godara et al. |

(56) References Cited

U.S. PATENT DOCUMENTS

| | | |
|---|---|---|
| 8,864,760 B2 | 10/2014 | Kramer et al. |
| 8,864,777 B2 | 10/2014 | Harrison et al. |
| 8,882,755 B2 | 11/2014 | Leung et al. |
| 8,882,759 B2 | 11/2014 | Manley et al. |
| 8,882,764 B2 | 11/2014 | Pellegrino et al. |
| 8,894,658 B2 | 11/2014 | Linderman et al. |
| 8,911,497 B2 | 12/2014 | Chavatte et al. |
| 8,915,949 B2 | 12/2014 | Diederich et al. |
| 8,926,620 B2 | 1/2015 | Chasmawala et al. |
| 8,932,300 B2 | 1/2015 | Shadduck et al. |
| 8,939,969 B2 | 1/2015 | Temelli et al. |
| 8,968,288 B2 | 3/2015 | Brannan |
| 8,989,859 B2 | 3/2015 | Deem et al. |
| 8,992,522 B2 | 3/2015 | Pellegrino et al. |
| 8,992,523 B2 | 3/2015 | Pellegrino et al. |
| 9,005,210 B2 | 4/2015 | Truckai et al. |
| 9,008,793 B1 | 4/2015 | Cosman, Sr. et al. |
| 9,017,325 B2 | 4/2015 | Pellegrino et al. |
| 9,023,038 B2 | 5/2015 | Pellegrino et al. |
| 9,028,488 B2 | 5/2015 | Goshayeshgar |
| 9,028,538 B2 | 5/2015 | Paul et al. |
| 9,039,701 B2 | 5/2015 | Pellegrino et al. |
| 9,044,245 B2 | 6/2015 | Condie et al. |
| 9,044,254 B2 | 6/2015 | Ladtkow et al. |
| 9,044,575 B2 | 6/2015 | Beasley et al. |
| 9,066,769 B2 | 6/2015 | Truckai et al. |
| 9,078,761 B2 | 7/2015 | Godara et al. |
| 9,095,359 B2 | 8/2015 | Robert et al. |
| 9,113,896 B2 | 8/2015 | Mulier et al. |
| 9,113,911 B2 | 8/2015 | Sherman |
| 9,113,925 B2 | 8/2015 | Smith et al. |
| 9,113,950 B2 | 8/2015 | Schultz et al. |
| 9,113,974 B2 | 8/2015 | Germain |
| 9,119,639 B2 | 9/2015 | Kuntz |
| 9,119,647 B2 | 9/2015 | Brannan |
| 9,119,650 B2 | 9/2015 | Brannan et al. |
| 9,125,671 B2 | 9/2015 | Germain et al. |
| 9,131,597 B2 | 9/2015 | Taft et al. |
| 9,149,652 B2 | 10/2015 | Wenz et al. |
| 9,151,680 B2 | 10/2015 | Brannan |
| 9,155,895 B2 | 10/2015 | Wacnik et al. |
| 9,161,735 B2 | 10/2015 | Bradford et al. |
| 9,161,797 B2 | 10/2015 | Truckai et al. |
| 9,161,798 B2 | 10/2015 | Truckai et al. |
| 9,161,805 B2 | 10/2015 | Isenberg |
| 9,161,809 B2 | 10/2015 | Germain et al. |
| 9,161,814 B2 | 10/2015 | Brannan et al. |
| 9,168,054 B2 | 10/2015 | Turner et al. |
| 9,168,078 B2 | 10/2015 | Linderman et al. |
| 9,168,085 B2 | 10/2015 | Juzkiw |
| 9,173,676 B2 | 11/2015 | Pellegrino et al. |
| 9,173,700 B2 | 11/2015 | Godara et al. |
| 9,179,970 B2 | 11/2015 | Utley et al. |
| 9,179,972 B2 | 11/2015 | Olson |
| 9,180,416 B2 | 11/2015 | Phan et al. |
| 9,186,197 B2 | 11/2015 | McKay |
| 9,192,308 B2 | 11/2015 | Brannan et al. |
| 9,192,397 B2 | 11/2015 | Sennett et al. |
| 9,198,684 B2 | 12/2015 | Arthur et al. |
| 9,216,053 B2 | 12/2015 | Godara et al. |
| 9,226,756 B2 | 1/2016 | Teisen et al. |
| 9,232,954 B2 | 1/2016 | Steiner et al. |
| 9,237,916 B2 | 1/2016 | Crainich et al. |
| 9,238,139 B2 | 1/2016 | Degiorgio et al. |
| 9,241,057 B2 | 1/2016 | Van Wyk et al. |
| 9,241,729 B2 | 1/2016 | Juntz et al. |
| 9,241,760 B2 | 1/2016 | Godara et al. |
| 9,247,970 B2 | 2/2016 | Teisen |
| 9,247,992 B2 | 2/2016 | Ladtkow et al. |
| 9,247,993 B2 | 2/2016 | Ladtkow et al. |
| 9,248,278 B2 | 2/2016 | Crosby et al. |
| 9,248,289 B2 | 2/2016 | Bennett et al. |
| 9,254,168 B2 | 2/2016 | Palanker |
| 9,254,386 B2 | 2/2016 | Lee et al. |
| 9,259,241 B2 | 2/2016 | Pellegrino et al. |
| 9,259,248 B2 | 2/2016 | Leuthardt et al. |
| 9,259,269 B2 | 2/2016 | Ladtkow et al. |
| 9,259,569 B2 | 2/2016 | Brounstein et al. |
| 9,259,577 B2 | 2/2016 | Kaula et al. |
| 9,265,522 B2 | 2/2016 | Pellegrino et al. |
| 9,265,557 B2 | 2/2016 | Sherman et al. |
| 9,277,969 B2 | 3/2016 | Brannan et al. |
| 9,282,979 B2 | 3/2016 | O'Neil et al. |
| 9,282,988 B2 | 3/2016 | Goshayeshgar |
| 9,283,015 B2 | 3/2016 | Tan-Malecki et al. |
| 9,289,607 B2 | 3/2016 | Su et al. |
| 9,295,517 B2 | 3/2016 | Peyman et al. |
| 9,295,841 B2 | 3/2016 | Fang et al. |
| 9,301,723 B2 | 4/2016 | Brannan et al. |
| 9,301,804 B2 | 4/2016 | Bonn |
| 9,302,117 B2 | 4/2016 | De Vincentiis |
| 9,308,036 B2 | 4/2016 | Robinson |
| 9,308,045 B2 | 4/2016 | Kim et al. |
| 9,314,252 B2 | 4/2016 | Schaller et al. |
| 9,314,613 B2 | 4/2016 | Mashiach |
| 9,314,618 B2 | 4/2016 | Imran et al. |
| 9,333,033 B2 | 5/2016 | Gliner |
| 9,333,144 B2 | 5/2016 | Baxter et al. |
| 9,333,339 B2 | 5/2016 | Weiner |
| 9,333,361 B2 | 5/2016 | Li et al. |
| 9,333,373 B2 | 5/2016 | Imran |
| 9,339,655 B2 | 5/2016 | Carbunaru |
| 9,345,530 B2 | 5/2016 | Ballakur et al. |
| 9,345,537 B2 | 5/2016 | Harrison et al. |
| 9,345,538 B2 | 5/2016 | Deem et al. |
| 9,351,739 B2 | 5/2016 | Mahoney et al. |
| 9,358,059 B2 | 6/2016 | Linderman et al. |
| 9,358,067 B2 | 6/2016 | Lee et al. |
| 9,358,396 B2 | 6/2016 | Holley |
| 9,364,242 B2 | 6/2016 | Tornier et al. |
| 9,364,286 B2 | 6/2016 | Werneth et al. |
| 9,370,348 B2 | 6/2016 | Tally et al. |
| 9,370,392 B2 | 6/2016 | Sharonov |
| 9,370,398 B2 | 6/2016 | Ladtkow et al. |
| 9,375,274 B2 | 6/2016 | Reid |
| 9,375,275 B2 | 6/2016 | Lee et al. |
| 9,375,278 B2 | 6/2016 | Robert et al. |
| 9,375,279 B2 | 6/2016 | Brannan |
| 9,375,283 B2 | 6/2016 | Arts et al. |
| 9,331,045 B2 | 7/2016 | Donner et al. |
| 9,381,024 B2 | 7/2016 | Globerman et al. |
| 9,381,050 B2 | 7/2016 | Lee et al. |
| 9,381,359 B2 | 7/2016 | Parramon et al. |
| 9,387,094 B2 | 7/2016 | Manrique et al. |
| 9,393,416 B2 | 7/2016 | Rooney et al. |
| 9,398,931 B2 | 7/2016 | Wittenberger et al. |
| 9,399,144 B2 | 7/2016 | Howard |
| 9,403,038 B2 | 8/2016 | Tyler |
| 9,409,023 B2 | 8/2016 | Burdick et al. |
| 9,414,884 B2 | 8/2016 | Faehndrich et al. |
| 9,421,064 B2 | 8/2016 | Pellegrino et al. |
| 9,421,123 B2 | 8/2016 | Lee et al. |
| 9,421,371 B2 | 8/2016 | Pless et al. |
| 9,421,378 B2 | 8/2016 | Lian et al. |
| 9,439,693 B2 | 9/2016 | Childs et al. |
| 9,439,721 B2 | 9/2016 | Werneth et al. |
| 9,445,859 B2 | 9/2016 | Pageard |
| 9,446,229 B2 | 9/2016 | Omar-Pasha |
| 9,446,235 B2 | 9/2016 | Su et al. |
| 9,452,286 B2 | 9/2016 | Cowan et al. |
| 9,456,836 B2 | 10/2016 | Boling et al. |
| 9,457,182 B2 | 10/2016 | Koop |
| 9,468,485 B2 | 10/2016 | Wittenberger et al. |
| 9,468,495 B2 | 10/2016 | Kunis et al. |
| 9,474,565 B2 | 10/2016 | Shikhman et al. |
| 9,474,906 B2 | 10/2016 | Sachs et al. |
| 9,480,485 B2 | 11/2016 | Aho et al. |
| 9,486,279 B2 | 11/2016 | Pellegrino et al. |
| 9,486,447 B2 | 11/2016 | Peterson et al. |
| 9,486,621 B2 | 11/2016 | Howard et al. |
| 9,492,657 B2 | 11/2016 | Gerber |
| 9,492,664 B2 | 11/2016 | Peterson |
| 9,504,372 B2 | 11/2016 | Kim |
| 9,504,481 B2 | 11/2016 | Germain et al. |

(56) References Cited

U.S. PATENT DOCUMENTS

| | | |
|---|---|---|
| 9,504,506 B2 | 11/2016 | Crainich et al. |
| 9,504,518 B2 | 11/2016 | Condie et al. |
| 9,504,530 B2 | 11/2016 | Hartmann et al. |
| 9,504,818 B2 | 11/2016 | Moffitt et al. |
| 9,511,229 B2 | 12/2016 | Bradley |
| 9,511,231 B1 | 12/2016 | Kent et al. |
| 9,513,761 B2 | 12/2016 | Shikhman et al. |
| 9,517,077 B2 | 12/2016 | Blain et al. |
| 9,517,200 B2 | 12/2016 | Bieier |
| 9,526,507 B2 | 12/2016 | Germain |
| 9,526,551 B2 | 12/2016 | Linderman |
| 9,526,559 B2 | 12/2016 | Benamou et al. |
| 9,532,828 B2 | 1/2017 | Condie et al. |
| 9,549,772 B2 | 1/2017 | Carl |
| 9,550,041 B2 | 1/2017 | Bedell |
| 9,555,037 B2 | 1/2017 | Podhajsky |
| 9,556,101 B2 | 1/2017 | Robertson et al. |
| 9,556,449 B2 | 1/2017 | Basu et al. |
| 9,566,449 B2 | 2/2017 | Perryman et al. |
| 9,572,976 B2 | 2/2017 | Howard et al. |
| 9,572,986 B2 | 2/2017 | Moffitt |
| 9,579,127 B2 | 2/2017 | Kostuik et al. |
| 9,579,518 B2 | 2/2017 | Gertner |
| RE46,346 E | 3/2017 | Sommer et al. |
| 9,597,091 B2 | 3/2017 | Bromer |
| 9,597,148 B2 | 3/2017 | Olson |
| RE46,356 E | 4/2017 | Pellegrino et al. |
| 9,610,083 B2 | 4/2017 | Kuntz |
| 9,610,117 B2 | 4/2017 | Germain |
| 9,636,175 B2 | 5/2017 | Stern et al. |
| 9,642,629 B2 | 5/2017 | Griffiths et al. |
| 9,649,116 B2 | 5/2017 | Germain |
| 9,681,889 B1 * | 6/2017 | Greenhalgh ....... A61B 17/3472 |
| 9,687,255 B2 | 6/2017 | Sennett et al. |
| 9,724,107 B2 | 8/2017 | Pellegrino et al. |
| 9,724,151 B2 | 8/2017 | Edidin |
| 9,730,707 B2 | 8/2017 | Sasaki et al. |
| 9,743,854 B2 | 8/2017 | Stewart et al. |
| 9,743,938 B2 | 8/2017 | Germain et al. |
| 9,750,560 B2 | 9/2017 | Ballakur et al. |
| 9,757,193 B2 | 9/2017 | Zarins et al. |
| 9,770,280 B2 | 9/2017 | Diederich et al. |
| 9,775,627 B2 | 10/2017 | Patel et al. |
| 9,782,221 B2 | 10/2017 | Srinivasan |
| 9,795,802 B2 | 10/2017 | Mohamed et al. |
| 9,814,514 B2 | 11/2017 | Shelton, IV et al. |
| 9,844,406 B2 | 12/2017 | Edwards et al. |
| 9,848,944 B2 | 12/2017 | Sutton et al. |
| 9,872,687 B2 | 1/2018 | Tornier et al. |
| 9,872,691 B2 | 1/2018 | Griffiths et al. |
| 9,877,707 B2 | 1/2018 | Godara et al. |
| 9,913,675 B2 | 3/2018 | Germain |
| 10,028,753 B2 | 7/2018 | Pellegrino et al. |
| 10,028,784 B2 | 7/2018 | Kramer et al. |
| 10,052,152 B2 | 8/2018 | Tegg et al. |
| 10,111,674 B2 | 10/2018 | Crainich et al. |
| 10,111,704 B2 | 10/2018 | Pellegrino et al. |
| 10,123,809 B2 | 11/2018 | Germain |
| 10,245,092 B2 | 4/2019 | Germain |
| 10,265,099 B2 | 4/2019 | Pellegrino et al. |
| 10,272,271 B2 | 4/2019 | Diederich et al. |
| 10,232,719 B2 | 5/2019 | Burger et al. |
| 10,292,716 B2 | 5/2019 | Aho et al. |
| 10,299,805 B2 | 5/2019 | Germain et al. |
| 10,327,841 B2 | 6/2019 | Germain |
| 10,357,258 B2 | 7/2019 | Patel et al. |
| 10,383,641 B2 | 8/2019 | LeRoy et al. |
| 10,390,877 B2 | 8/2019 | Heggeness et al. |
| 10,441,295 B2 | 10/2019 | Brockman et al. |
| 10,448,995 B2 | 10/2019 | Olson |
| 10,456,187 B2 | 10/2019 | Edidin |
| 10,463,380 B2 | 11/2019 | Purdy et al. |
| 10,463,423 B2 | 11/2019 | Sutton et al. |
| 10,470,781 B2 | 11/2019 | Purdy et al. |
| 10,478,241 B2 | 11/2019 | Purdy et al. |
| 10,478,246 B2 | 11/2019 | Pellegrino et al. |
| 10,493,247 B2 | 12/2019 | Goshayeshgar |
| 10,499,960 B2 | 12/2019 | Sinnott et al. |
| 10,517,611 B2 | 12/2019 | Patel et al. |
| 10,524,805 B2 | 1/2020 | Zilberman et al. |
| 10,588,691 B2 | 3/2020 | Pellegrino et al. |
| 10,589,131 B2 | 3/2020 | Diederich et al. |
| 10,603,522 B2 | 3/2020 | Diederich et al. |
| 10,624,652 B2 | 4/2020 | Germain et al. |
| 10,660,656 B2 | 5/2020 | Purdy et al. |
| 10,898,254 B2 | 1/2021 | Diederich et al. |
| 10,905,440 B2 | 2/2021 | Pellegrino et al. |
| RE48,460 E | 3/2021 | Pellegrino et al. |
| 11,007,010 B2 | 5/2021 | Donovan et al. |
| 11,052,267 B2 | 7/2021 | Diederich et al. |
| 11,065,046 B2 | 7/2021 | Edidin |
| 2001/0001314 A1 | 5/2001 | Davison et al. |
| 2001/0001811 A1 | 5/2001 | Burney et al. |
| 2001/0020167 A1 | 9/2001 | Woloszko et al. |
| 2001/0023348 A1 | 9/2001 | Ashley et al. |
| 2001/0025176 A1 | 9/2001 | Ellsberry et al. |
| 2001/0025177 A1 | 9/2001 | Woloszko et al. |
| 2001/0027295 A1 | 10/2001 | Dulak et al. |
| 2001/0029370 A1 | 10/2001 | Hovda et al. |
| 2001/0029373 A1 | 10/2001 | Baker et al. |
| 2001/0029393 A1 | 10/2001 | Tierney et al. |
| 2001/0032001 A1 | 10/2001 | Ricart et al. |
| 2001/0047167 A1 | 11/2001 | Heggeness |
| 2001/0049522 A1 | 12/2001 | Eggers et al. |
| 2001/0049527 A1 | 12/2001 | Cragg |
| 2001/0051802 A1 | 12/2001 | Woloszko et al. |
| 2001/0053885 A1 | 12/2001 | Gielen et al. |
| 2001/0056280 A1 | 12/2001 | Underwood et al. |
| 2002/0016600 A1 | 2/2002 | Cosman |
| 2002/0019626 A1 | 2/2002 | Sharkey et al. |
| 2002/0026186 A1 | 2/2002 | Woloszko et al. |
| 2002/0049438 A1 | 4/2002 | Sharkey et al. |
| 2002/0095144 A1 | 4/2002 | Carl |
| 2002/0052600 A1 | 5/2002 | Davison et al. |
| 2002/0068930 A1 | 6/2002 | Tasto et al. |
| 2002/0095151 A1 | 7/2002 | Dahla et al. |
| 2002/0095152 A1 | 7/2002 | Ciarrocca et al. |
| 2002/0099366 A1 | 7/2002 | Dahla et al. |
| 2002/0111661 A1 | 8/2002 | Cross et al. |
| 2002/0115945 A1 | 8/2002 | D'Luzansky et al. |
| 2002/0120259 A1 | 8/2002 | Lettice et al. |
| 2002/0133148 A1 | 9/2002 | Daniel et al. |
| 2002/0147444 A1 | 10/2002 | Shah et al. |
| 2002/0151885 A1 | 10/2002 | Underwood et al. |
| 2002/0165532 A1 | 11/2002 | Hill et al. |
| 2002/0188284 A1 | 12/2002 | To et al. |
| 2002/0188290 A1 | 12/2002 | Sharkey et al. |
| 2002/0193708 A1 | 12/2002 | Horzewski et al. |
| 2002/0193769 A1 | 12/2002 | Underwood et al. |
| 2003/0009164 A1 | 1/2003 | Woloszko et al. |
| 2003/0014047 A1 | 1/2003 | Woloszko et al. |
| 2003/0014088 A1 | 1/2003 | Fang et al. |
| 2003/0028147 A1 | 2/2003 | Aves et al. |
| 2003/0028189 A1 | 2/2003 | Woloszko et al. |
| 2003/0040742 A1 | 2/2003 | Underwood et al. |
| 2003/0055418 A1 | 3/2003 | Tasto et al. |
| 2003/0069569 A1 | 4/2003 | Burdette et al. |
| 2003/0083592 A1 | 5/2003 | Faciszewski |
| 2003/0084907 A1 | 5/2003 | Pacek et al. |
| 2003/0097126 A1 | 5/2003 | Woloszko et al. |
| 2003/0097129 A1 | 5/2003 | Davison et al. |
| 2003/0130655 A1 | 7/2003 | Woloszko et al. |
| 2003/0139652 A1 | 7/2003 | Kang et al. |
| 2003/0158545 A1 | 8/2003 | Hovda et al. |
| 2003/0181963 A1 | 9/2003 | Pellegrino et al. |
| 2003/0208194 A1 | 11/2003 | Hovda et al. |
| 2003/0216725 A1 | 11/2003 | Woloszko et al. |
| 2003/0216726 A1 | 11/2003 | Eggers et al. |
| 2003/0225364 A1 | 12/2003 | Kraft |
| 2004/0006339 A1 | 1/2004 | Underwood et al. |
| 2004/0015163 A1 | 1/2004 | Buysse et al. |
| 2004/0024399 A1 | 2/2004 | Sharps et al. |
| 2004/0054366 A1 | 3/2004 | Davison et al. |
| 2004/0064023 A1 | 4/2004 | Thomas et al. |

(56) References Cited

U.S. PATENT DOCUMENTS

| | | |
|---|---|---|
| 2004/0064136 A1 | 4/2004 | Crombie et al. |
| 2004/0064137 A1 | 4/2004 | Pellegrino et al. |
| 2004/0068242 A1 | 4/2004 | McGuckin, Jr. |
| 2004/0082942 A1 | 4/2004 | Katzman |
| 2004/0082946 A1 | 4/2004 | Malis et al. |
| 2004/0087937 A1 | 5/2004 | Eggers et al. |
| 2004/0111087 A1 | 6/2004 | Stern et al. |
| 2004/0116922 A1 | 6/2004 | Hovda et al. |
| 2004/0120891 A1 | 6/2004 | Hill et al. |
| 2004/0133124 A1 | 7/2004 | Bates et al. |
| 2004/0162559 A1 | 8/2004 | Arramon |
| 2004/0186544 A1 | 9/2004 | King |
| 2004/0193151 A1 | 9/2004 | To et al. |
| 2004/0220577 A1 | 11/2004 | Cragg et al. |
| 2004/0225228 A1 | 11/2004 | Ferree |
| 2004/0230190 A1 | 11/2004 | Dahla et al. |
| 2004/0267269 A1 | 12/2004 | Middleton et al. |
| 2005/0004634 A1 | 1/2005 | Ricart et al. |
| 2005/0010095 A1 | 1/2005 | Stewart et al. |
| 2005/0010203 A1 | 1/2005 | Edwards et al. |
| 2005/0010205 A1 | 1/2005 | Hovda et al. |
| 2005/0043737 A1 | 2/2005 | Reiley et al. |
| 2005/0055096 A1 | 3/2005 | Serhan et al. |
| 2005/0124989 A1 | 6/2005 | Suddaby |
| 2005/0177209 A1 | 8/2005 | Leung et al. |
| 2005/0177210 A1 | 8/2005 | Leung et al. |
| 2005/0177211 A1 | 8/2005 | Leung et al. |
| 2005/0182417 A1 | 8/2005 | Pagano |
| 2005/0192564 A1 | 9/2005 | Cosman et al. |
| 2005/0209659 A1 | 9/2005 | Pellegrino et al. |
| 2005/0234445 A1 | 10/2005 | Conquergood et al. |
| 2005/0261754 A1 | 11/2005 | Woloszko |
| 2005/0267552 A1 | 12/2005 | Conquergood et al. |
| 2005/0278007 A1 | 12/2005 | Godara |
| 2005/0283148 A1 | 12/2005 | Janssen et al. |
| 2006/0004369 A1 | 1/2006 | Patel et al. |
| 2006/0052743 A1 | 3/2006 | Reynolds |
| 2006/0064101 A1 | 3/2006 | Arramon |
| 2006/0095026 A1 | 5/2006 | Ricart et al. |
| 2006/0095028 A1 | 5/2006 | Bleich |
| 2006/0106375 A1 | 5/2006 | Werneth et al. |
| 2006/0106376 A1 | 5/2006 | Godara et al. |
| 2006/0122458 A1 | 6/2006 | Bleich |
| 2006/0129101 A1 | 6/2006 | McGuckin |
| 2006/0173670 A1 | 8/2006 | Woloszko et al. |
| 2006/0178670 A1 | 8/2006 | Woloszko et al. |
| 2006/0200121 A1 | 9/2006 | Mowery |
| 2006/0206128 A1 | 9/2006 | Conquergood et al. |
| 2006/0206129 A1 | 9/2006 | Conquergood et al. |
| 2006/0206130 A1 | 9/2006 | Conquergood et al. |
| 2006/0206132 A1 | 9/2006 | Conquergood et al. |
| 2006/0206133 A1 | 9/2006 | Conquergood et al. |
| 2006/0206134 A1 | 9/2006 | Conquergood et al. |
| 2006/0206166 A1 | 9/2006 | Weiner |
| 2006/0217736 A1 | 9/2006 | Kaneko et al. |
| 2006/0229625 A1 | 10/2006 | Truckai et al. |
| 2006/0247746 A1 | 11/2006 | Danek et al. |
| 2006/0253117 A1 | 11/2006 | Hovda et al. |
| 2006/0259026 A1 | 11/2006 | Godara et al. |
| 2006/0264957 A1 | 11/2006 | Cragg et al. |
| 2006/0264965 A1 | 11/2006 | Shadduck et al. |
| 2006/0265014 A1 | 11/2006 | Demarais et al. |
| 2006/0276749 A1 | 12/2006 | Selmon et al. |
| 2006/0287649 A1 | 12/2006 | Ormsby et al. |
| 2007/0027449 A1 | 2/2007 | Godara et al. |
| 2007/0055316 A1 | 3/2007 | Godara et al. |
| 2007/0066987 A1* | 3/2007 | Scanlan, Jr. ........ A61B 17/3472 606/184 |
| 2007/0074719 A1 | 4/2007 | Danek et al. |
| 2007/0118142 A1 | 5/2007 | Krueger et al. |
| 2007/0129715 A1 | 6/2007 | Eggers et al. |
| 2007/0142791 A1 | 6/2007 | Yeung et al. |
| 2007/0142842 A1 | 6/2007 | Krueger et al. |
| 2007/0149966 A1 | 6/2007 | Dahla et al. |
| 2007/0179497 A1 | 8/2007 | Eggers et al. |
| 2007/0185231 A1 | 8/2007 | Liu et al. |
| 2007/0213584 A1 | 9/2007 | Kim et al. |
| 2007/0213735 A1 | 9/2007 | Saadat et al. |
| 2007/0260237 A1 | 11/2007 | Sutton et al. |
| 2008/0004621 A1 | 1/2008 | Dahla et al. |
| 2008/0004675 A1 | 1/2008 | King et al. |
| 2008/0009847 A1 | 1/2008 | Ricart et al. |
| 2008/0021447 A1 | 1/2008 | Davison et al. |
| 2008/0021463 A1 | 1/2008 | Georgy |
| 2008/0058707 A1 | 3/2008 | Ashley et al. |
| 2008/0065062 A1 | 3/2008 | Leung et al. |
| 2008/0091207 A1 | 4/2008 | Truckai et al. |
| 2008/0114364 A1 | 5/2008 | Goldin et al. |
| 2008/0119844 A1 | 5/2008 | Woloszko et al. |
| 2008/0119846 A1 | 5/2008 | Rioux |
| 2008/0132890 A1 | 6/2008 | Woloszko et al. |
| 2008/0161804 A1 | 7/2008 | Rioux et al. |
| 2008/0275458 A1 | 11/2008 | Bleich et al. |
| 2008/0281322 A1 | 11/2008 | Sherman et al. |
| 2008/0294166 A1 | 11/2008 | Goldin et al. |
| 2008/0294167 A1 | 11/2008 | Schumacher et al. |
| 2009/0030308 A1 | 1/2009 | Bradford et al. |
| 2009/0054951 A1 | 2/2009 | Leuthardt et al. |
| 2009/0069807 A1 | 3/2009 | Eggers et al. |
| 2009/0076520 A1* | 3/2009 | Choi ................ A61B 17/8819 606/108 |
| 2009/0105775 A1 | 4/2009 | Mitchell et al. |
| 2009/0112278 A1 | 4/2009 | Wingeier et al. |
| 2009/0118731 A1 | 5/2009 | Young et al. |
| 2009/0131867 A1 | 5/2009 | Liu et al. |
| 2009/0131886 A1 | 5/2009 | Liu et al. |
| 2009/0149878 A1 | 6/2009 | Truckai et al. |
| 2009/0204192 A1 | 8/2009 | Carlton et al. |
| 2009/0222053 A1 | 9/2009 | Gaunt et al. |
| 2009/0312764 A1 | 12/2009 | Marino |
| 2010/0010392 A1 | 1/2010 | Skelton et al. |
| 2010/0016929 A1 | 1/2010 | Prochazka |
| 2010/0023006 A1 | 1/2010 | Ellman |
| 2010/0023065 A1 | 1/2010 | Welch et al. |
| 2010/0082033 A1 | 4/2010 | Germain |
| 2010/0094269 A1 | 4/2010 | Pellegrino et al. |
| 2010/0114098 A1 | 5/2010 | Carl |
| 2010/0145424 A1 | 6/2010 | Podhajsky et al. |
| 2010/0179556 A1 | 7/2010 | Scribner et al. |
| 2010/0185082 A1 | 7/2010 | Chandran et al. |
| 2010/0185161 A1 | 7/2010 | Pellegrino et al. |
| 2010/0211076 A1 | 8/2010 | Germain et al. |
| 2010/0222777 A1 | 9/2010 | Sutton et al. |
| 2010/0261989 A1 | 10/2010 | Boseck et al. |
| 2010/0261990 A1 | 10/2010 | Gillis et al. |
| 2010/0298737 A1 | 11/2010 | Koehler |
| 2010/0298832 A1 | 11/2010 | Lau et al. |
| 2010/0324506 A1 | 12/2010 | Pellegrino et al. |
| 2011/0022133 A1 | 1/2011 | Diederich et al. |
| 2011/0034884 A9 | 2/2011 | Pellegrino et al. |
| 2011/0040362 A1 | 2/2011 | Godara et al. |
| 2011/0077628 A1 | 3/2011 | Hoey et al. |
| 2011/0087314 A1 | 4/2011 | Diederich et al. |
| 2011/0118735 A1 | 5/2011 | Abou-Marie et al. |
| 2011/0130751 A1 | 6/2011 | Malis et al. |
| 2011/0196361 A1 | 8/2011 | Vilims |
| 2011/0206260 A1 | 8/2011 | Bergmans et al. |
| 2011/0264098 A1 | 10/2011 | Cobbs |
| 2011/0276001 A1 | 11/2011 | Schultz et al. |
| 2011/0296261 A1 | 12/2011 | Germain |
| 2011/0319765 A1 | 12/2011 | Gertner et al. |
| 2012/0029420 A1 | 2/2012 | Vilims |
| 2012/0116266 A1 | 5/2012 | House et al. |
| 2012/0136346 A1 | 5/2012 | Condie et al. |
| 2012/0136348 A1 | 5/2012 | Condie et al. |
| 2012/0172858 A1 | 7/2012 | Harrison et al. |
| 2012/0172859 A1 | 7/2012 | Condie et al. |
| 2012/0191095 A1 | 7/2012 | Burger et al. |
| 2012/0196251 A1 | 8/2012 | Taft et al. |
| 2012/0197344 A1 | 8/2012 | Taft et al. |
| 2012/0203219 A1 | 8/2012 | Evans et al. |
| 2012/0226273 A1 | 9/2012 | Nguyen et al. |
| 2012/0239050 A1 | 9/2012 | Linderman |
| 2012/0265186 A1 | 10/2012 | Burger et al. |

(56) References Cited

U.S. PATENT DOCUMENTS

| | | |
|---|---|---|
| 2012/0330180 A1 | 12/2012 | Pellegrino et al. |
| 2012/0330300 A1 | 12/2012 | Pellegrino et al. |
| 2012/0330301 A1 | 12/2012 | Pellegrino et al. |
| 2013/0006232 A1 | 1/2013 | Pellegrino et al. |
| 2013/0006233 A1 | 1/2013 | Pellegrino et al. |
| 2013/0012933 A1 | 1/2013 | Pellegrino et al. |
| 2013/0012935 A1 | 1/2013 | Pellegrino et al. |
| 2013/0012936 A1 | 1/2013 | Pellegrino et al. |
| 2013/0012951 A1 | 1/2013 | Linderman |
| 2013/0060244 A1 | 3/2013 | Godara et al. |
| 2013/0079810 A1 | 3/2013 | Isenberg |
| 2013/0103022 A1 | 4/2013 | Sutton et al. |
| 2013/0197508 A1 | 8/2013 | Shikhman et al. |
| 2013/0231654 A1 | 9/2013 | Germain |
| 2013/0237979 A1 | 9/2013 | Shikhman et al. |
| 2013/0261507 A1 | 10/2013 | Diederich et al. |
| 2013/0296767 A1 | 11/2013 | Zarins et al. |
| 2013/0324993 A1 | 12/2013 | McCarthey et al. |
| 2013/0324994 A1 | 12/2013 | Pellegrino et al. |
| 2013/0324996 A1 | 12/2013 | Pellegrino et al. |
| 2013/0324997 A1 | 12/2013 | Pellegrino et al. |
| 2013/0331840 A1* | 12/2013 | Teisen ............... A61B 17/1671 606/80 |
| 2013/0345765 A1 | 12/2013 | Brockman et al. |
| 2014/0031715 A1 | 1/2014 | Sherar et al. |
| 2014/0039500 A1 | 2/2014 | Pellegrino et al. |
| 2014/0046245 A1 | 2/2014 | Comacchia |
| 2014/0046328 A1 | 2/2014 | Schumacher et al. |
| 2014/0066913 A1 | 3/2014 | Sherman |
| 2014/0088575 A1 | 3/2014 | Loeb |
| 2014/0148801 A1 | 5/2014 | Asher et al. |
| 2014/0148805 A1 | 5/2014 | Stewart et al. |
| 2014/0171942 A1 | 6/2014 | Werneth et al. |
| 2014/0194887 A1 | 7/2014 | Shenoy |
| 2014/0221967 A1 | 8/2014 | Childs et al. |
| 2014/0236137 A1 | 8/2014 | Tran et al. |
| 2014/0236144 A1 | 8/2014 | Krueger et al. |
| 2014/0243823 A1 | 8/2014 | Godara et al. |
| 2014/0243943 A1 | 8/2014 | Rao et al. |
| 2014/0257265 A1 | 9/2014 | Godara et al. |
| 2014/0271717 A1 | 9/2014 | Goshayeshgar et al. |
| 2014/0276728 A1 | 9/2014 | Goshayeshgar et al. |
| 2014/0276744 A1 | 9/2014 | Arthur et al. |
| 2014/0283546 A1 | 9/2014 | Sherman et al. |
| 2014/0288544 A1 | 9/2014 | Diederich et al. |
| 2014/0296850 A1 | 10/2014 | Condie et al. |
| 2014/0303610 A1 | 10/2014 | McCarthy et al. |
| 2014/0303614 A1 | 10/2014 | McCarthy et al. |
| 2014/0316405 A1 | 10/2014 | Pellegrino et al. |
| 2014/0316413 A1 | 10/2014 | Burger et al. |
| 2014/0324051 A1 | 10/2014 | Pellegrino et al. |
| 2014/0330332 A1 | 11/2014 | Danek et al. |
| 2014/0336630 A1 | 11/2014 | Woloszko et al. |
| 2014/0336667 A1 | 11/2014 | Pellegrino et al. |
| 2014/0364842 A1 | 12/2014 | Werneth et al. |
| 2014/0371740 A1 | 12/2014 | Germain et al. |
| 2015/0005614 A1 | 1/2015 | Heggeness et al. |
| 2015/0005767 A1 | 1/2015 | Werneth et al. |
| 2015/0045783 A1 | 2/2015 | Edidin |
| 2015/0057658 A1 | 2/2015 | Sutton et al. |
| 2015/0065945 A1 | 3/2015 | Zarins et al. |
| 2015/0073515 A1 | 3/2015 | Turovskiy et al. |
| 2015/0105701 A1 | 4/2015 | Mayer et al. |
| 2015/0141876 A1 | 5/2015 | Diederich et al. |
| 2015/0157402 A1 | 6/2015 | Kunis et al. |
| 2015/0164546 A1 | 6/2015 | Pellegrino et al. |
| 2015/0196358 A1 | 7/2015 | Goshayeshgar |
| 2015/0216588 A1 | 8/2015 | Deem et al. |
| 2015/0231417 A1 | 8/2015 | Metcalf et al. |
| 2015/0272655 A1 | 10/2015 | Condie et al. |
| 2015/0273208 A1* | 10/2015 | Hamilton ............... A61B 17/34 606/129 |
| 2015/0297246 A1 | 10/2015 | Patel et al. |
| 2015/0297282 A1 | 10/2015 | Cadouri |
| 2015/0320480 A1 | 11/2015 | Cosman, Jr. et al. |
| 2015/0335349 A1 | 11/2015 | Pellegrino et al. |
| 2015/0335382 A1 | 11/2015 | Pellegrino et al. |
| 2015/0342619 A1 | 12/2015 | Weitzman |
| 2015/0342660 A1 | 12/2015 | Nash |
| 2015/0342670 A1 | 12/2015 | Pellegrino et al. |
| 2015/0359586 A1 | 12/2015 | Heggeness |
| 2015/0374432 A1 | 12/2015 | Godara et al. |
| 2015/0374992 A1 | 12/2015 | Crosby et al. |
| 2015/0374995 A1 | 12/2015 | Foreman et al. |
| 2016/0000601 A1 | 1/2016 | Burger et al. |
| 2016/0001096 A1 | 1/2016 | Mishelevich |
| 2016/0002627 A1 | 1/2016 | Bennett et al. |
| 2016/0008593 A1 | 1/2016 | Cairns |
| 2016/0008618 A1 | 1/2016 | Omar-Pasha |
| 2016/0008628 A1 | 1/2016 | Morries et al. |
| 2016/0016012 A1 | 1/2016 | Youn et al. |
| 2016/0022988 A1 | 1/2016 | Thieme et al. |
| 2016/0022994 A1 | 1/2016 | Moffitt et al. |
| 2016/0024208 A1 | 1/2016 | MacDonald et al. |
| 2016/0029930 A1 | 2/2016 | Plumley et al. |
| 2016/0030276 A1 | 2/2016 | Spanyer |
| 2016/0030408 A1 | 2/2016 | Levin |
| 2016/0030748 A1 | 2/2016 | Edgerton et al. |
| 2016/0030765 A1 | 2/2016 | Towne et al. |
| 2016/0045207 A1 | 2/2016 | Kovacs et al. |
| 2016/0045256 A1 | 2/2016 | Godara et al. |
| 2016/0051831 A1 | 2/2016 | Lundmark et al. |
| 2016/0059007 A1 | 3/2016 | Koop |
| 2016/0074068 A1 | 3/2016 | Patwardhan |
| 2016/0074133 A1 | 3/2016 | Shikhman et al. |
| 2016/0074279 A1 | 3/2016 | Shin |
| 2016/0074661 A1 | 3/2016 | Lipani |
| 2016/0081716 A1 | 3/2016 | Boling et al. |
| 2016/0081810 A1 | 3/2016 | Reiley et al. |
| 2016/0095721 A1 | 4/2016 | Schell et al. |
| 2016/0106443 A1 | 4/2016 | Kuntz et al. |
| 2016/0106985 A1 | 4/2016 | Zhu |
| 2016/0106994 A1 | 4/2016 | Crosby et al. |
| 2016/0113704 A1 | 4/2016 | Godara et al. |
| 2016/0115173 A1 | 4/2016 | Bois et al. |
| 2016/0136310 A1 | 5/2016 | Bradford et al. |
| 2016/0144182 A1 | 5/2016 | Bennett et al. |
| 2016/0144187 A1 | 5/2016 | Caparso et al. |
| 2016/0158551 A1 | 6/2016 | Kent et al. |
| 2016/0166302 A1 | 6/2016 | Tan-Malecki et al. |
| 2016/0166835 A1 | 6/2016 | De Ridder |
| 2016/0175586 A1 | 6/2016 | Edgerton et al. |
| 2016/0199097 A1 | 7/2016 | Linderman et al. |
| 2016/0199117 A1 | 7/2016 | Druma |
| 2016/0213927 A1 | 7/2016 | McGee et al. |
| 2016/0220317 A1 | 8/2016 | Shlkhman et al. |
| 2016/0220393 A1 | 8/2016 | Slivka et al. |
| 2016/0220638 A1 | 8/2016 | Dony et al. |
| 2016/0220672 A1 | 8/2016 | Chalasani et al. |
| 2016/0228131 A1 | 8/2016 | Brockman et al. |
| 2016/0228696 A1 | 8/2016 | Imran et al. |
| 2016/0235471 A1 | 8/2016 | Godara et al. |
| 2016/0235474 A1 | 8/2016 | Prisco et al. |
| 2016/0243353 A1 | 8/2016 | Ahmed |
| 2016/0246944 A1 | 8/2016 | Jain et al. |
| 2016/0250469 A1 | 9/2016 | Kim et al. |
| 2016/0250472 A1 | 9/2016 | Carbunaru |
| 2016/0262830 A1 | 9/2016 | Werneth et al. |
| 2016/0262904 A1 | 9/2016 | Schaller et al. |
| 2016/0271405 A1 | 9/2016 | Angara et al. |
| 2016/0278791 A1 | 9/2016 | Pellegrino et al. |
| 2016/0278846 A1 | 9/2016 | Harrison et al. |
| 2016/0278861 A1 | 9/2016 | Ko |
| 2016/0279190 A1 | 9/2016 | Watts et al. |
| 2016/0279408 A1 | 9/2016 | Grigsby et al. |
| 2016/0279411 A1 | 9/2016 | Rooney et al. |
| 2016/0279441 A1 | 9/2016 | Imran |
| 2016/0302925 A1 | 10/2016 | Keogh et al. |
| 2016/0302936 A1 | 10/2016 | Billon et al. |
| 2016/0310739 A1 | 10/2016 | Burdick et al. |
| 2016/0317053 A1 | 11/2016 | Srivastava |
| 2016/0317211 A1 | 11/2016 | Harrison et al. |
| 2016/0317621 A1 | 11/2016 | Bright |
| 2016/0324541 A1 | 11/2016 | Pellegrino et al. |

(56) References Cited

U.S. PATENT DOCUMENTS

| | | |
|---|---|---|
| 2016/0324677 A1 | 11/2016 | Hyde et al. |
| 2016/0325100 A1 | 11/2016 | Lian et al. |
| 2016/0339251 A1 | 11/2016 | Kent et al. |
| 2016/0354093 A1 | 12/2016 | Pellegrino et al. |
| 2016/0354233 A1 | 12/2016 | Sansone et al. |
| 2016/0367797 A1 | 12/2016 | Eckermann |
| 2016/0367823 A1 | 12/2016 | Cowan et al. |
| 2016/0375259 A1 | 12/2016 | Davis et al. |
| 2017/0000501 A1 | 1/2017 | Aho et al. |
| 2017/0001026 A1 | 1/2017 | Schwarz et al. |
| 2017/0007277 A1 | 1/2017 | Drapeau et al. |
| 2017/0014169 A1 | 1/2017 | Dean et al. |
| 2017/0027618 A1 | 2/2017 | Lee et al. |
| 2017/0028198 A1 | 2/2017 | Degiorgio et al. |
| 2017/0028201 A1 | 2/2017 | Howard |
| 2017/0035483 A1 | 2/2017 | Crainich et al. |
| 2017/0036009 A1 | 2/2017 | Hughes et al. |
| 2017/0036025 A1 | 2/2017 | Sachs et al. |
| 2017/0036033 A9 | 2/2017 | Perryman et al. |
| 2017/0042834 A1 | 2/2017 | Westphal et al. |
| 2017/0049500 A1 | 2/2017 | Shikhman et al. |
| 2017/0049503 A1 | 2/2017 | Cosman |
| 2017/0049507 A1 | 2/2017 | Cosman |
| 2017/0049513 A1 | 2/2017 | Cosman |
| 2017/0050017 A1 | 2/2017 | Cosman |
| 2017/0050021 A1 | 2/2017 | Cosman |
| 2017/0050024 A1 | 2/2017 | Bhadra et al. |
| 2017/0056028 A1 | 3/2017 | Germain et al. |
| 2017/0065329 A1 | 3/2017 | Benamou et al. |
| 2017/0112507 A1 | 4/2017 | Crainich et al. |
| 2017/0119461 A1 | 5/2017 | Godara et al. |
| 2017/0128080 A1 | 5/2017 | Torrie |
| 2017/0128112 A1 | 5/2017 | Germain |
| 2017/0135742 A1 | 5/2017 | Lee et al. |
| 2017/0164998 A1 | 6/2017 | Klimovitch |
| 2017/0172650 A1 | 6/2017 | Germain |
| 2017/0181788 A1 | 6/2017 | Dastjerdi et al. |
| 2017/0202613 A1 | 7/2017 | Pellegrino et al. |
| 2017/0238943 A1 | 8/2017 | Sennett et al. |
| 2017/0266419 A1 | 9/2017 | Goshayeshgar |
| 2017/0303983 A1 | 10/2017 | Linderman et al. |
| 2017/0312007 A1 | 11/2017 | Harlev et al. |
| 2017/0333052 A1 | 11/2017 | Ding et al. |
| 2018/0021048 A1 | 1/2018 | Pellegrino et al. |
| 2018/0042656 A1 | 2/2018 | Edidin |
| 2018/0055539 A1 | 3/2018 | Pellegrino |
| 2018/0103964 A1 | 4/2018 | Patel et al. |
| 2018/0153604 A1 | 6/2018 | Ayvazyan et al. |
| 2018/0161047 A1 | 6/2018 | Purdy et al. |
| 2018/0193088 A1 | 7/2018 | Sutton et al. |
| 2019/0029698 A1 | 1/2019 | Pellegrino et al. |
| 2019/0038296 A1 | 2/2019 | Pellegrino |
| 2019/0038343 A1 | 2/2019 | Sutton et al. |
| 2019/0038344 A1 | 2/2019 | Pellegrino |
| 2019/0038345 A1 | 2/2019 | Pellegrino |
| 2019/0090933 A1 | 3/2019 | Pellegrino et al. |
| 2019/0110833 A1 | 4/2019 | Pellegrino et al. |
| 2019/0118003 A1 | 4/2019 | Diederich et al. |
| 2019/0118004 A1 | 4/2019 | Diederich et al. |
| 2019/0118005 A1 | 4/2019 | Diederich et al. |
| 2019/0175252 A1 | 6/2019 | Heggeness |
| 2019/0282268 A1 | 9/2019 | Pellegrino et al. |
| 2019/0290296 A1 | 9/2019 | Patel et al. |
| 2019/0298392 A1 | 10/2019 | Capote et al. |
| 2019/0365416 A1 | 12/2019 | Brockman et al. |
| 2020/0000480 A1 | 1/2020 | Alambeigi et al. |
| 2020/0022709 A1 | 1/2020 | Burger et al. |
| 2020/0030601 A1 | 1/2020 | Molnar et al. |
| 2020/0060695 A1 | 2/2020 | Purdy et al. |
| 2020/0060747 A1 | 2/2020 | Edidin |
| 2020/0069920 A1 | 3/2020 | Goshayeshgar |
| 2020/0078083 A1 | 3/2020 | Sprinkle et al. |
| 2020/0138454 A1 | 5/2020 | Patel et al. |
| 2020/0146743 A1 | 5/2020 | Defosset et al. |
| 2020/0146744 A1 | 5/2020 | Defosset et al. |
| 2020/0214762 A1 | 7/2020 | Pellegrino et al. |
| 2020/0281646 A1 | 9/2020 | Pellegrino et al. |

FOREIGN PATENT DOCUMENTS

| | | |
|---|---|---|
| EP | 0597463 | 5/1994 |
| EP | 0880938 | 12/1998 |
| EP | 1013228 | 6/2000 |
| EP | 1059067 | 12/2000 |
| EP | 1059087 | 12/2000 |
| EP | 1294323 B1 | 4/2007 |
| EP | 1938765 A1 | 7/2008 |
| EP | 1471836 B1 | 4/2010 |
| EP | 2785260 B1 | 8/2015 |
| EP | 2965782 A1 | 1/2016 |
| EP | 2508225 B1 | 9/2016 |
| EP | 2582289 B1 | 9/2016 |
| EP | 3078395 A1 | 10/2016 |
| EP | 2205313 B1 | 11/2016 |
| EP | 3097946 A1 | 11/2016 |
| EP | 2913081 B1 | 1/2017 |
| JP | S 53-139791 | 11/1978 |
| JP | 6-47058 | 2/1994 |
| JP | 10-290806 | 11/1998 |
| JP | 2001-037760 | 2/2001 |
| JP | 2005-169012 | 6/2005 |
| WO | WO96/36289 | 11/1996 |
| WO | WO98/27876 | 7/1998 |
| WO | WO98/34550 | 8/1998 |
| WO | WO99/19025 | 4/1999 |
| WO | WO99/44519 | 9/1999 |
| WO | WO99/48621 | 9/1999 |
| WO | WO00/21448 | 4/2000 |
| WO | WO00/33909 | 6/2000 |
| WO | WO00/49978 | 8/2000 |
| WO | WO00/56237 | 9/2000 |
| WO | WO00/67648 | 11/2000 |
| WO | WO00/67656 | 11/2000 |
| WO | WO01/01877 | 1/2001 |
| WO | WO01/45579 | 6/2001 |
| WO | WO01/57655 | 8/2001 |
| WO | WO02/05699 | 1/2002 |
| WO | WO02/05897 | 1/2002 |
| WO | WO02/28302 | 4/2002 |
| WO | WO2002/026319 | 4/2002 |
| WO | WO02/054941 | 7/2002 |
| WO | WO02/067797 | 9/2002 |
| WO | WO02/096304 | 12/2002 |
| WO | WO 2006/044794 | 4/2006 |
| WO | WO 2007/001981 | 1/2007 |
| WO | WO 2007/008954 | 1/2007 |
| WO | WO07/031264 | 3/2007 |
| WO | WO08/001385 | 1/2008 |
| WO | WO08/008522 | 1/2008 |
| WO | WO2008/076330 | 6/2008 |
| WO | WO2008/076357 | 6/2008 |
| WO | WO08/121259 | 10/2008 |
| WO | WO2008/121259 | 10/2008 |
| WO | WO2008/140519 | 11/2008 |
| WO | WO 2008/141104 | 11/2008 |
| WO | WO2008/144709 | 11/2008 |
| WO | WO 2009/042172 | 4/2009 |
| WO | WO 2009/076461 | 6/2009 |
| WO | WO 2009/124192 | 10/2009 |
| WO | WO2009/155319 | 12/2009 |
| WO | WO2010/111246 | 9/2010 |
| WO | WO2010/135606 | 11/2010 |
| WO | WO2011/041038 | 4/2011 |
| WO | WO2012/024162 | 2/2012 |
| WO | WO 2012/065753 | 3/2012 |
| WO | WO2012/074932 | 6/2012 |
| WO | WO2013/009516 | 1/2013 |
| WO | WO 2013/134452 | 9/2013 |
| WO | WO 2013/168006 | 11/2013 |
| WO | WO2013/180947 | 12/2013 |
| WO | WO 2014/004051 | 1/2014 |
| WO | WO2014/130231 | 8/2014 |
| WO | WO 2014/141207 | 9/2014 |

(56) References Cited

FOREIGN PATENT DOCUMENTS

| WO | WO 2014/145222 | 9/2014 |
|---|---|---|
| WO | WO 2014/145659 | 9/2014 |
| WO | WO 2014/146029 | 9/2014 |
| WO | WO2014/165194 | 10/2014 |
| WO | WO2014/176141 | 10/2014 |
| WO | WO 2014/197596 | 12/2014 |
| WO | WO 2014/210373 | 12/2014 |
| WO | WO 2015/024013 | 2/2015 |
| WO | WO2015/038317 | 3/2015 |
| WO | WO 2015/044945 | 4/2015 |
| WO | WO 2015/047817 | 4/2015 |
| WO | WO 2015/057696 | 4/2015 |
| WO | WO 2015/060927 | 4/2015 |
| WO | WO 2015/066295 | 5/2015 |
| WO | WO 2015/066303 | 5/2015 |
| WO | WO 2015/079319 | 6/2015 |
| WO | WO 2015/148105 | 10/2015 |
| WO | WO2016/033380 | 3/2016 |
| WO | WO2016/048965 | 3/2016 |
| WO | WO2016/069157 | 5/2016 |
| WO | WO2016/075544 | 5/2016 |
| WO | WO2016/090420 | 6/2016 |
| WO | WO2016/105448 | 6/2016 |
| WO | WO2016/105449 | 6/2016 |
| WO | WO2016/127130 | 8/2016 |
| WO | WO2016/130686 | 8/2016 |
| WO | WO2016/134273 | 8/2016 |
| WO | WO2016/148954 | 9/2016 |
| WO | WO2016/154091 | 9/2016 |
| WO | WO 2016/138381 | 10/2016 |
| WO | WO2016/209682 | 12/2016 |
| WO | WO2017/009472 | 1/2017 |
| WO | WO2017/010930 | 1/2017 |
| WO | WO2017/019863 | 2/2017 |
| WO | WO2017/027703 | 2/2017 |
| WO | WO2017/027809 | 2/2017 |
| WO | WO2018/116273 | 6/2018 |
| WO | WO 2020/198150 | 10/2020 |

OTHER PUBLICATIONS

Becker, Stephan, et al., "Ablation of the basivertebral nerve for treatment of back pain: a clinical study," The Spine Journal, vol. 17, pp. 218-223 (Feb. 2017).

Caragee, EG et al.; "Discographic, MRI and psychosocial determinants of low back pain disability and remission: A prospective study in subjects with benign persistent back pain", The Spine Journal: The Official Journal of the North American Spine Society, vol. 5(1), pp. 24-35 (2005).

Fields, AJ et al.; "Innervation of pathologies in the lumbar vertebral endplate and intervertebral disc", The Spine Journal: Official Journal of the North American Spine Society, vol. 14(3), pp. 513-521 (2014).

Fields, Aaron J. et al.; "Cartilage endplate damage strongly assocates with chronic low back pain, independent of modic changes", Abstract form Oral Presentation at the ISSLS Annual Meeting in Banff, Canada (May 14-18, 2018).

Fischgrund JS, et al.; "Intraosseous Basivertebral Nerve Ablation for the Treatment of Chronic Low Back Pain: 2-Year Results from a Prospective Randomized Double-Blind Sham-Controlled Multi-center Study", International Journal of Spine Surgery, vol. 13 (2), pp. 110-119 (2019).

Gornet, Matthew G et al.; "Magnetic resonance spectroscopy (MRS) can identify painful lumbar discs and may facilitate improved clinical outcomes of lumbar surgeries for discogenic pain", European Spine Journal, vol. 28, pp. 674-687 (2019).

Heggeness, M. et al Ablation of the Basivertebral Nerve for the Treatment of Back Pain: A Pilot Clinical Study; The Spine Journal, 2011, vol. 11, Issue 10, Supplement, pp. S65-S66, ISSN 1529-9430.

Jourabchi, Natanel et al.; "Irreversible electroporation (NanoKnife) in cancer treatment," Gastrointestinal Intervention, vol. 3, pp. 8-18 (2014).

Khalil, J et al.; "A Prospective, Randomized, Multi-Center Study of Intraosseous Basivertebral Nerve Ablation for the Treatment of Chronic Low Back Pain", The Spine Journal (2019), avilable at https://doi.org/10.1016/jspinee.2019.05.598.

Kuisma M et al.; "Modic changes in endplates of lumbar vertebral bodies: Prevalence and association with low back and sciatic pain among middle-aged male workers", Spine, vol. 32(10), pp. 1116-1122 (2007).

Lotz JC, et al.; "The Role of the Vertebral End Plate in Low Back Pain", Global Spine Journal, vol. 3, pp. 153-164 (2013).

Mok, Florence et al.; "Modic changes of the lumbar spine: Prevalence, risk factors, and association with disc degeneration and low back pain in a large-scale population-based cohort", The Spine Journal: Official Journal of the North American Spine Society, vol. 16(1), pp. 32-41 (2016).

Pang, Henry et al,; The UTE Disc Sign on MRI: A Novel Imaging Biomarker Associated With Degenerative Spine Changes, Low Back Pain, and Disability, Spine, vol. 42 (Aug. 2017).

Radiological Society of North America. "Pulsed radiofrequency relieves acute back pain and sciatica." ScienceDaily. ScienceDaily, Nov. 27, 2018. <www.sciencedaily.com/releases/2018/11/181127092604.htm>.

Osteocool Pain Management Brochure, Baylis Medical, copyright 2011.

YouTube Video, "DFINE-STAR Procedure Animation," dated Sep. 30, 2013, can be viewed at https://www.youtube.com/watch?v=YxtKNyc2e-0.

Weishaupt, D et al,; "Painful Lumbar Disk Derangement: Relevance of Endplate Abnormalities at MR Imaging", Radiology, vol. 218(2), pp. 420-427 (2001).

Kim et al., Transforaminal epiduroscopic basivertebral nerve laser ablation for chronic low back pain associated with modic changes: A preliminary open-label study. Pain Research and Management 2018; https://pubmed.ncbi.nlm.nih.gov/30186540.

Rahme et al., The modic vertebral endplate and marrow changes: pathologic significance and relation to low back pain and segmental instability of the lumbar spine. American Journal of Neuroradiology 29.5 (2008): 838-842; http://www.ajnr.org/content/29/5/838.

A Novel Approach for Treating Chronic Lower Back Pain, Abstract for Presentation at North American Spine Society 26th Annual Meeting in Chicago, IL on Nov. 4, 2011.

Antonacci, M. Darryl et al.; Innervation of the Human Vertebral Body: A Histologic Study; Journal of Spinal Disorder, vol. 11, No. 6, pp. 526-531, 1998 Lippincott Wiliams & Wilkins, Philadelphia.

Arnoldi, Carl C.; Intraosseous Hypertension—A Possible Cause of Low Back Pain?; Clinical Orthopedics and Related Research, No. 115, Mar.-Apr. 1976.

Bergeron et al., "Fluoroscopic-guided radiofrequency ablation of the basivertebral nerve: application and analysis with multiple imaging modalities in an ovine model," Thermal Treatment of Tissue: Energy Delivery and Assessment III, edited by Thomas P. Ryan, Proceedings of SPIE, vol. 5698 (SPIE, Bellingham, WA, 2005) pp. 156-167.

Bogduk, N., The anatomy of the lumbar Intervertebral disc syndrome, Med J. Aust. 1976, vol. 1, No. 23, pp. 878-881.

Bogduk, Nikolal, et al.; Technical Limitations to the efficacy of Radiofrequency Neurotomy for Spinal Pain; Neurosurgery vol. 20. No. 4, 1987.

Choy, Daniel SS.J. et al.; Percutaneous Laser Disc Decompression, a New Therapeutic Modality; Spine vol. 17, No. 8, 1992.

Cosman, E.R. et al., Theoretical Aspects of Radiofrequency Lesions in the Dorsal Root Entry Zone. Neurosurgery, vol. 1, No. 6, 1984, pp. 945-950.

Deardorff, Dana L. et al.; Ultrasound applicators with internal cooling for interstitial thermal therapy; SPIE vol. 3594, 1999.

Deramond, H. et al., Temperature Elevation Caused by Bone Cement Polymerization During Vertebroplasty, Bone, Aug. 1999, p. 17S-21S, vol. 25, No. 2, Supplement.

Diederich, C. J. et al., "IDTT Therapy in Cadaveric Lumbar Spine: Temperature and thermal dose distributions, Thermal Treatment of Tissue: Energy Delivery and Assessment," Thomas P. Ryan, Editor, Proceedings of SPIE vol. 4247:104-108 (2001).

(56) References Cited

OTHER PUBLICATIONS

Diederich, Chris J. et al.; Ultrasound Catheters for Circumferential Cardiac Ablation; SPIE vol. 3594 (1999).
Dupuy, D.E. et al. Radiofrequency ablation of spinal tumors: Temperature distribution in the spinal canal AJR, vol. 175, pp. 1263-1266, Nov. 2000.
Dupuy. Damian E.; Radiofrequency Ablation: An Outpatient Percutaneous Treatment; Medicine and Health/Rhode Island vol. 82, No. 6, Jun. 1999.
Esses, Stephen I. et al.; Intraosseous Vertebral Body Pressures; Spine vol. 17 No. 6 Supplement 1992.
FDA Response to 510(k) Submission by Relievant Medsystems, Inc. submitted on Sep. 27, 2007 (date stamped on Oct. 5, 2007) and associated documents.
Fras M.D., Christian et al., "Substance P-containing Nerves within the Human Vertebral Body: An Immunohistochemical Study of the Basivertebral Nerve", The Spine Journal 3, 2003, pp. 63-67RE.
Gehl, J., "Electroporation: theory and methods, perspectives for drug delivery, gene therapy, and research", Acta Physiol. Scand., vol. 177, pp. 437-447 (2003).
Goldberg, S.N. et al., Tissue ablation with radiofrequency: Effect of probe size, gauge, duration, and temperature on lesion volume, Acad. Radiol., vol. 2, pp. 399-404 (1995).
Hanai, Kenji et al.; Simultaneous Measurement of Intraosseous and Cerebrospinal Fluid Pressures in the Lumbar Region; Spine vol. 10, No. 1, 1985.
Heggeness, Michael H. et al., The Trabecular Anatomy of Thoracolumbar Vertebrae: Implications for Burst Fractures, Journal of Anatomy, 1997, pp. 309-312, vol. 191, Great Britain.
Heggeness, Michael H. et al. Discography Causes End Plate Deflection; Spine vol. 18, No. 8, pp. 1050-1053, 1993, J.B. Lippincott Company.
Hoopes et al., "Radiofrequency Ablation of the Basivertebral Nerve as a Potential Treatment of Back Pain: Pathologic Assessment in an Ovine Model," Thermal Treatment of Tissue: Energy Delivery and Assessment III, edited by Thomas P. Ryan, Proceedings of SPIE, vol. 5698 (SPIE, Bellingham, WA, 2005) pp. 168-180.
Houpt, Jonathan C. et al.; Experimental Study of Temperature Distributions and Thermal Transport During Radiofrequency Current Therapy of the Intervertebral Disc; Spine vol. 21, No. 15, pp. 1808-1813, 1996, Lippincott-Raven Publishers.
Kleinstueck, Frank S. et al.; Acute Biomechanical and Histological Effects of Intradiscal Electrothermal Therapy on Human Lumbar Discs; Spine vol. 26, No. 20, pp. 2198-2207; 2001, Lippincott Williams & Wilkins, Inc.
Kopecky, Kenyon K. et al. "Side-Exiting Coaxial Needle for Aspiration Biopsy"—AJR—1996; 167, pp. 661-662.
Lehmann, Justus F. et al.; Selective Heating Effects of Ultrasound in Human Beings; Archives of Physical Medicine & Rehabilitation Jun. 1966.
Letcher, Frank S. et al.; The Effect of Radiofrequency Current and Heat on Peripheral Nerve Action Potential in the Cat; U.S, Naval Hospital, Philadelphia, PA, (1968).
Lundskog, Jan; Heat and Bone Tissue-/an experimental investigation of the thermal properties of bone tissue and threshold levels for thermal injury; Scandinavian Journal of Plastic and Reconstructive Surgery Supplemental 9, From the Laboratory of Experimental Biology, Department of anatomy, University of Gothenburg, Gothenburg, Sweden, Goteborg 1972.
Martin, J.B. et al., Vertebroplasty: Clinical Experience and Follow-up Results, Bone, Aug. 1999, p. 11S-15S, vol. 25. No. 2, Supplement.
Massad, Malek M.D. et al.; Endoscopic Thoracic Sympathectomy: Evaluation of Pulsatile Laser, Non-Pulsatile Laser, and Radiofrequency-Generated Thermocoagulation; Lasers in Surgery and Medicine; 1991; pp. 18-25.
Mehta, Mark et al.; The treatment of chronic back pain; Anaesthesia, 1979, vol. 34, pp. 768-775.
Modic MT et al.; "Degenerative disk disease: assessment of changes in vertebral body marrow with MR imaging", Radiology, vol. 166, pp. 193-199 (1988).
Nau, Wiliam H., Ultrasound interstitial thermal therapy (USITT) in the prostate; SPIE vol. 3594, Jan. 1999.
Rashbaum, Ralph F.; Radiofrequency Facet Denervation A Treatment alternative in Refractory Low Back Pain with or without Leg Pain; Orthopedic Clinics of North America—vol. 14, No. 3, Jul. 1983.
Rosenthal, D.I., Seminars in Musculoskeletal Radiology, vol. 1, No. 2., pp. 265-272 (1997).
Ryan et al., "Three-Dimensional Finite Element Simulations of Vertebral Body Thermal Treatment," Thermal Treatment of Tissue: Energy Delivery and Assessment III, edited by Thomas P. Ryan, Proceedings of SPIE, vol. 5698 (SPIE, Bellingham, WA, 2005) pp. 137-155.
Shealy, C. Norman; Percutaneous radiofrequency denervation of spinal facets Treatment for chronic back pain and sciatica; Journal of Neurosurgery/vol. 43/Oct. 1975.
Sherman, Mary S.: The Nerves of Bone, The Journal of Bone and Joint Surgery, Apr. 1963, pp. 522-528, vol. 45-A, No. 3.
Solbiati, L. et al. Hepatic metastases: Percutaneous radio-frequency ablation with cooled-tip electrodes. Interventional Radiology, vol. 205, No. 2, pp. 367-373 (1997).
Stanton, Terry, "Can Nerve Ablation Reduce Chronic Back Pain?" AAOS Now Jan. 2012.
The AVAmax System—Cardinal Health Special Procedures, Lit. No. 25P0459-01—www.cardinal.com (copyright 2007).
Tillotson, L. et al. Controlled thermal injury of bone: Report of a percutaneous technique using radiofrequency electrode and generator. Investigative Radiology, Nov. 1989. pp. 888-892.
Troussier, B. et al.; Percutaneous Intradiscal Radio-Frequency Thermocoagulation A Cadaveric Study; Spine vol. 20, No. 15, pp. 1713-1718, 1995, Lippincott-Raven Publishers.
Ullrich, Jr., Peter F., "Lumbar Spinal Fusion Surgery" Jan. 9, 2013, Spine-Health (available via wayback machine Internet archive at http://web.archive.org/web/20130109095419/http://www/spine-health.com/treatment/spinal-fusion/lumbar-spinal-fusion-surgery).

* cited by examiner

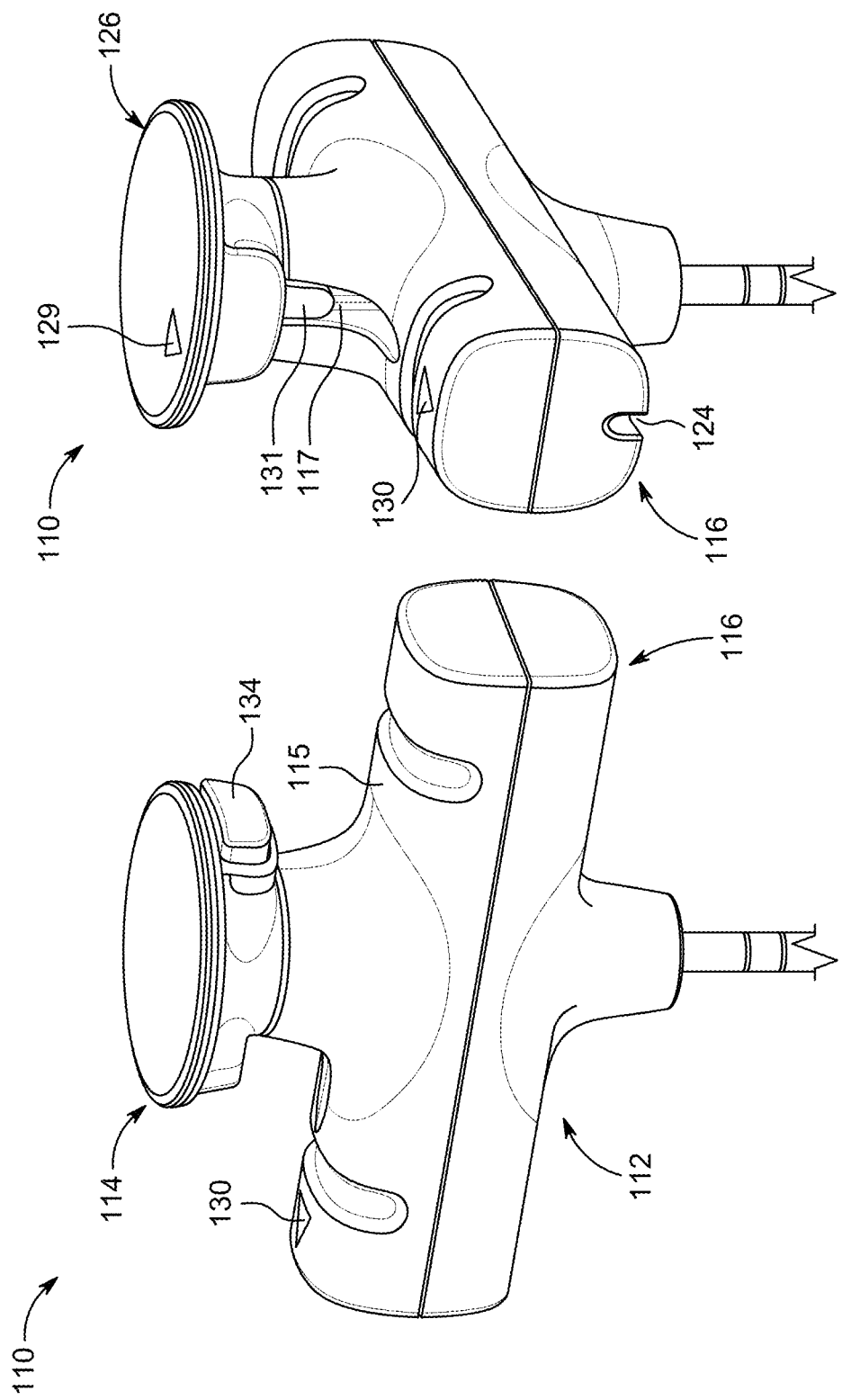

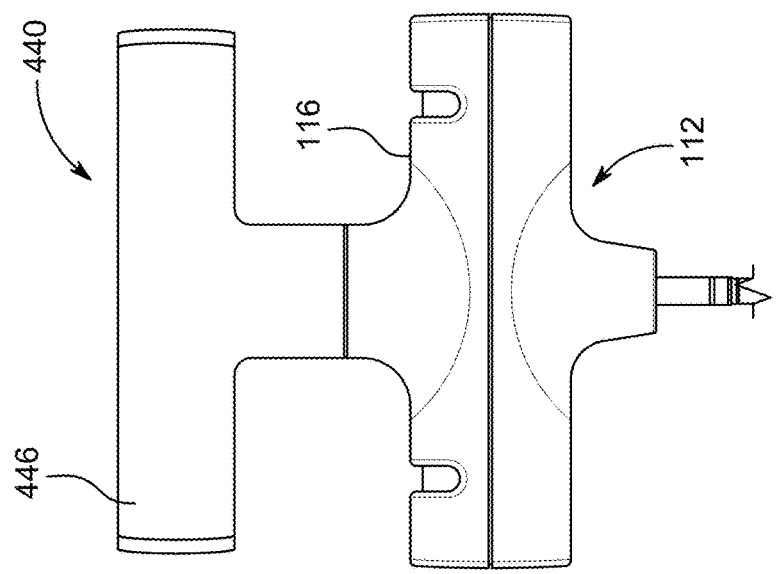
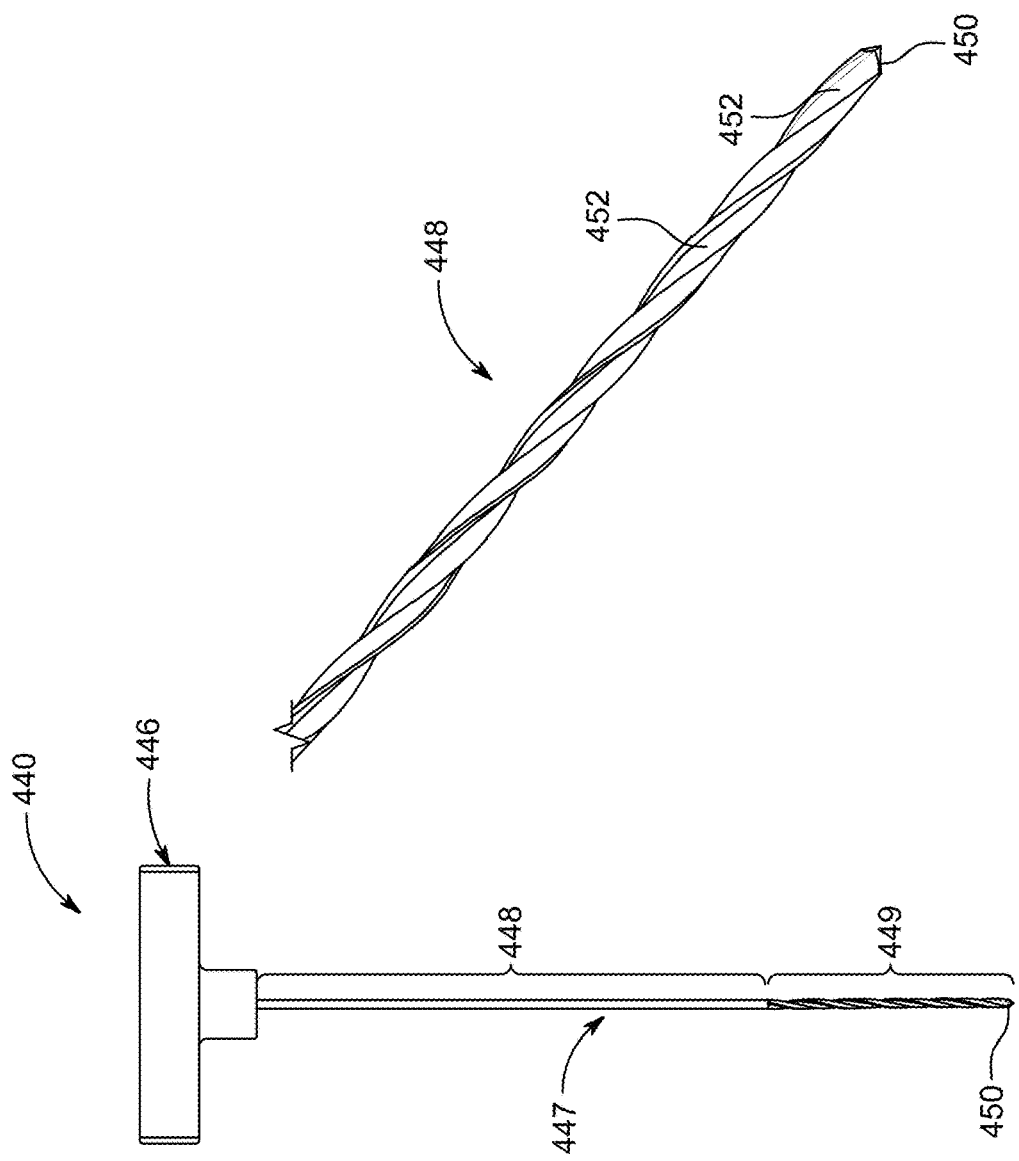
FIG. 3Z
FIG. 3Y
FIG. 3X

INTRODUCER SYSTEMS FOR BONE ACCESS

RELATED APPLICATIONS

This application is a continuation of International PCT Application No. PCT/US2020/050249 filed Sep. 10, 2020, which claims the benefit of priority to U.S. Provisional Application No. 62/899,622 filed Sep. 12, 2019, the entire content of each of which is hereby incorporated by reference herein.

FIELD

Described herein are various implementations of systems and methods for modulating tissue (for example, systems and methods for ablating nerves or other tissue within or surrounding a vertebral body to treat chronic lower back pain). Several embodiments comprise the use of biomarkers to confirm or otherwise assess ablation, pain relief, efficacy of treatment, etc. Some embodiments include robotic elements for, as an example, facilitating robotically controlled access, navigation, imaging, and/or treatment. Assessment of vertebral endplate degeneration or defects (e.g., pre-Modic changes) to facilitate identification of treatment sites and protocols are also provided in several embodiments. Systems or kits of access tools for accessing target treatment locations within vertebral bodies are also provided.

BACKGROUND

Back pain is a very common health problem worldwide and is a major cause for work-related disability benefits and compensation. At any given time, low back pain impacts nearly 30% of the US population, leading to 62 million annual visits to hospitals, emergency departments, outpatient clinics, and physician offices. Back pain may arise from strained muscles, ligaments, or tendons in the back and/or structural problems with bones or spinal discs. The back pain may be acute or chronic. Existing treatments for chronic back pain vary widely and include physical therapy and exercise, chiropractic treatments, injections, rest, pharmacological therapy such as opioids, pain relievers or anti-inflammatory medications, and surgical intervention such as vertebral fusion, discectomy (e.g., total disc replacement), or disc repair. Existing treatments can be costly, addictive, temporary, ineffective, and/or can increase the pain or require long recovery times. In addition, existing treatments do not provide adequate relief for the majority of patients and only a small percentage are surgically eligible.

SUMMARY

Applicant's existing technology (the Intracept® procedure by Relievant®) offers a safe and effective minimally invasive procedure that targets the basivertebral nerve for the relief of chronic vertebrogenic low back pain. As disclosed herein, several embodiments provide bone access tools, additional modalities of relief for patients and/or adjunct technologies.

In accordance with several embodiments, quantitative efficacy of treatment or efficacy of nerve ablation may be performed by assessing levels of one or more biomarkers (e.g., biomarkers associated with pain, inflammation, or neurotransmission). Such assessment may be particular useful to assess pain, for example. Pain can be very subjective based on individual patient pain tolerance and perception. Accordingly, it can be difficult to assess or quantify efficacy of pain treatment based on patient feedback. It has also been difficult historically to assess efficacy of nerve ablation in real time. For example, patients may be under anesthetic and unable to provide feedback. In other cases, patients may be awake but unable to accurately assess pain. The use of biomarkers, in some embodiments can facilitate pain assessment or confirmation of efficacy of nerve ablation.

For example, a level or activity of one or more biomarkers may be measured or otherwise obtained prior to performing a procedure and after performing a procedure. The pre-procedure and post-procedure levels may be compared in order to quantitatively (non-subjectively) assess efficacy. The biomarkers may be associated with pain levels or associated with lesion formation (e.g., efficacy of neurotransmission or neural communication). The assessment of the level of the one or more biomarkers may advantageously be performed in a non-invasive or minimally-invasive (e.g., non-surgical) manner in accordance with several embodiments. Biomarkers may also be used to assess whether a particular subject is likely to be a candidate for nerve ablation treatment for treatment of back pain. For example, the biomarkers may be indicative of pre-Modic changes or symptoms likely to result in Modic changes or endplate damage (e.g., inflammation, edema, bone marrow lesions or fibrosis). The assessment of biomarker levels may indicate which vertebral bodies of a particular subject are candidates for treatment to prevent (or reduce the likelihood of) back pain from developing or worsening or to treat existing back pain. The pre-procedure biomarker assessment may also be combined with pre-procedure imaging. Mechanisms other than using biomarkers may also be used (in addition or in the alternative) to assess lesion formation (e.g., infrared sensing, heat markers, neurotransmission assessments via stimulation, and/or ultrasound imaging).

In some embodiments, automated systems for accessing and/or treating tissue (such as nerves) are provided. In accordance with several embodiments, robotically-enabled or robotically-controlled surgical, access, and/or treatment tools may provide a high level of control and precision of movement and increased dexterity and range of motion, thereby providing increased assurance that injury will not occur to tissue not desired to be impacted. Robotically-controlled tools and techniques (e.g., computer-aided tools and techniques that may incorporate artificial intelligence learning and feedback) may also be used to facilitate navigation to, and surgical operation at, desired target treatment regions that may be difficult to access manually, thereby providing enhanced flexibility and possibilities thought not to be possible via manual human surgery. Robotically-controlled tools and techniques (e.g., computer-aided tools and techniques that may incorporate artificial intelligence learning and feedback) may further be used to facilitate capture of images pre-operatively or intra-operatively without exposing the target treatment regions to radiation or without requiring large incisions to be made. Nerve detection devices (e.g., nerve monitoring devices or nerve finders) may also be used to detect nerves along access routes that are desired to be avoided during access. Robotic or automated tools and techniques may reduce numbers of and sizes of incisions (and therefore scars), may reduce blood loss, may reduce pain, and may decrease recovery time.

Because the target treatment regions within vertebral bodies may be fairly small in size, it may be desirable to control or adjust lesion formation so as to exhibit specific lesion shapes (e.g., football-shape, oval, elliptical, disc-shaped, cigar-shaped, dumbbell-shaped, UFO-shaped, rounded, rectangular, amorphous, etc.). Creating specific lesion shapes may allow clinicians to efficiently ablate a basivertebral nerve trunk within specific vertebral bodies (e.g., cervical, thoracic, lumbar, sacral vertebrae). The specific lesion shapes may provide increased confidence in the efficacy of ablation while limiting the extent of thermal injury within the vertebral body. The lesion shapes may be controlled by applying voltage differentials between different pairs of electrodes on the same energy delivery probe or on different energy delivery probes for different durations. The lesion formation may be monitored and controlled in real time (e.g., using feedback based on imaging, thermal sensing, and/or artificial intelligence) to further increase confidence and efficiency. Use of two probes and delivering energy between the two probes may result in synergistic lesion formation (e.g., larger lesions than could be formed by individual probes alone).

Treatment procedures may include modulation of nerves within or surrounding bones. The terms "modulation" or "neuromodulation", as used herein, shall be given their ordinary meaning and shall also include ablation, permanent denervation, temporary denervation, disruption, blocking, inhibition, electroporation, therapeutic stimulation, diagnostic stimulation, inhibition, necrosis, desensitization, or other effect on tissue. Neuromodulation shall refer to modulation of a nerve (structurally and/or functionally) and/or neurotransmission. Modulation is not necessarily limited to nerves and may include effects on other tissue, such as tumors or other soft tissue.

In accordance with several embodiments, a method of ablating a basivertebral nerve within a vertebral body of a subject and confirming efficacy of ablation of the basivertebral nerve includes obtaining a first reading (e.g., baseline reading) of a level of a biomarker from the subject. The method further includes performing a denervation procedure on the subject. As one example, the denervation procedure includes denervating the basivertebral nerve within the vertebral body. The method also includes obtaining a second reading (e.g., post-procedure reading) of the level of the biomarker from the subject and determining an effect of the denervation procedure by comparing the second reading to the first reading to assess efficacy of the denervation procedure.

The biomarkers may include one or more of: an inflammatory cytokine (e.g., interleukins, interferons, tumor necrosis factors, prostaglandins, and chemokines), pain indicators (e.g., substance P, calcitonin gene-related peptides (CGRPs)), an edema factor, and/or other inflammatory factor. The first reading (e.g., baseline reading) and the second reading (e.g., post-procedure reading) may be obtained from cerebrospinal fluid adjacent the vertebral body of the subject, from a blood draw (e.g., at a location within or adjacent the vertebral body of the subject or at a remote location systemically), from a urine sample, or other source. The biomarkers may be circulating inflammatory cells (e.g., cytokines). The biomarkers may be obtained via one or more immunoassay techniques (e.g., ELISAs, cytokine bead arrays, cytokine microarrays, flow cytometry, immunohistochemical assays, and/or the like).

The step of denervating the basivertebral nerve within the vertebral body may include applying energy (e.g., radiofrequency energy, ultrasound energy, microwave energy) to a target treatment region within the vertebral body sufficient to denervate (e.g., ablate, electroporate, molecularly dissociate, necrose) the basivertebral nerve using a radiofrequency energy delivery device. The step of denervating may alternatively or additionally include applying an ablative fluid (e.g., steam, chemical, cryoablative fluid) to a target treatment region within the vertebral body. In some implementations, the step of denervating may include delivering a water jet at a pressure sufficient to denervate the nerve (e.g., between 5 and 10 MPa, between 10 and 15 MPa, between 15 and 30 MPa, between 30 and 50 MPa, overlapping ranges thereof, pressure greater than 50 MPa, or any value within the recited ranges).

In accordance with several embodiments, a method of detecting and treating back pain of a subject includes obtaining images of a vertebral body of the subject, analyzing the images to determine whether the vertebral body exhibits one or more symptoms associated with a pre-Modic change, and ablating a basivertebral nerve within the vertebral body if it is determined that the vertebral body exhibits one or more symptoms associated with a pre-Modic change. The one or more symptoms associated with a pre-Modic change may include edema, inflammation, and/or tissue changes (e.g., tissue lesions, fibrosis, or other changes in tissue type or characteristics) of bone, bone marrow, and/or endplate(s).

In accordance with several embodiments, a method of treating a vertebral body includes inserting a first access assembly into a first target location of the vertebral body. The first access assembly includes a first cannula and a first stylet configured to be inserted within the first cannula until a distal tip of the first stylet is advanced to or beyond an open distal tip of the first cannula. The method further includes removing the first stylet from the first cannula. The method also includes inserting a second access assembly into a second target location of the vertebral body. The second access assembly including a second cannula and a second stylet configured to be inserted within the second cannula until a distal tip of the second stylet is advanced to or beyond an open distal tip of the second cannula. The method further includes removing the second stylet. The method also includes inserting a first radiofrequency energy delivery device through the first cannula and inserting a second radiofrequency energy delivery device through the second cannula. The first radiofrequency energy delivery device and the second radiofrequency energy delivery device each include at least two electrodes (e.g., an active electrode and a return electrode configured to act as a bipolar electrode pair). The method further includes positioning the at least two electrodes of the first radiofrequency energy delivery device within the vertebral body and positioning the at least two electrodes of the second radiofrequency energy delivery device within the vertebral body.

The method also includes applying power to the first and second radiofrequency energy delivery devices sufficient to create a desired lesion shape within the vertebral body sufficient to ablate a basivertebral nerve within the vertebral body (e.g., football-shaped lesion, an elliptical-shaped lesion having a length-to-width ration of at least 2:1, a cross-shaped lesion, an X-shaped lesion, a cigar-shaped lesion). The lesion may have a maximum width of 20 mm and a maximum length of 30 mm. The lesion may have a maximum width of 70-80% of the anteroposterior depth of the vertebral body and a maximum length of 70-85% of the transverse width of the vertebral body. In some implementations, the step of applying power to the first and second radiofrequency energy delivery devices includes independently applying power to the first and second radiofrequency energy delivery devices for a first duration of time (e.g., 1 minute-2 minutes, 30 seconds-90 seconds, 2-5 minutes, 5-10 minutes, 10-15 minutes, overlapping ranges thereof, or any value within the recited ranges). In some implementations, the step of applying power to the first and second radiofrequency energy delivery devices further includes applying a voltage differential between at least one of the at least two electrodes of the first radiofrequency energy delivery device and at least one of the at least two electrodes of the second radiofrequency energy delivery device for a second duration of time (e.g., 1 minute-2 minutes, 30 seconds-90 seconds, 2-5 minutes, 5-10 minutes, 10-15 minutes, overlapping ranges thereof, or any value within the recited ranges). The first duration of time and the second duration of time may be the same or different.

In accordance with several embodiments, a method of ablating a basivertebral nerve within a vertebral body includes inserting an access assembly within a vertebral body using a robotically-controlled system. The access assembly includes at least one cannula. The method further includes inserting a radiofrequency energy delivery device through the cannula to a target treatment site within the vertebral body using the robotically-controlled system, and applying power to the target treatment site using the radiofrequency energy delivery device sufficient to ablate the basivertebral nerve.

In some implementations, the robotically-controlled system includes one or more robotic arms and an operator control console including at least one processor. The system may include one or more imaging devices configured to provide feedback (e.g., based on artificial intelligence processing algorithms) to the robotically-controlled system to control insertion of the access assembly and/or the radiofrequency energy delivery device.

In accordance with several embodiments, a radiofrequency ("RF") generator for facilitating nerve ablation includes a display screen (e.g., color active matrix display) and an instrument connection port configured to receive a corresponding connector of a radiofrequency probe. The generator further includes a first indicator light ring (e.g., circular LED indicator light ring) surrounding the instrument connection port that is configured to illuminate when a treatment device is connected to the instrument connection port. The first indicator light ring is configured to continuously illuminate in a solid color (e.g., white, green, blue) when the treatment device is connected to the instrument connection port, to flash at a first pulsing rate (e.g., 1 Hz) to prompt a clinician to connect the treatment device to the instrument connection port, and to flash at a second pulsing rate different than (e.g., greater than 1 Hz, such as 2 Hz, 3 Hz or 4 Hz) the first pulsing rate to indicate an error condition. The generator may optionally be configured to output an audible alert or alarm to indicate the error condition. The generator also includes an energy delivery actuation button configured to be pressed by an operator to start and stop delivery of radiofrequency energy and a second indicator light ring (e.g., circular LED light ring) surrounding the actuation button. The second indicator light ring is configured to continuously illuminate in a solid color (e.g., white, blue, green) when the generator is powered on and ready to initiate energy delivery, to flash at a third pulsing rate (e.g., 1 Hz) to prompt the operator to press the actuation button to initiate energy delivery, and to flash at a fourth pulsing rate different than (e.g., greater than 1 Hz, such as 2 Hz, 3 Hz, 4 Hz) the third pulsing rate when energy delivery has been paused or stopped.

In accordance with several embodiments, a system for facilitating nerve ablation includes an operator control console comprising a computer-based control system including at least one processor that is configured to execute program instructions stored on a non-transitory computer-readable medium to carry out a nerve ablation procedure to ablate a basivertebral nerve within one or more vertebral bodies using automated robotic surgical arms. The one or more robotic surgical arms are configured to move with six or more degrees of freedom and to support or carry access tools (e.g., cannulas, stylets, bone drills, curettes), treatment devices (e.g., radiofrequency probes, microwave ablation catheters, ultrasound probes), and/or diagnostic devices (e.g., cameras, sensors, and/or the like). The system may optionally include one or more imaging devices configured to obtain images of a target treatment site prior to, during, and/or after a treatment procedure.

In accordance with several embodiments, a method of facilitating ablation of a basivertebral nerve within a vertebral body comprising applying radiofrequency energy to a location within the vertebral body according to the following treatment parameters: a frequency between 400 kHz and 600 kHz (e.g., between 400 kHz and 500 kHz, between 450 kHz and 500 kHz, between 470 kHz and 490 kHz, between 500 kHz and 600 kHz, overlapping ranges thereof, or any value within the recited ranges); a target temperature of between 80 degrees Celsius and 90 degrees Celsius (e.g., 80 degrees Celsius, 85 degrees Celsius, 90 degrees Celsius); a temperature ramp of between 0.5 and 3 degrees Celsius per second (e.g., 0.5 degree Celsius per second, 1 degree Celsius per second, 1.5 degrees Celsius per second, 2 degrees Celsius per second, 2.5 degrees Celsius per second, 3 degrees Celsius per second); and an active energy delivery time of between 10 minutes and 20 minutes (e.g., 10 minutes, 12, minutes, 14 minutes, 15 minutes, 16 minutes, 18 minutes, 20 minutes). In some implementations, a target ablation zone has a major diameter along a long axis of between 20 mm and 30 mm and a minor diameter along a short axis of between 5 mm and 15 mm.

In accordance with several embodiments, a kit for facilitating nerve ablation includes one or more biological assays configured to determine at least one biological marker (e.g., cytokine, substance P or other indicator of pain, heat shock protein). The determination includes at least one of a binary detection of a presence of the at least one biological marker, and/or a quantification (e.g., total amount) of the at least one biological marker. The determination may also optionally include an indication of location of any of the at least one biomarker or a location of a highest concentration of the at least one biomarker.

The kit may optionally include one or more access tools (e.g., stylets, cannulas, curettes, bone drills) configured to access a target nerve to be treated (e.g., basivertebral nerve). The kit may also or alternatively optionally include one or more treatment tools configured to modulate (e.g., ablate, stimulate, denervate, inhibit, necrose, electroporate, molecularly dissociate) the target nerve. The optional treatment tool include one or a combination of the following: a radiofrequency energy delivery device, a microwave energy delivery device, an ultrasound energy delivery device, a cryomodulation device (e.g., cryoablation device), a laser energy delivery device, and/or a drug eluting device (e.g., chemical or fluid ablation device configured to elute a fluid capable of denervating or ablating a nerve, such as alcohol or phenol).

In accordance with several embodiments, a method of detecting and treating back pain of a subject includes obtaining images of a vertebral body of the subject and analyzing the images to determine whether the vertebral body exhibits one or more symptoms associated with a pre-Modic change. The method also includes modulating (e.g., ablating, denervating, stimulating) an intraosseous nerve (e.g., basivertebral nerve) within the vertebral body if it is determined that the vertebral body exhibits one or more symptoms associated with a pre-Modic change.

The images may be obtained, for example, using an MRI imaging modality, a CT imaging modality, an X-ray imaging modality, an ultrasound imaging modality, or fluoroscopy. The one or more symptoms associated with a pre-Modic change may comprise characteristics likely to result in Modic changes (e.g., Type 1 Modic changes, Type 2 Modic changes). The one or more symptoms associated with a pre-Modic change may comprise initial indications or precursors of edema or inflammation at a vertebral endplate prior to a formal characterization or diagnosis as a Modic change. The one or more symptoms may include edema, inflammation, and/or tissue change within the vertebral body or along a portion of a vertebral endplate of the vertebral body. Tissue changes may include tissue lesions or changes in tissue type or characteristics of an endplate of the vertebral body and/or tissue lesions or changes in tissue type or characteristics of bone marrow of the vertebral body. The one or more symptoms may include focal defects, erosive defects, rim defects, and corner defects of a vertebral endplate of the vertebral body.

The thermal treatment dose applied may include delivery of one or more of radiofrequency energy, ultrasound energy, microwave energy, and laser energy. Ablating the basivertebral nerve within the vertebral body may comprise applying a thermal treatment dose to a location within the vertebral body of at least 240 cumulative equivalent minutes ("CEM") using a CEM at 43 degrees Celsius model. In some embodiments, the thermal treatment dose is between 200 and 300 CEM (e.g., between 200 and 240 CEM, between 230 CEM and 260 CEM, between 240 CEM and 280 CEM, between 235 CEM and 245 CEM, between 260 CEM and 300 CEM) or greater than a predetermined threshold (e.g., greater than 240 CEM).

In some embodiments, ablating the basivertebral nerve within the vertebral body comprises advancing at least a distal end portion of a radiofrequency energy delivery probe comprising two electrodes (e.g., a bipolar probe having an active electrode and a return electrode) to a target treatment location within the vertebral body and applying radiofrequency energy to the location using the energy delivery probe to generate a thermal treatment dose sufficient to modulate (e.g., ablate, denervate, stimulate) the intraosseous nerve (e.g., basivertebral nerve). The radiofrequency energy may have a frequency between 400 kHz and 600 kHz (e.g., between 400 kHz and 500 kHz, between 425 kHz and 475 kHz, between 450 kHz and 500 kHz, between 450 kHz and 550 kHz, between 475 kHz and 500 kHz, between 500 kHz and 600 kHz, overlapping ranges thereof, or any value within the recited ranges). In some embodiments, the thermal treatment dose is configured to achieve a target temperature of between 70 degrees Celsius and 95 degrees Celsius (e.g., between 70 degrees Celsius and 85 degrees Celsius, between 80 degrees Celsius and 90 degrees Celsius, between 85 degrees Celsius and 95 degrees Celsius, overlapping ranges thereof, or any value within the recited ranges) at the location. The thermal treatment dose may be delivered with a temperature ramp of between 0.1 and 5 degrees Celsius per second (e.g., between 0.5 and 1.5 degrees Celsius per second, between 1 and 2 degrees Celsius per second, between 1.5 and 3 degrees Celsius per second, between 0.5 and 3 degrees Celsius per second, between 1.5 and 5 degrees Celsius per second, overlapping ranges thereof, or any value within the recited ranges. In some embodiments, the temperature ramp is greater than 5 degrees Celsius per second. The radiofrequency energy may be applied for an active energy delivery time of between 5 minutes and 30 minutes (e.g., between 5 minutes and 15 minutes, between 10 minutes and 20 minutes, between 15 minutes and 30 minutes, overlapping ranges thereof, or any value within the recited ranges). The thermal treatment dose may form a targeted lesion zone at the target treatment location having a maximum cross-sectional dimension of less than 15 mm.

Ablating the basivertebral nerve may comprise generating a targeted ablation zone formed by a lesion having a "football" or elliptical profile shape. Ablating the basivertebral nerve may comprise generating a targeted ablation zone having a maximum cross-sectional dimension (e.g., diameter, height, width, length) of less than 15 mm. In some embodiments, ablating the basivertebral nerve comprises generating a targeted ablation zone having a maximum cross-sectional dimension (e.g., major diameter) along a long axis of between 20 mm and 30 mm and a maximum cross-sectional dimension (e.g., minor diameter) along a short axis of between 5 mm and 15 mm.

In some embodiments, the method is performed without use of any cooling fluid. The method may further include modulating (e.g., ablating, denervating, stimulating) an intraosseous nerve (e.g., basivertebral nerve) within a second vertebral body superior to or inferior to the first vertebral body.

In accordance with several embodiments, a method of detecting and treating back pain of a subject includes identifying a candidate vertebral body for treatment based on a determination that the vertebral body exhibits one or more symptoms or defects associated with vertebral endplate degeneration and ablating a basivertebral nerve within the identified candidate vertebral body by applying a thermal treatment dose to a location within the vertebral body of at least 240 cumulative equivalent minutes ("CEM") using a CEM at 43 degrees Celsius model. The one or more symptoms associated with vertebral endplate degeneration or defects include pre-Modic change characteristics.

In some embodiments, the determination is based on images of the candidate vertebral body (e.g., MRI images, CT images, X-ray images, fluoroscopic images, ultrasound images). In some embodiments, the determination is based on obtaining biomarkers from the subject. The biomarkers may be obtained, for example, from one or more blood serum samples (e.g., blood plasma). The biomarkers may be obtained over an extended period of time (e.g., a period of days, weeks, or months) or at a single instance in time.

In some embodiments, the location of the applied thermal treatment dose is in a posterior half of the vertebral body. The location may include a geometric center of the vertebral body. The location may be at least 5 mm (e.g., at least 1 cm) from a posterior border (e.g., posterior cortical aspect) of the vertebral body.

In some embodiments, the method includes advancing at least a distal end portion of a bipolar radiofrequency energy delivery probe having two electrodes to the location. The method may further include forming a passageway through a pedicle and into the vertebral body, then advancing at least the distal end portion of the bipolar radiofrequency energy delivery probe along the passageway to the location, and then applying the thermal treatment dose to the location using the bipolar radiofrequency energy delivery probe.

In some embodiments, the method further includes applying radiofrequency energy to a second location within a second vertebral body. The second vertebral body may be of a vertebra of a different vertebral level than the first vertebral body. The second vertebral body may be of a vertebra adjacent to the first vertebral body.

In accordance with several embodiments, an introducer system adapted to facilitate percutaneous access to a target treatment location within bone (e.g., a vertebral body) includes an introducer cannula comprising a proximal handle and a distal elongate hypotube extending from the proximal handle. The system further includes an introducer stylet comprising a proximal handle and a distal elongate shaft extending from the proximal handle. The proximal handle of the introducer includes a central opening in its upper surface that is coupled to a lumen of the distal elongate hypotube to facilitate insertion of the introducer stylet into the central opening and into the distal elongate hypotube of the introducer cannula. The proximal handle of the introducer cannula includes one or more slots configured to receive at least a portion of the proximal handle of the introducer stylet so as to facilitate engagement and alignment between the introducer stylet and the introducer cannula. The proximal handle of the introducer stylet includes an anti-rotation tab configured to be received within one of the one or more slots so as to prevent rotation of the introducer stylet within the introducer cannula. A distal end of the distal elongate shaft of the introducer stylet includes a distal cutting tip and a scalloped section proximal to the distal cutting tip so as to provide gaps between an outer diameter of the distal end of the distal elongate shaft and the inner diameter of the introducer cannula.

In some embodiments, the proximal handle of the introducer stylet further includes a press button that, when pressed: (a) disengages the anti-rotation tab and allows for rotation of the introducer stylet within the introducer stylet, and (b) allows for removal of the introducer stylet from the introducer cannula. The proximal handle of the introducer stylet may include a ramp configured to provide a mechanical assist for removal of the introducer stylet from the introducer cannula. The proximal handle of the introducer cannula may comprise a T-shaped, or smokestack shaped, design.

The introducer system may further include a curved cannula assembly. The curved cannula assembly may include a cannula comprising a proximal handle with a curved insertion slot and a distal polymeric tube. The distal polymeric tube may include a curved distal end portion having a preformed curvature but configured to bend when placed under constraint (e.g., constraint by insertion through a straight introducer cannula). The curved cannula assembly may further include a stylet comprising a proximal handle and a distal elongate shaft. The distal elongate shaft includes a curved distal end portion having a preformed curvature but configured to bend when placed under constraint (e.g., constraint by insertion through a cannula or bone tissue) and a distal channeling tip. A length of the curved distal end portion of the distal elongate shaft proximal to the distal channeling tip (e.g., a springboard or platform portion) may comprise a cross-section circumference profile that is less than a full cross-section circumference profile (e.g., cross-section circumference profile of neighboring or adjacent portions of the distal elongate shaft or of the distal channeling tip), such that there is a larger gap between an outer cross-sectional dimension of the curved distal end portion of the distal elongate shaft and the inner diameter of the curved distal end portion of the cannula along the length of the curved distal end portion of the distal elongate shaft proximal to the distal channeling tip. The less than full cross-section circumference profile may comprise a "D" shape. The overall cross-section circumference profile may thus be asymmetric (e.g., not uniform or constant along its entire length).

The proximal handle of the stylet may include a bail mechanism comprises a bail actuator that is adapted to cause axial movement (e.g., proximal movement upon actuation) of the distal channeling tip of the distal elongate shaft of the stylet with respect to the cannula so as to facilitate insertion of the curved cannula assembly through the introducer cannula and withdrawal of the stylet of the curved cannula assembly from the cannula of the curved cannula assembly after formation of a curved path within the bone.

The introducer system may further include an introducer drill adapted to be introduced into and through the introducer cannula to form a further path within the bone after removal of the introducer stylet from the introducer cannula. The introducer drill may include a fluted distal portion and a distal drill tip, wherein drill flutes of the fluted distal portion taper away (e.g., flutes go from higher volume to lower volume) from the distal drill tip so as to facilitate improved bone chip packing within an open volume defined by the drill flutes as bone chips are generated by operation of the introducer drill. The aforementioned system components may be provided as a kit with instructions for use.

In accordance with several embodiments, a system configured to provide curved access within bone includes a cannula comprising a proximal handle with a curved insertion slot and a distal polymeric tube, with the distal polymeric tube including a curved distal end portion having a preformed curvature but configured to bend when placed under constraint. The system further includes a stylet comprising a proximal handle and a distal elongate shaft, wherein the distal elongate shaft includes a curved distal end portion having a preformed curvature but configured to bend when placed under constraint and a distal channeling tip. A length of the curved distal end portion of the distal elongate shaft proximal to the distal channeling tip comprises a cross-section circumference profile that is less than a full cross-section circumference profile such that there is a larger gap between an outer cross-sectional dimension of the curved distal end portion of the distal elongate shaft and the inner diameter of the curved distal end portion of the cannula along the length of the curved distal end portion of the distal elongate shaft proximal to the distal channeling tip. In some embodiments, the cross-section circumference profile comprises a "D" shape. An upper surface of the length of the curved distal end portion may be generally flat. The proximal handle of the stylet may include a bail configured to be actuated so as to cause proximal axial retraction of the stylet with respect to the cannula when the proximal handle of the stylet is engaged with the proximal handle of the cannula. In some embodiments, the curved distal end portion of the distal elongate shaft is constructed such that the preformed curvature of the curved distal end portion does not deviate by more than 20 degrees upon insertion within the bone. A maximum vertical cross-sectional dimension of the length of the curved distal end portion may be between 40% and 80% (e.g., between 40% and 60%, between 45% and 70%, between 50% and 65%, between 60% and 80%, overlapping ranges thereof, or any value within the recited ranges) of a maximum cross sectional dimension of proximal and distal regions of the curved distal end portion bordering the length of the curved distal end portion. The system components may be provided as a kit with instructions for use.

In accordance with several embodiments, a method of accessing a target treatment location within a vertebral body identified as having hard bone includes advancing an introducer assembly through skin adjacent the vertebral body and into a pedicle connected to the vertebral body, the introducer assembly including an introducer stylet inserted within an introducer cannula with a distal cutting tip of the introducer stylet extending out of the introducer cannula. The method further includes removing the introducer stylet from the introducer cannula while leaving the introducer cannula in place. The method also includes inserting an introducer drill through and beyond the introducer cannula and through the pedicle and into cancellous bone of the vertebral body. Inserting the introducer drill includes rotating the introducer drill. The introducer drill includes a fluted distal portion and a distal drill tip. The drill flutes of the fluted distal portion taper away from the distal drill tip so as to facilitate improved bone chip packing within an open volume defined by the drill flutes as bone chips are generated by operation of the introducer drill.

In accordance with several embodiments, inserting the introducer drill may involve not malleting on the introducer drill. In some embodiments, inserting the introducer drill does include malleting on a proximal handle of the introducer drill. The method may further include removing the introducer drill from the introducer cannula. The method may also include inserting a curved cannula assembly into a curved slot of a proximal handle of the introducer cannula. The curved cannula assembly may include a second cannula including a proximal handle with a curved insertion slot and a distal polymeric tube, wherein the distal polymeric tube includes a curved distal end portion having a preformed curvature but configured to bend when placed under constraint. The curved cannula assembly may also include a second stylet including a proximal handle and a distal elongate shaft. The distal elongate shaft of the second stylet includes a curved distal end portion having a preformed curvature but configured to bend when placed under constraint and a distal channeling tip. A length of the curved distal end portion of the distal elongate shaft proximal to the distal channeling tip may comprise a cross-section circumference profile that is less than a full cross-section circumference profile such that there is a larger gap between an outer cross-sectional dimension of the curved distal end portion of the distal elongate shaft and the inner diameter of the curved distal end portion of the second cannula along the length of the curved distal end portion of the distal elongate shaft proximal to the distal channeling tip.

In some embodiments, the method further includes removing the second stylet from the second cannula. The method may also include inserting a third stylet into a slot of the proximal handle of the second cannula and beyond an open distal tip of the second cannula, wherein the third stylet is configured to form a straight path (e.g., beyond a curved path formed by the curved cannula assembly) starting from the open distal tip of the second cannula toward the target treatment location, and removing the third stylet from the second cannula after formation of the straight path. The method may include inserting a treatment device into the slot of the proximal handle of the second cannula and beyond the open distal tip of the second cannula to the target treatment location and performing therapy at the target treatment location using the treatment device. The therapy may include ablating at least 75% of the branches of a basivertebral nerve within the bone (e.g., vertebral body).

Several embodiments of the invention have one or more of the following advantages: (i) increased treatment accuracy; (ii) increased efficacy and enhanced safety; (iii) increased efficiency; (iv) increased precision; (v) synergistic results; (vi) "one-and-done" procedure that does not require further surgical intervention; (vii) treatment of chronic low back pain; (viii) prevention of pain due to early detection of factors likely to cause pain in the future; (ix) reduction of unwanted stoppages or interruptions in treatment procedure (x) ease of use (e.g., due to reduced friction or force).

For purposes of summarizing the disclosure, certain aspects, advantages, and novel features of embodiments of the disclosure have been described herein. It is to be understood that not necessarily all such advantages may be achieved in accordance with any particular embodiment of the disclosure provided herein. Thus, the embodiments disclosed herein may be embodied or carried out in a manner that achieves or optimizes one advantage or group of advantages as taught or suggested herein without necessarily achieving other advantages as may be taught or suggested herein.

The methods summarized above and set forth in further detail below describe certain actions taken by a practitioner; however, it should be understood that they can also include the instruction of those actions by another party. Thus, actions such as "For example, actions such as "applying thermal energy" include "instructing the applying of thermal energy." Further aspects of embodiments of the disclosure will be discussed in the following portions of the specification. With respect to the drawings, elements from one figure may be combined with elements from the other figures.

BRIEF DESCRIPTION OF THE DRAWINGS

Several embodiments of the disclosure will be more fully understood by reference to the following drawings which are for illustrative purposes only:

FIG. 3Z illustrates the introducer drill inserted fully within the introducer cannula.

FIGS. 3AA-3HH illustrate various steps of a method of accessing and treating tissue within a vertebral body using one or more of the access tools of the kit or system of FIG. 3.

DETAILED DESCRIPTION

Figure 1:
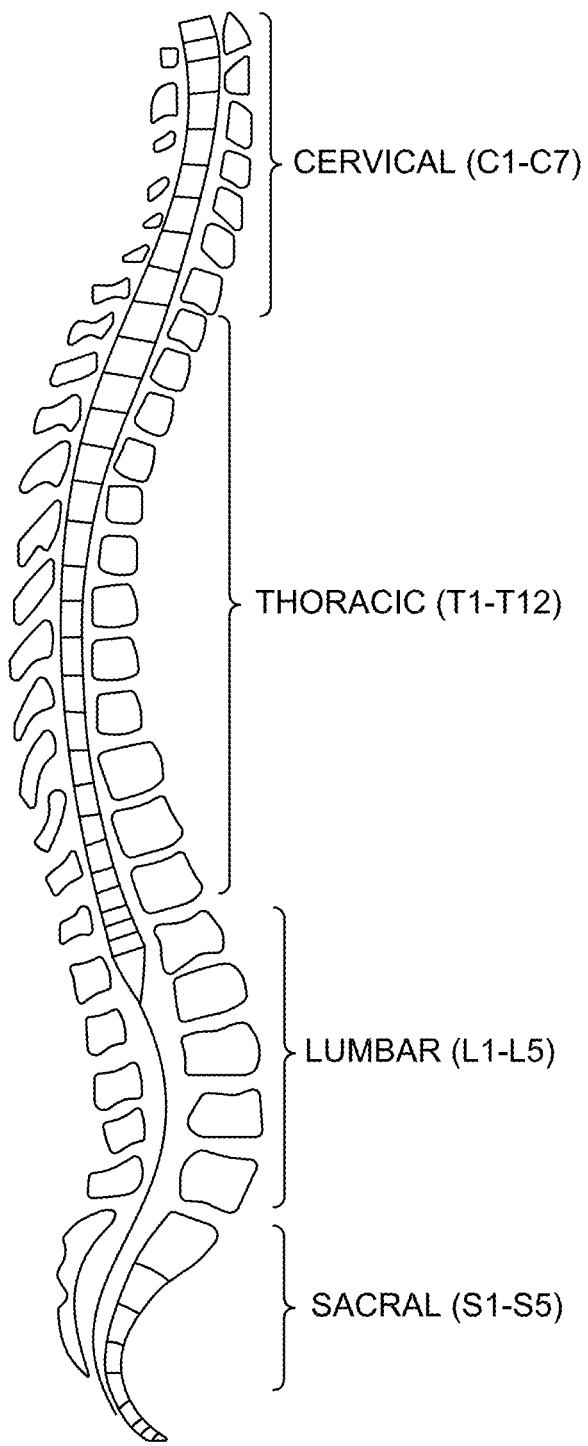
FIG. 1 illustrates various vertebral levels and vertebrae that may be treated by the systems and methods described herein.

Several implementations described herein are directed to systems and methods for modulating nerves within or adjacent (e.g., surrounding) bone. In some implementations, an intraosseous nerve (e.g., basivertebral nerve) within a bone (e.g., vertebral body) of the spine is modulated for treatment, or prevention of, chronic back pain. The vertebral body may be located in any level of the vertebral column (e.g., cervical, thoracic, lumbar and/or sacral). FIG. 1 schematically illustrates a vertebral column and the various vertebral segments or levels. Multiple vertebral bodies may be treated in a single visit or procedure (simultaneously or sequentially). The multiple vertebral bodies may be located in a single spine segment (e.g., two adjacent vertebral bodies in the sacral spine segment (e.g., S1 and S2) or lumbar spine segment (e.g., L3, L4 and/or L5) or thoracic spine segment or cervical spine segment) or in different spine segments (e.g., an L5 vertebra in the lumbar spine segment and an S1 vertebra in the sacral spine segment). Intraosseous nerves within bones other than vertebral bodies may also be modulated. For example, nerves within a humerus, radius, femur, tibia, calcaneus, tarsal bones, hips, knees, and/or phalanges may be modulated.

In some implementations, the one or more nerves being modulated are extraosseous nerves located outside the vertebral body or other bone (e.g., at locations before the nerves enter into, or after they exit from, a foramen of the bone). Other tissue in addition to, or alternative to, nerves may also be treated or otherwise affected (e.g., tumors or other cancerous tissue or fractured bones). Portions of nerves within or on one or more vertebral endplates or intervertebral discs between adjacent vertebral bodies may be modulated.

The modulation of nerves or other tissue may be performed to treat one or more indications, including but not limited to chronic low back pain, upper back pain, acute back pain, joint pain, tumors in the bone, and/or bone fractures. The modulation of nerves may also be performed in conjunction with bone fusion or arthrodesis procedures so as to provide synergistic effects or complete all-in-one, "one-and-done" treatment that will not require further surgical or minimally invasive interventions.

In some implementations, fractures within the bone may be treated in addition to denervation treatment and/or ablation of tumors by applying heat or energy and/or delivering agents or bone filler material to the bone. For example, bone morphogenetic proteins and/or bone cement may be delivered in conjunction with vertebroplasty or other procedures to treat fractures or promote bone growth or bone healing. In some implementations, energy is applied and then agents and/or bone filler material is delivered in a combined procedure. In some aspects, vertebral compression fractures (which may be caused by osteoporosis or cancer) are treated in conjunction with energy delivery to modulate nerves and/or cancerous tissue to treat back pain.

In accordance with several implementations, the systems and methods of treating back pain or facilitating neuromodulation of intraosseous nerves described herein can be performed without surgical resection, without general anesthesia, without cooling (e.g., without cooling fluid), and/or with virtually no blood loss. In some embodiments, the systems and methods of treating back pain or facilitating neuromodulation of intraosseous nerves described herein facilitate easy retreatment if necessary. In accordance with several implementations, successful treatment can be performed in challenging or difficult-to-access locations and access can be varied depending on bone structure or differing bone anatomy. One or more of these advantages also apply to treatment of tissue outside of the spine (e.g., other orthopedic applications or other tissue).

Access to the Vertebral Body

Methods of Access

Various methods of access may be used to access a vertebral body or other bone. In some implementations, the vertebral body is accessed transpedicularly (through one or both pedicles). In other implementations, the vertebral body is accessed extrapedicularly (e.g., without traversing through a pedicle). In some implementations, the vertebral body is accessed using an extreme lateral approach or a transforaminal approach, such as used in XLIF and TLIF interbody fusion procedures. In some implementations, an anterior approach is used to access the vertebral body.

Figure 2:
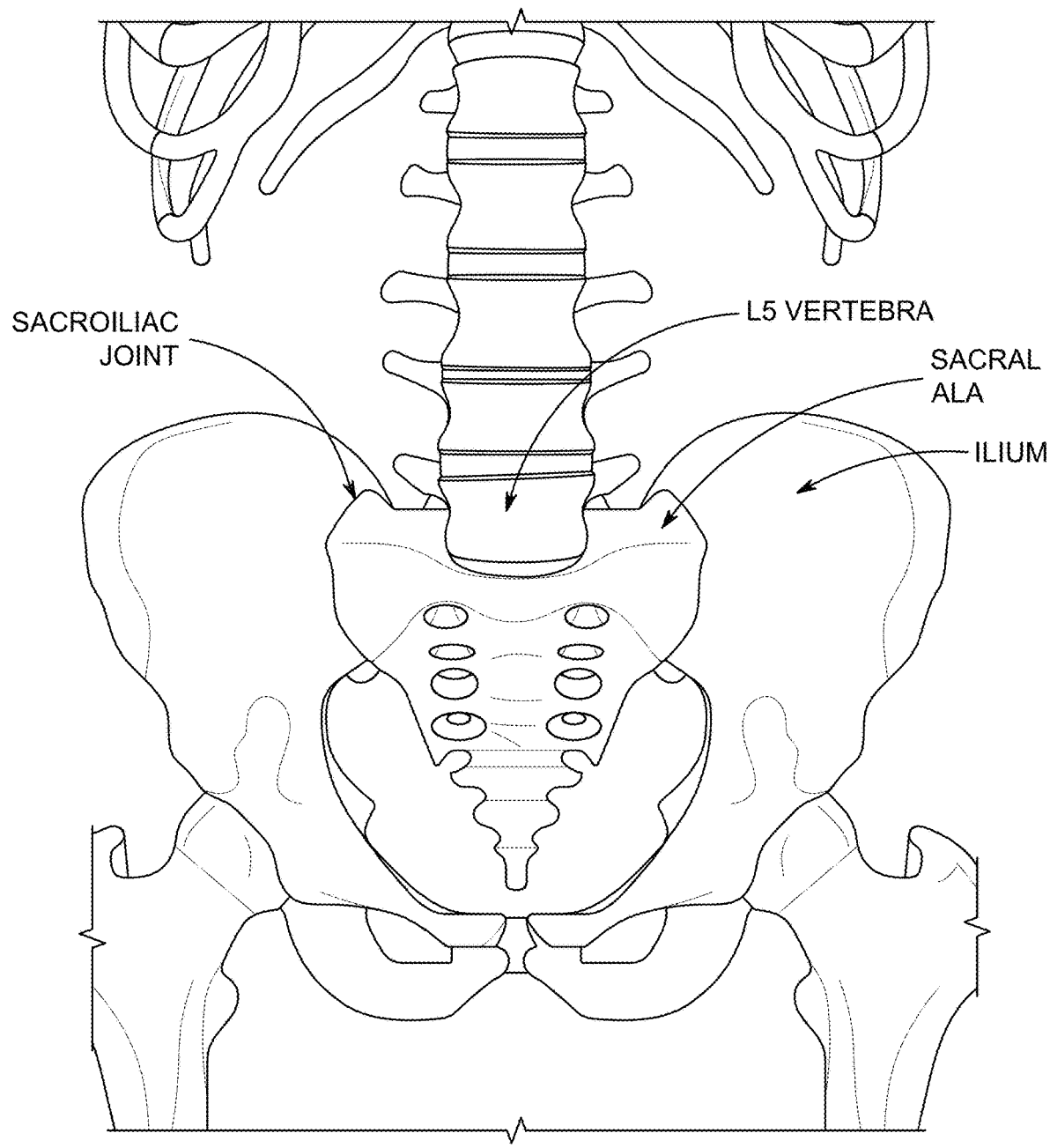
FIG. 2 illustrates pelvic bones of a human to illustrate potential methods of accessing certain vertebral bodies.

Certain vertebrae in the sacral or lumbar levels (e.g., S1 vertebra, L5 vertebra) may also be accessed generally posterolaterally using a trans-ilium approach (e.g., an approach through an ilium bone). With reference to FIG. 2, an access hole may be formed through the ilium at a location designed to facilitate access to the vertebral body or bodies in the sacral or lumbar region. For example, access tools (e.g., an introducer assembly including a cannula/stylet combination) may be delivered through an ilium and/or sacroiliac joint or sacral ala into an S1 vertebra under image guidance (e.g., CT image guidance and/or fluoroscopy) and/or using stereotactic or robotic-assisted surgical and/or navigation systems, such as the robotic system described in connection with FIG. 7. A treatment device could then be inserted through an introducer and/or other access cannula of the access tools to a target treatment location within a sacral or lumbar vertebra. A trans-ilium approach may advantageously increase the ability of the clinician to access the target treatment location in a particular portion or region of the vertebral body (e.g., posterior portion or region) that is not capable of being adequately accessed using a transpedicular approach. In some implementations, the vertebral body may be accessed directly through the cerebrospinal fluid and through the dura into a posterior region of the vertebral body.

In some implementations, the vertebral body may be accessed transforaminally through a basivertebral foramen. Transforaminal access via the spinal canal may involve insertion of a "nerve finder" or nerve locator device and/or imaging/diagnostic tool to avoid damaging spinal cord nerves upon entry by the access tools or treatment devices.

The nerve locator device may comprise a hand-held stimulation system such as the Checkpoint Stimulator and Locator provided by Checkpoint Surgical® or the EZstim® peripheral nerve stimulator/nerve locators provided by Avanos Medical, Inc. The nerve finder or nerve locator device could advantageously identify sensitive nerves that should be avoided by the access tools so as not to risk paralysis or spinal cord injury upon accessing the target treatment site. The nerve locator device may be configured to apply stimulation signals between two points or locations and then assess response to determine presence of nerves in the area between the two points or locations. The nerve locator device may include a bipolar pair of stimulation electrodes or monopolar electrodes. In some implementations, the nerve locator features may be implemented on the access tools or treatment devices themselves as opposed to a separate stand-alone device.

Access Tools and Treatment Devices

Access tools may include an introducer assembly including an outer cannula and a sharpened stylet, an inner cannula configured to be introduced through the outer cannula, and/or one or more additional stylets, curettes, or drills to facilitate access to an intraosseous location within a vertebral body or other bone. The access tools (e.g., outer cannula, inner cannula, stylets, curettes, drills) may have pre-curved distal end portions or may be actively steerable or curveable. Any of the access tools may have beveled or otherwise sharp tips or they may have blunt or rounded, atraumatic distal tips. Curved drills may be used to facilitate formation of curved access paths within bone. Any of the access tools may be advanced over a guidewire in some implementations.

The access tools may be formed of a variety of flexible materials (e.g., ethylene vinyl acetate, polyethylene, polyethylene-based polyolefin elastomers, polyetheretherketone, polypropylene, polypropylene-based elastomers, styrene butadiene copolymers, thermoplastic polyester elastomers, thermoplastic polyurethane elastomers, thermoplastic vulcanizate polymers, metallic alloy materials such as nitinol, and/or the like). Combinations of two or more of these materials may also be used. The access tools may include chevron designs or patterns or slits along the distal end portions to increase flexibility or bendability. Any of the access tools may be manually or automatically rotated (e.g., using a robotic control system as described in connection with FIG. 7) to facilitate a desired trajectory.

In some implementations, an outer cannula assembly (e.g., introducer assembly) includes a straight outer cannula and a straight stylet configured to be received within the outer cannula. The outer cannula assembly may be inserted first to penetrate an outer cortical shell of a bone and provide a conduit for further access tools to the inner cancellous bone. An inner cannula assembly may include a cannula having a pre-curved or steerable distal end portion and a stylet having a corresponding pre-curved or steerable distal end portion. Multiple stylets having distal end portions with different curvatures may be provided in a kit and selected from by a clinician. The inner cannula assembly may alternatively be configured to remain straight and non-curved.

Figure 3:
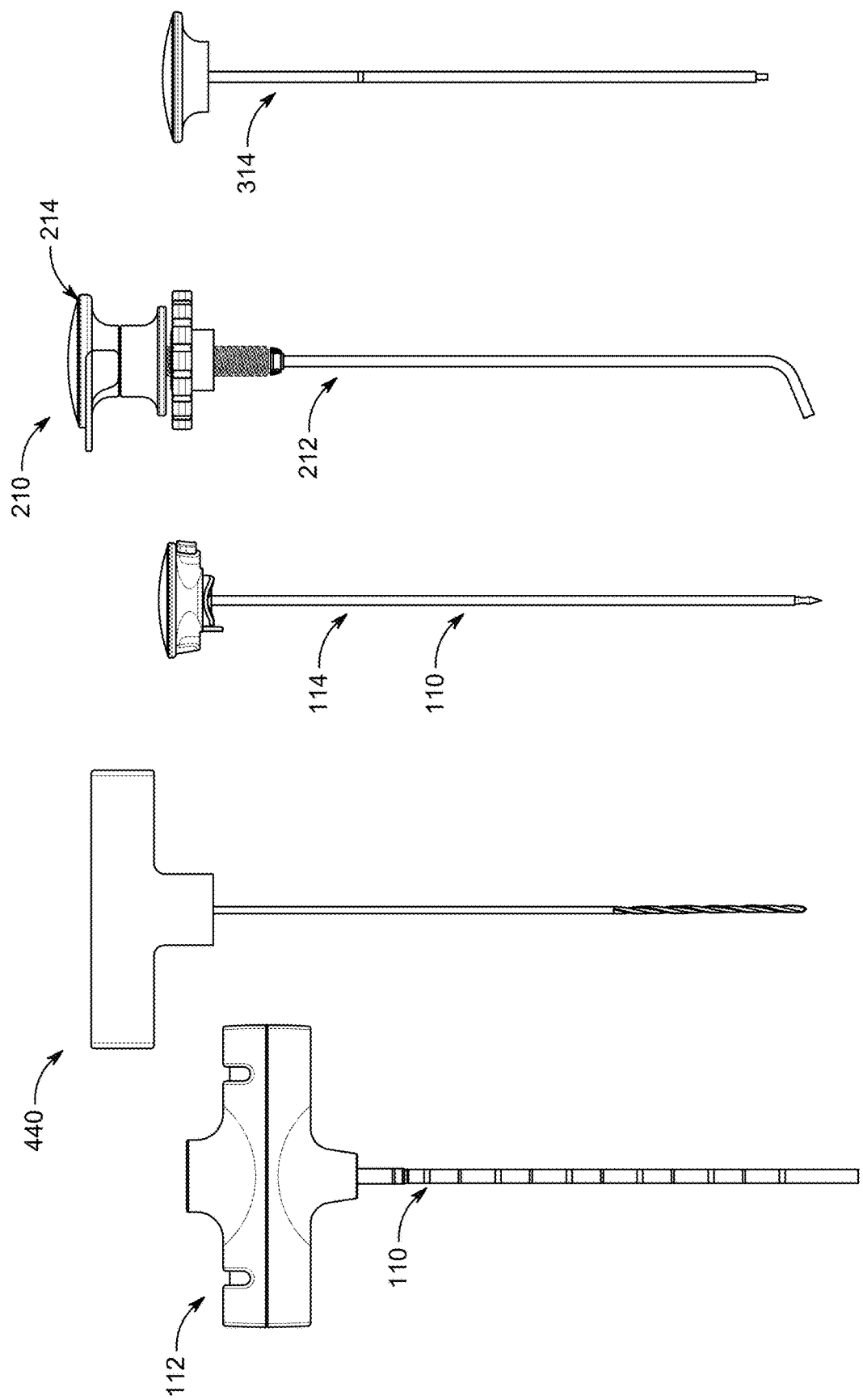
FIG. 3 illustrates an example kit or system of access tools configured to access a vertebral body.

With reference to FIG. 3, in one implementation, a kit or system of access tools includes an introducer assembly 110 comprised of an introducer cannula 112 and an introducer stylet 114, a curved cannula assembly 210 comprised of a curved cannula 212 and a J-stylet 214, and a straight stylet 314. The introducer stylet 114 may be bevel tipped, trocar tipped, and/or diamond tipped. The introducer stylet 114 is configured to be received in a lumen of the introducer cannula 112 in a manner such that a distal tip of the introducer stylet 114 protrudes from an open distal tip of the introducer cannula 112, thereby forming the introducer assembly 110 in combination. The J-stylet 214 is configured to be received in a lumen of the curved cannula 212 in a manner such that a distal tip of the J-stylet 214 protrudes from an open distal tip of the curved cannula 212, thereby forming the curved cannula assembly 210 in combination. The curved cannula 212 and the J-stylet 214 may each comprise a straight proximal main body portion and a curved distal end portion. The curves of the curved distal end portions of the curved cannula 212 and the J-stylet 214 may correspond to each other. The straight stylet 314 is a flexible channeling stylet configured to be delivered through the curved cannula 212 and then to form and maintain a straight or generally straight path upon exiting the open distal tip of the curved cannula 212.

The access tools may be provided as a kit that may optionally additionally include one or more additional introducer cannulas, one or more additional introducer stylets (e.g., with different tips, such as one with a bevel tip and one with a diamond or trocar tip), one or two or more than two additional curved cannulas (e.g., having a curved distal end portion of a different curvature than a first curved cannula), an additional J-stylet (e.g., having a different curvature or different design configured to access hard bone), an introducer drill 440, and/or an additional straight stylet (e.g., having a different length than the first straight stylet.

In some embodiments, the access tools (e.g., kit) may be specifically designed and adapted to facilitate access to hard, non-osteoporotic bone (e.g., bone surrounding or within a vertebral body, such as a cervical vertebra, a thoracic vertebra, a lumbar vertebra, or a sacral vertebra). Hard bone may be determined based on bone mass density testing, compressive strength determinations, compressive modulus determinations, imaging modalities, or based on tactile feel by the operator as access instruments are being advanced. In some implementations, hard bone may be determined as bone having a bone mineral density score within a standard deviation of a normal healthy young adult (e.g., a T score greater than or equal to −1). In some implementations, hard bone may be identified as bone having a compressive strength of greater than 4 MPa and/or a compressive modulus of greater than 80 MPa for cancellous bone and greater than 5.5 MPa and/or a compressive modulus of greater than 170 MPa for cortical bone. Some kits may include at least two of every access instrument. Some kits may include optional add-on components or accessory kit modules for accessing hard bone (e.g., the introducer drill 440 and J-stylet 214 specially configured to access hard bone). Some kits may include optional additional access tool components or accessory kit modules adapted to access one or more additional vertebrae in the same spinal segment or in different spinal segments. The kit may also include one or more (e.g., at least two) treatment devices (such as radiofrequency energy delivery probes).

Figure 3A:
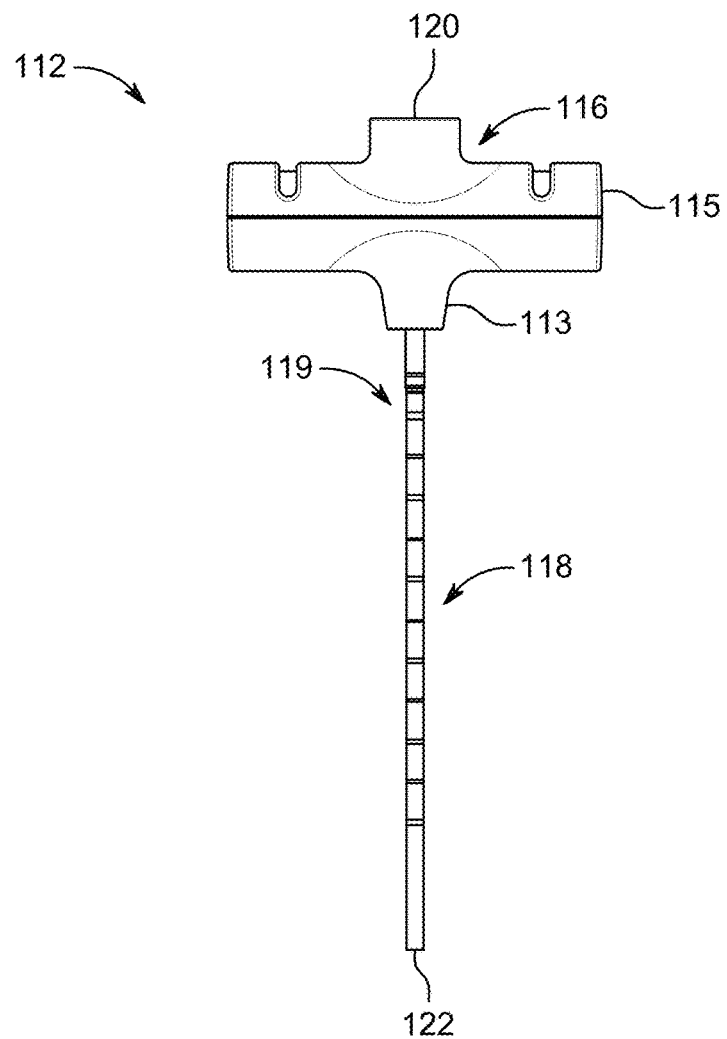
FIGS. 3A-3C include various views of an introducer cannula of the kit or system of FIG. 3.
Figure 3B:
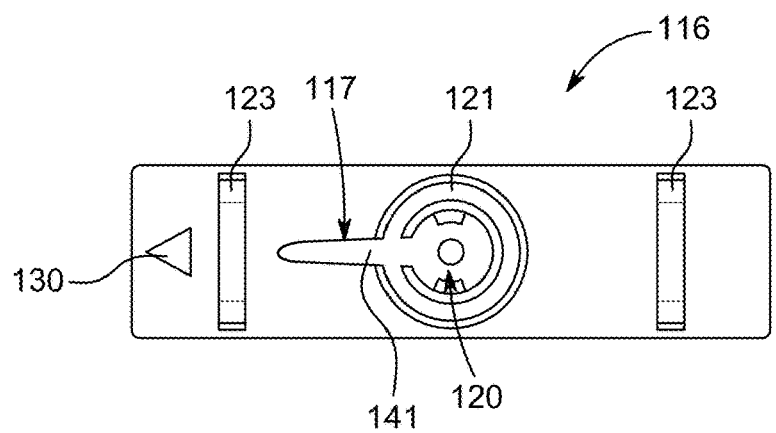
Figure 3C:
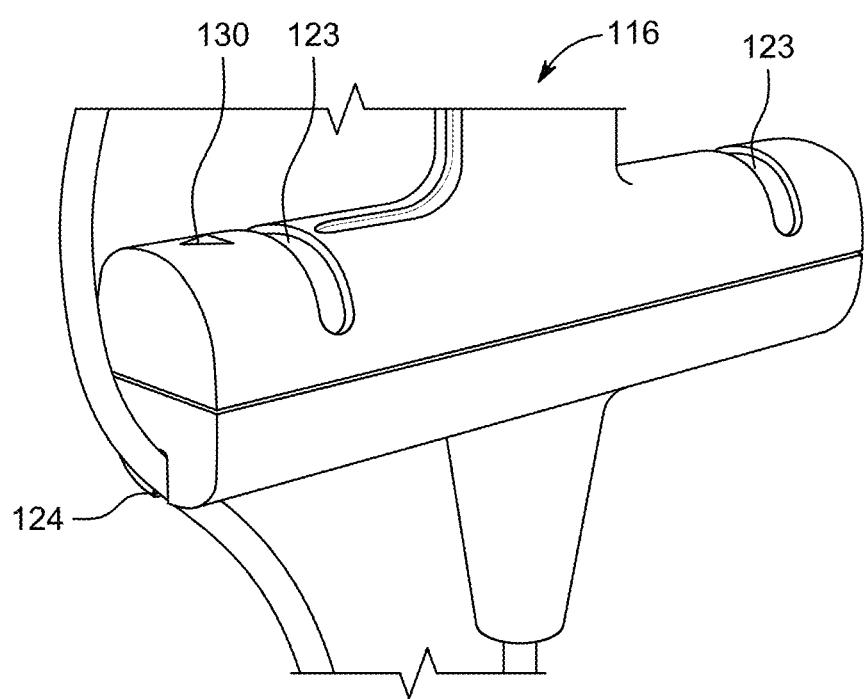

FIGS. 3A-3C illustrate various views of an embodiment of the introducer cannula 112. The introducer cannula 112 includes a proximal handle 116 and a distal hypotube 118 extending from the proximal handle 116. The illustrated proximal handle 116 comprises a "smokestack" or "T-Handle" design configuration adapted to provide sufficient finger clearance and gripping (e.g., two fingers on each side of a lower flange 113 of the proximal handle 116 and along the lower surface of a crossbar portion 115) to facilitate removal. However, alternative design configurations for the proximal handle other than a "smokestack" or "T-handle" design may be incorporated.

The proximal handle 116 includes an upper central opening 120 configured to facilitate straight axial insertion of an introducer stylet 114 or other straight access tool. The upper central opening 120 may be positioned so as to correspond with (e.g., be coaxial with) a central lumen extending through the hypotube 118 of the introducer cannula 112 so as to facilitate insertion of straight instruments (e.g., introducer stylet 114 or steerable cannulas or steerable stylets) therethrough. The proximal handle 116 may also include coupling features 121 (e.g., recesses, notches, grooves, tabs) to facilitate coupling or mating of a proximal handle 216 of the introducer stylet 114 with the proximal handle 116 of the introducer cannula 112. The coupling features 121 may be adapted to prevent rotation of the introducer stylet 114 and/or to provide assurance that a distal tip 125 of the introducer stylet 114 extends beyond an open distal tip 122 of the hypotube 118 of the introducer cannula 112 so as to enable penetration of the distal tip 125 of the introducer stylet 114 through bone. The upper surface of the proximal handle 116 of the introducer cannula 112 also includes a curved lateral slot 117 and curved ramp 141 to facilitate insertion of the curved cannula assembly 210 into the proximal handle 116 and then into and along the central lumen of the hypotube 118.

The central lumen of the hypotube 118 extends from the proximal handle 116 to the open distal tip 122 of the hypotube 118. The hypotube 118 may be flared or tapered such that the diameter of the hypotube 118 is not constant along its entire length. For example, the diameter may decrease abruptly at a certain distance (e.g., 1 cm-3 cm) from a lower edge of the lower flange 113 of the proximal handle 116 and then continue with a constant diameter distally of an abrupt flare 119. In another embodiment, the diameter may decrease gradually (e.g., taper uniformly) along the length of the hypotube 118 from the start of the flare 119 to the open distal tip 122 of the hypotube 118. The central lumen of the hypotube 118 may be coated with a medical grade silicone lubricant to improve tool insertion and removal. The outer diameter of the hypotube 118 may range from 4.2 mm to 4.5 mm.

The proximal handle 116 of the introducer cannula 112 may also include an overdrive indication mechanism configured to indicate when the curved cannula assembly 210 has been fully deployed from the introducer cannula such that further advancement of the curved cannula would place the curved cannula assembly 210 at risk of being overdriven from the introducer cannula 112, which could result in damage to the curved cannula assembly 210. The overdrive indication mechanism may comprise two slots 123 in the upper surface of the crossbar portion 115 of the proximal handle 116 that display a bi-stable (i.e., on-off states) indicator of a first color when overdrive is likely not a risk and a second color when overdrive is likely a risk (e.g., curved cannula assembly 210 has been fully deployed). In accordance with several embodiments, there are advantageously two distinct states of operation and there is no transition zone between the two states. The overdrive indication mechanism may be configured to be activated only when a gear wheel 221 of the curved cannula assembly 210 is bottomed out (e.g., fully engaged with the proximal handle 116 of the introducer cannula 112). As shown in FIG. 3C, a lower (bottom) side surface of the proximal handle 116 of the introducer cannula may include a cutout 124 adapted to receive a portion of a flexible shaft of a treatment device (e.g., radiofrequency probe comprised of nitinol or other flexible or shape memory material) and hold it in place and out of the way during a treatment procedure, thereby reducing stack height (e.g., by approximately 3 inches (or approximately 75 mm) or more).

Figure 3D:
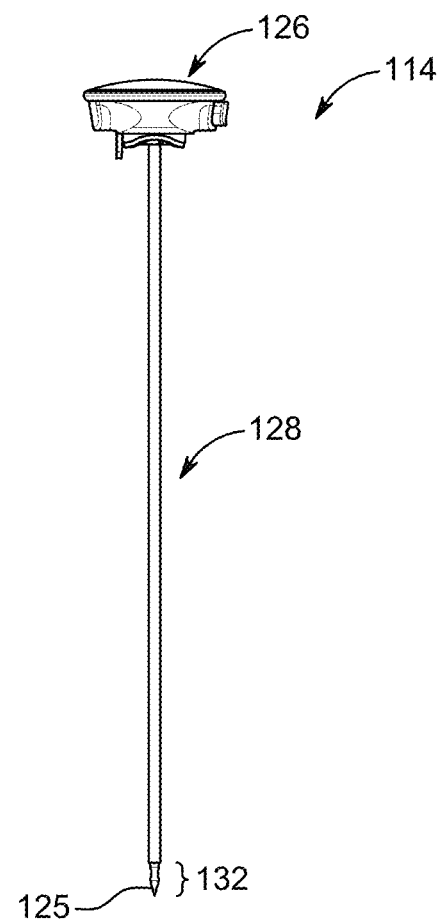
FIG. 3D is a side view of an introducer stylet of the kit or system of FIG. 3

FIGS. 3D-3H illustrate various views and portions of embodiments of introducer stylets 114. FIG. 3D illustrates a side view of an introducer stylet 114. The introducer stylet 114 includes a proximal handle 126 and a distal elongate member or shaft 128. The proximal handle 126 comprises an upper surface that is adapted for malleting by a mallet and a lower surface that is adapted to facilitate removal of the introducer stylet 114 by an operator. The length of the distal elongate member 128 may range from 8 mm to 14 mm (e.g., 8 mm, 8.5 mm, 9 mm, 9.5 mm, 10 mm, 10.5 mm, 11 mm, 11.5 mm, 12 mm, 12.5 mm, 13 mm, 13.5 mm, 14 mm). The distal end portion 132 of the introducer stylet 114 may comprise a scalloped section 133 (as shown more closely in FIG. 3E) to provide a release mechanism for bone compaction. The scalloped section 133 may be designed to have a side profile shaped generally like an hourglass. The scalloped section 133 may gradually taper from a full diameter proximal portion to a narrow-most middle portion and then gradually taper back to a full diameter distal portion. The taper may be symmetric or asymmetric. The scalloped section 133 may comprise one scallop (or scooped-out region) or multiple scallops (or scooped-out regions) along the length of the distal end portion 132. A distal tip 125 of the distal end portion 132 may comprise a full diameter so as to be adapted to break apart bone (e.g., pedicle bone, cortical bone of a vertebral body). As the bone is broken up by the distal tip 125 of the distal end portion 132, bone shards or chips can pack into a gap formed between the distal end portion 132 of the introducer stylet 114 and the inner surface of the distal end portion of the introducer cannula 112, thereby making it more difficult for the introducer stylet 114 to be removed from the introducer cannula 112. In accordance with several embodiments, the scalloped section 133 of the introducer stylet 114 advantageously provides the bone shards and fragments a place to fall into during removal of the introducer stylet 114 so as to facilitate easier removal of the introducer stylet 114.

Figure 3E:
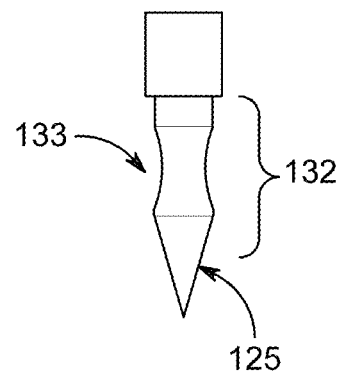
FIG. 3E is a side view of a distal cutting tip of an introducer stylet.
Figure 3H:
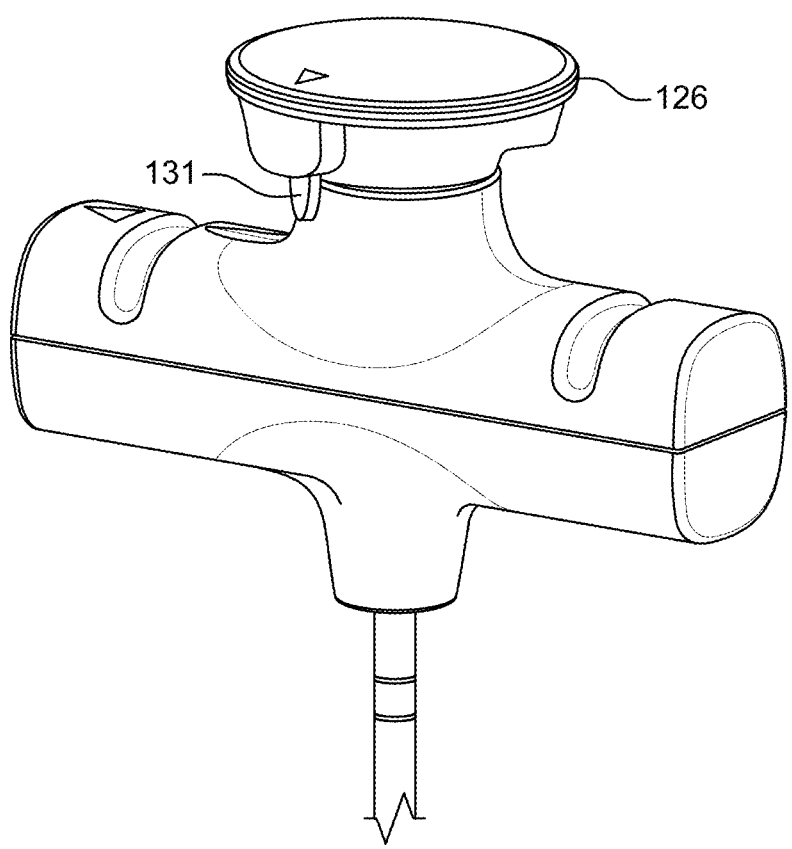
FIGS. 3F-3H illustrate a proximal portion of an introducer assembly of the kit or system of FIG. 3.
Figure 3I:
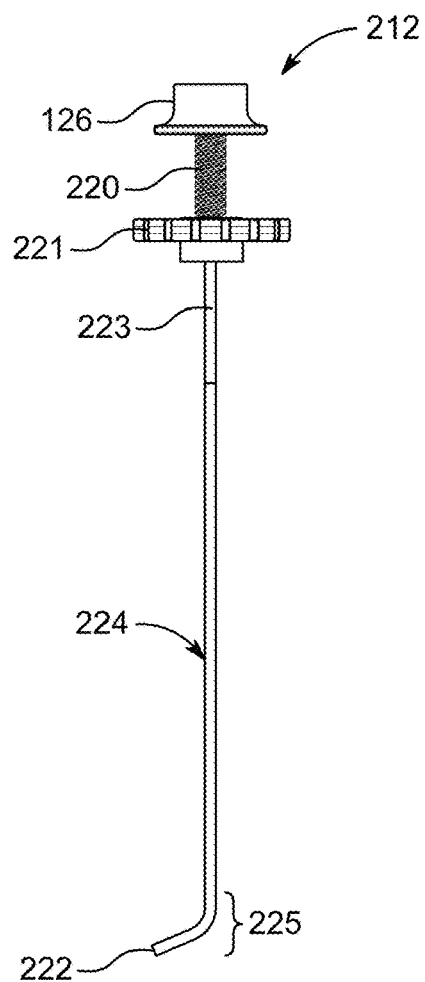
FIG. 3I is a side view and FIG. 3J is a top view of a curved cannula of the kit or system of FIG. 3.
Figure 3J:
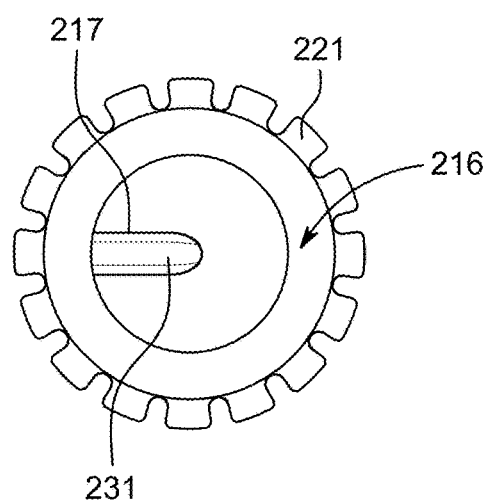
Figure 3M:
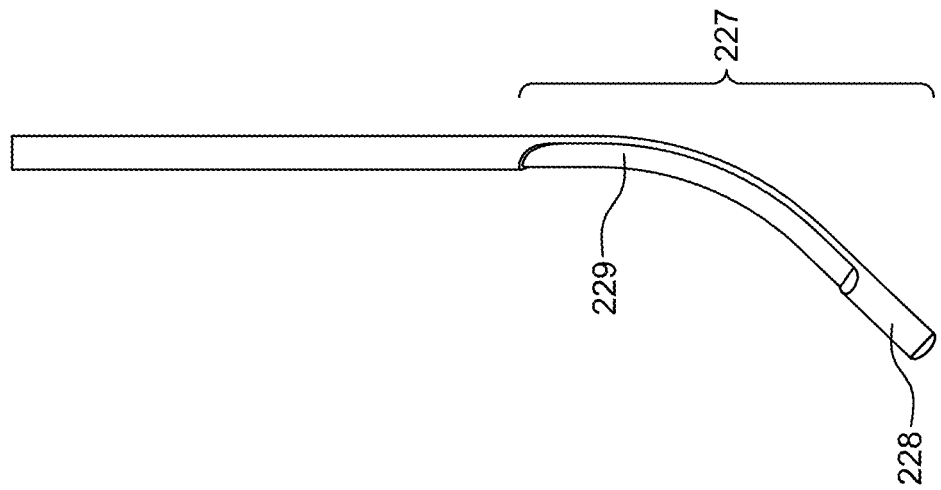
FIG. 3K is a side view of a J-stylet of the kit or system of FIG. 3 and FIGS. 3L and 3M show a side view and a perspective view of a curved distal end portion of the J-stylet of FIG. 3K.
FIGS. 3N and 3O illustrate insertion of the J-stylet of FIGS. 3K-3M into the curved cannula of FIGS. 3I and 3J.
FIG. 3P illustrates insertion of the curved cannula assembly of the kit or system of FIG. 3 into the introducer cannula of FIGS. 3A-3C.
FIG. 3Q is a side cross-section view of a proximal portion of the introducer cannula and the curved distal end portions of the curved cannula assembly.
FIGS. 3R and 3S illustrate operation of a gear wheel of the curved cannula of FIGS. 3I and 3J in connection with insertion of the curved cannula assembly into the introducer cannula.
FIGS. 3T and 3U illustrate operation of a bail of the J-stylet of FIGS. 3K-3M to facilitate insertion and retraction of the J-stylet from the curved cannula.
FIG. 3V is a side view of a straight stylet of the kit or system of FIG. 3
FIG. 3W is side cross-section view of a distal end portion of the straight stylet.
FIGS. 3X-3Z illustrate an optional introducer drill of the kit or system of FIG. 3.
Figure 3L:
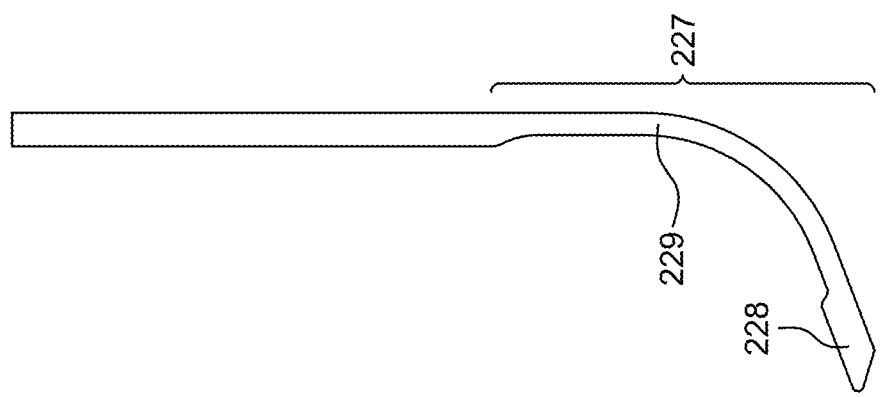
Figure 3K:
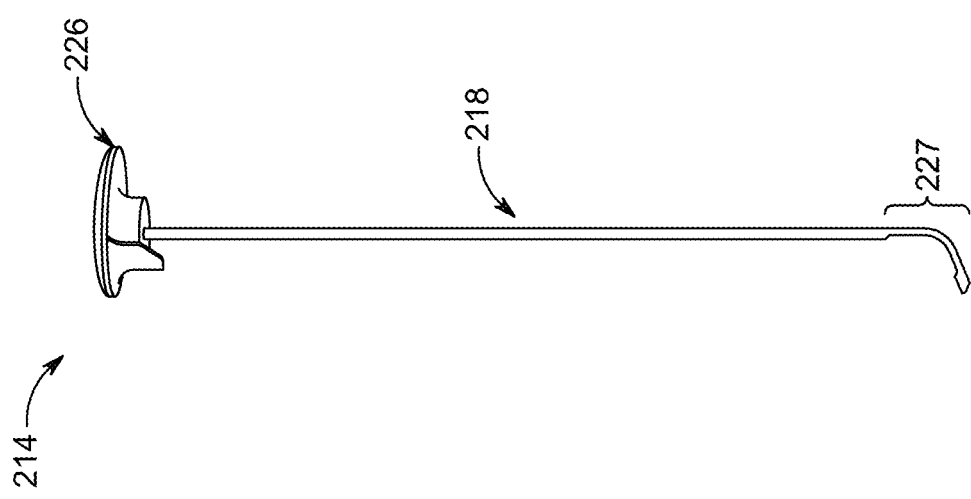
Figure 3O:
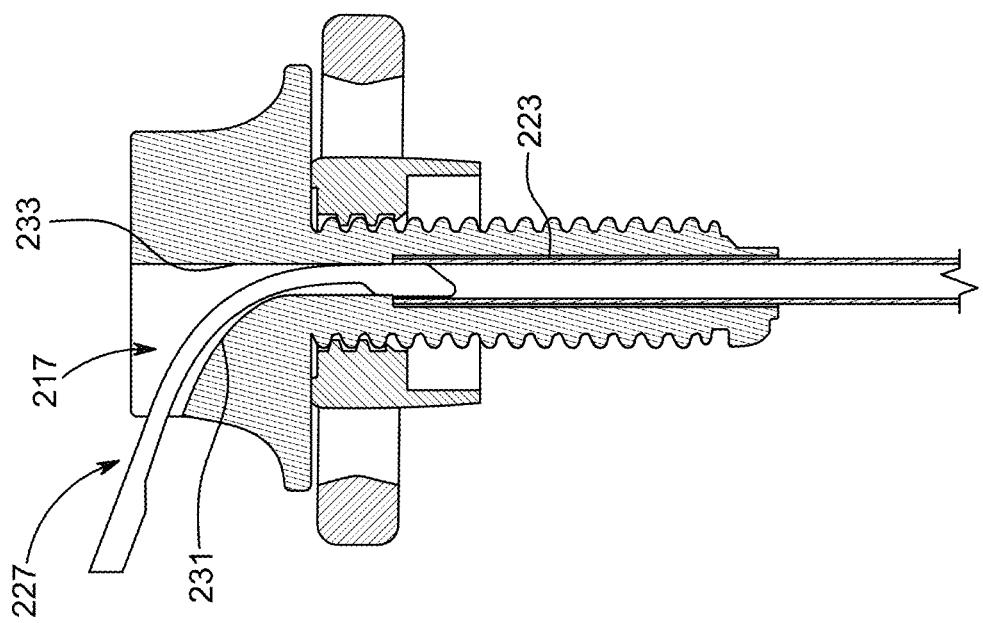
Figure 3N:
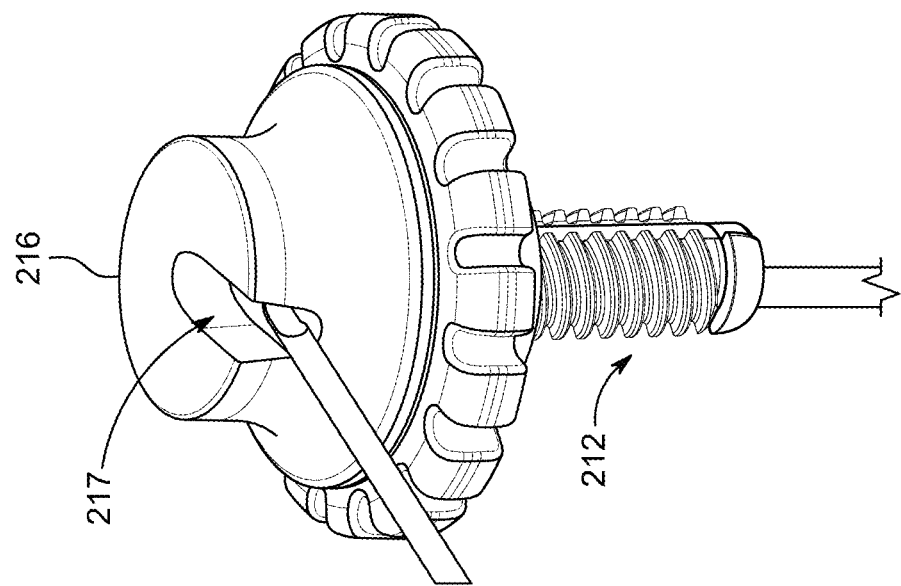
Figure 3P:
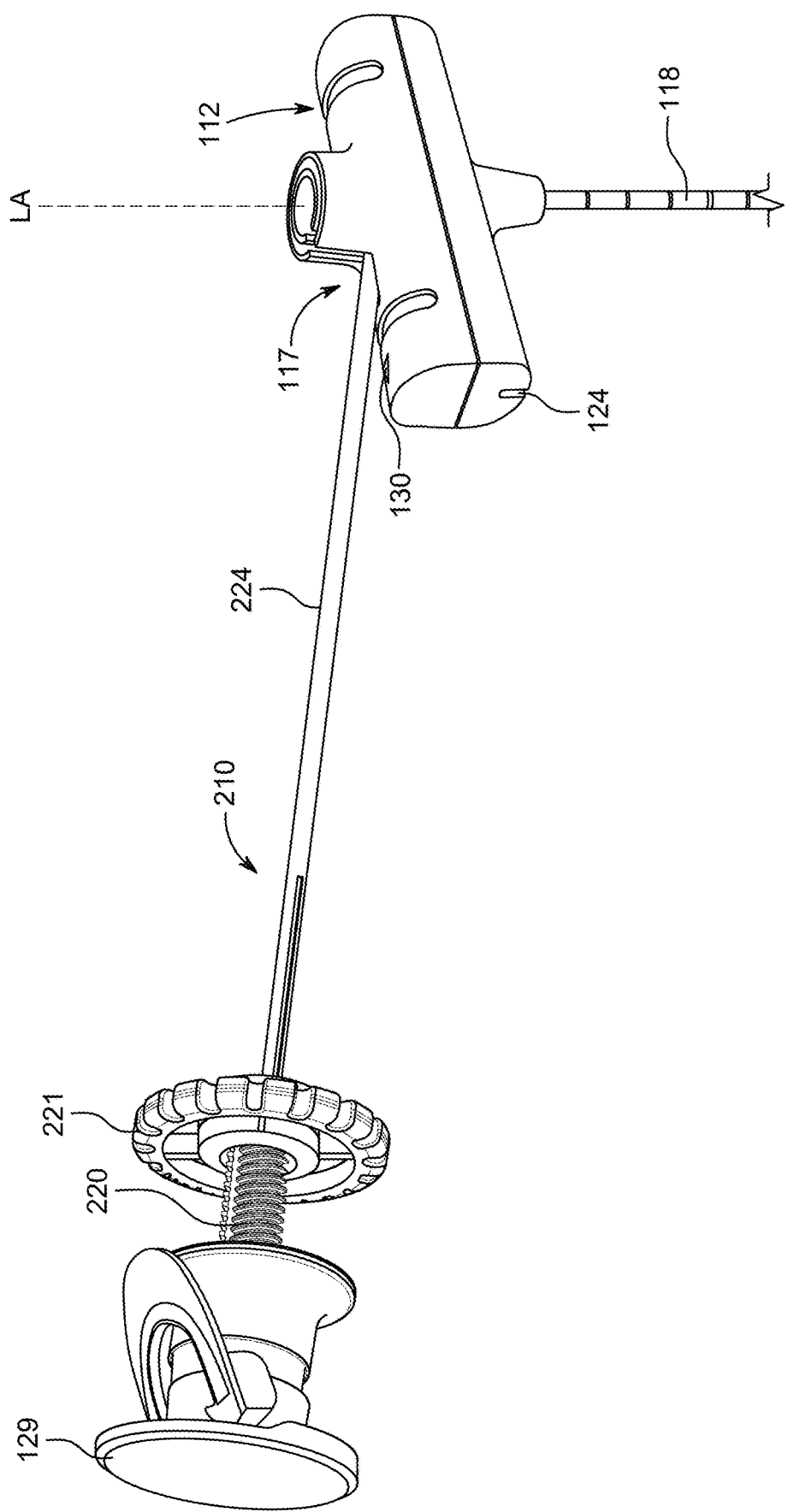
Figure 3Q:
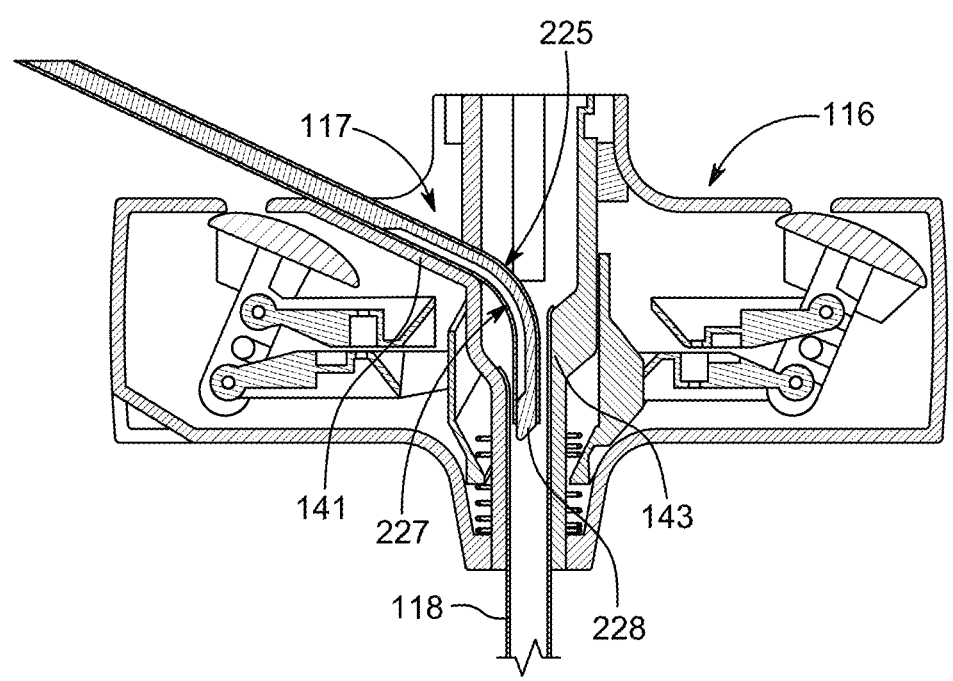
Figure 3S:
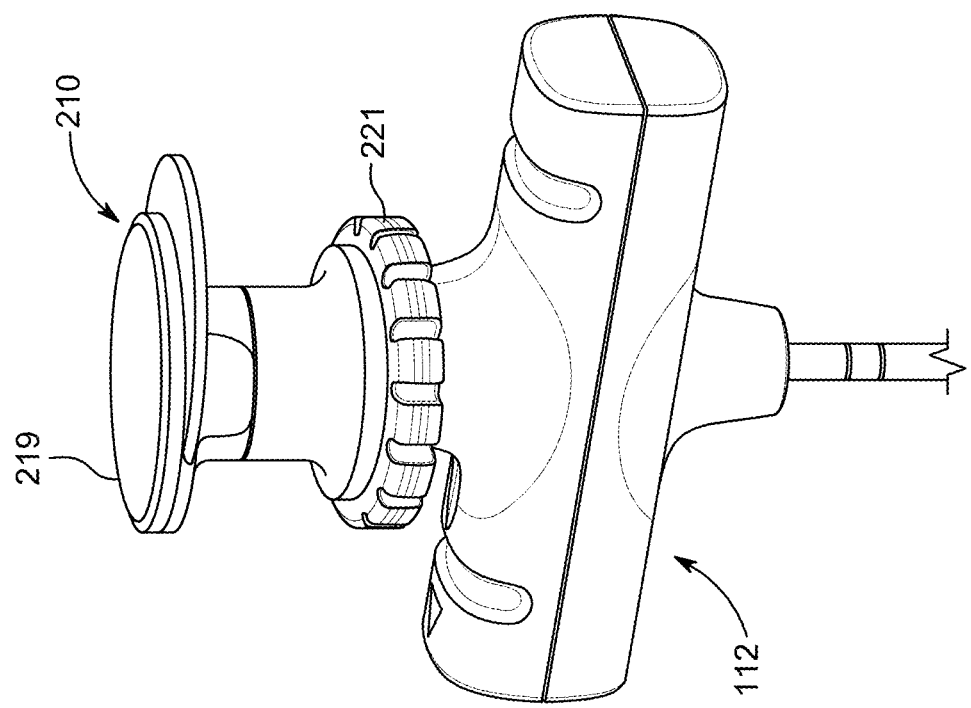
Figure 3R:
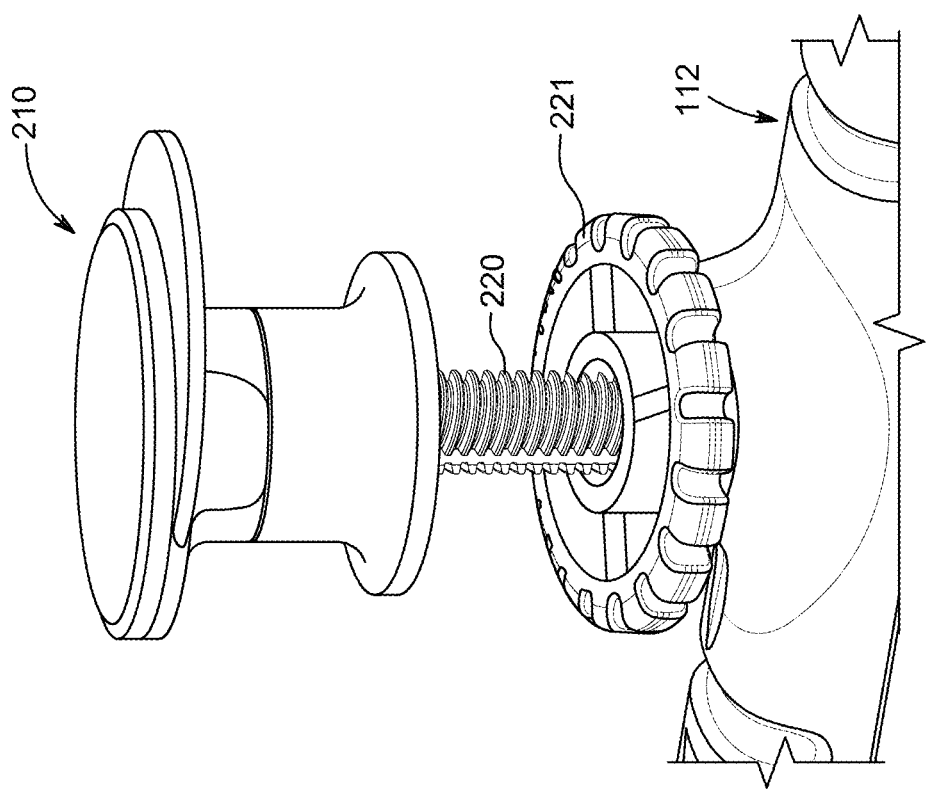
Figure 3U:
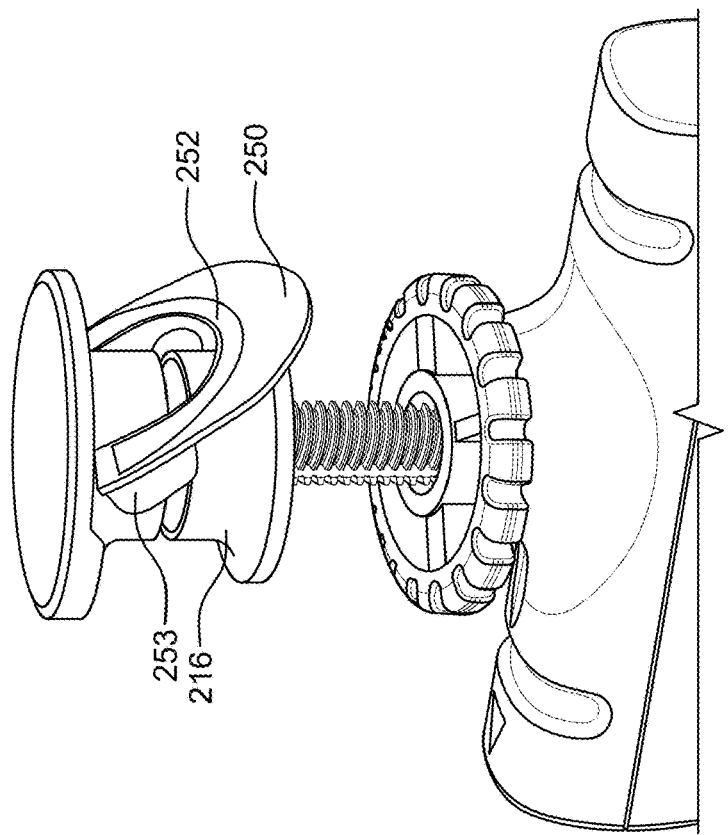
Figure 3T:
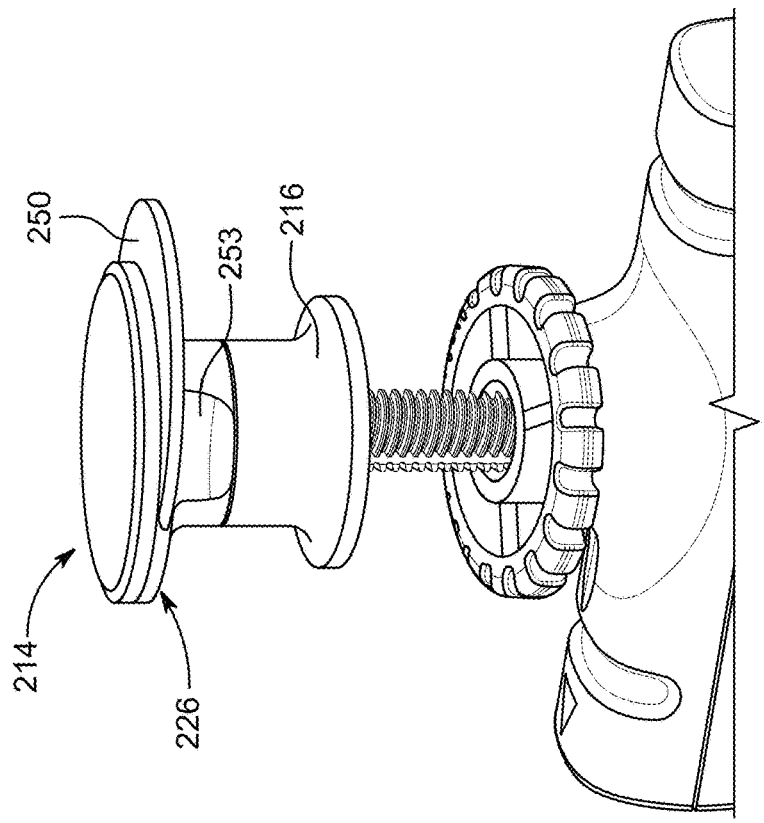
Figure 3V:
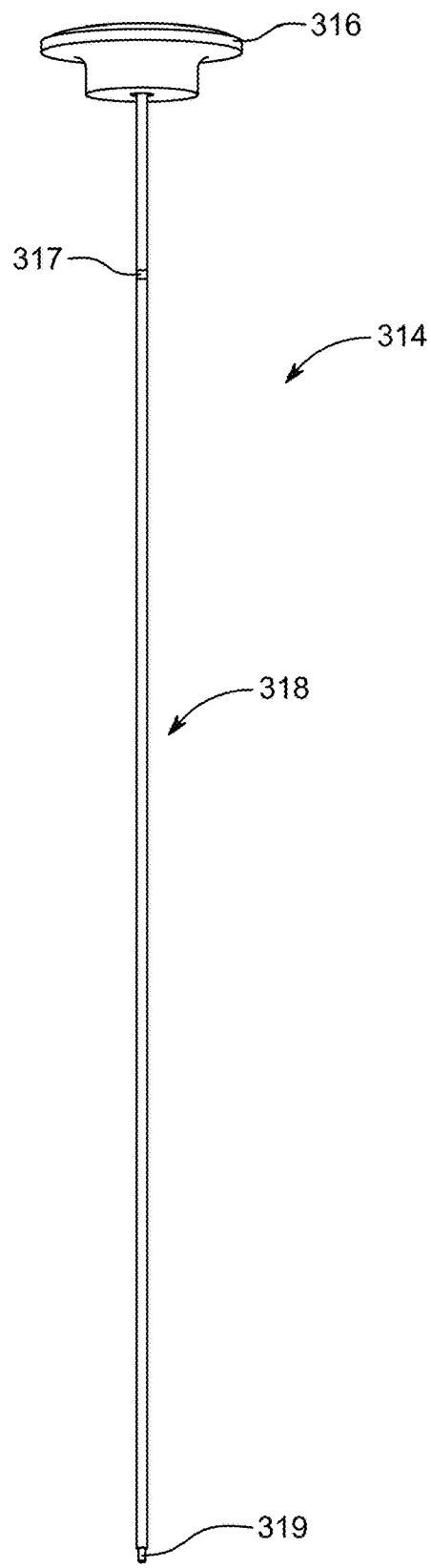
Figure 3W:
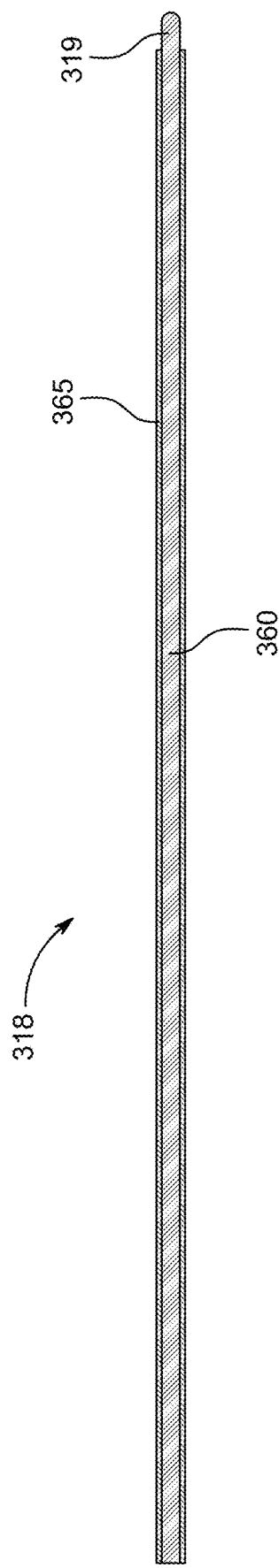
Figure 3B:
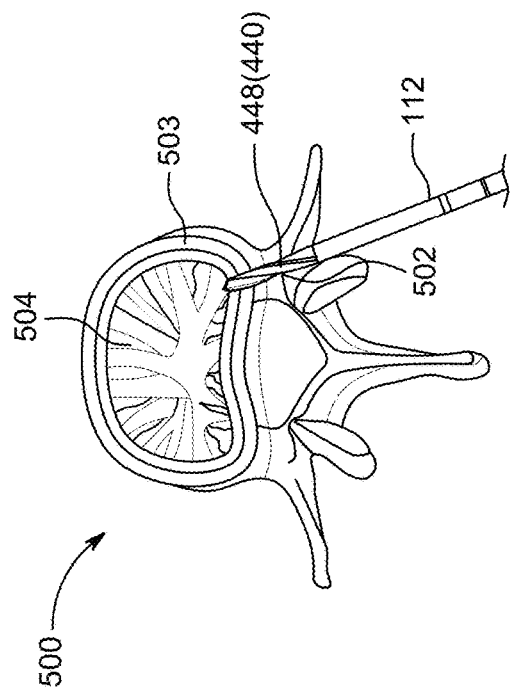
Figure 3D:
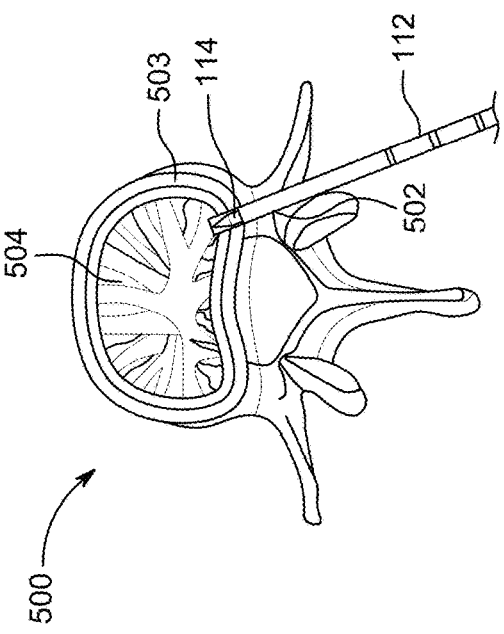
Figure 3A:
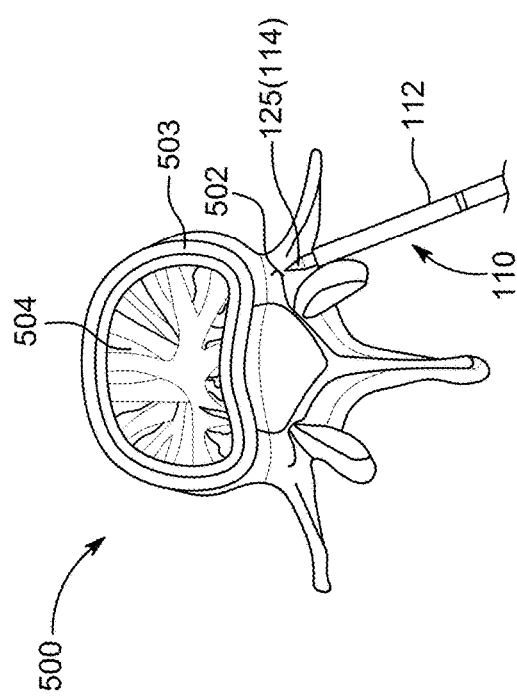
Figure 3C:
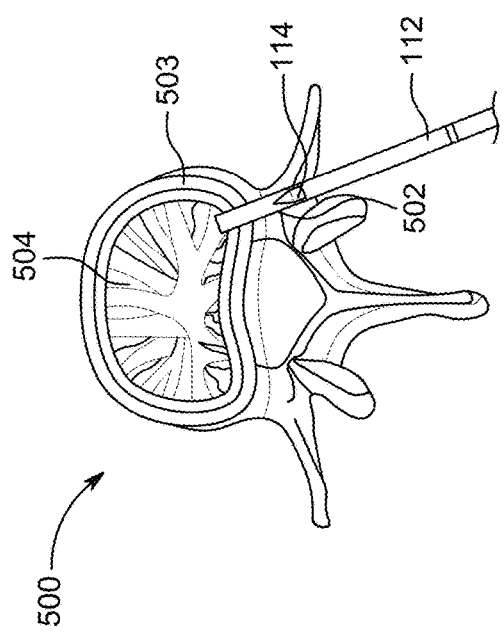
Figure 3F:
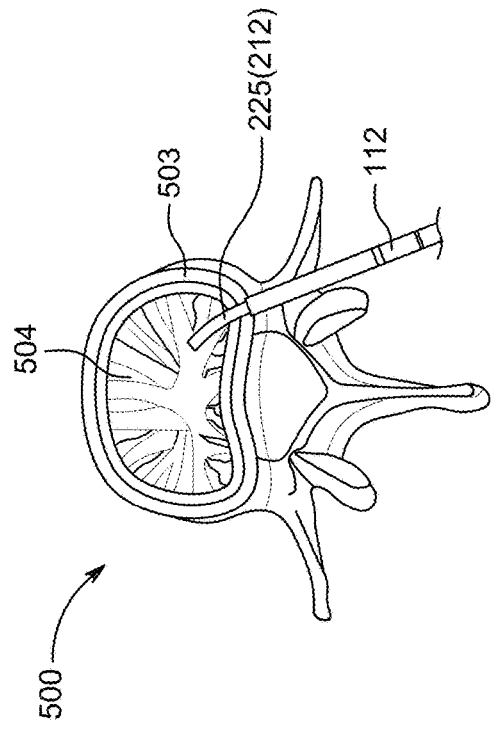
Figure 3H:
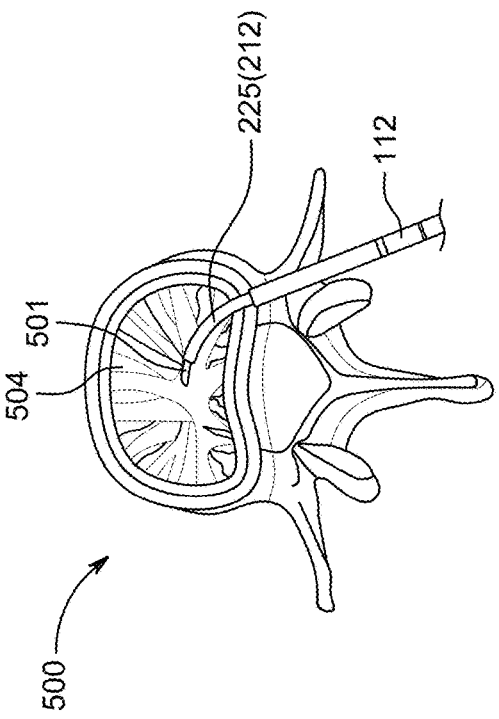
Figure 3E:
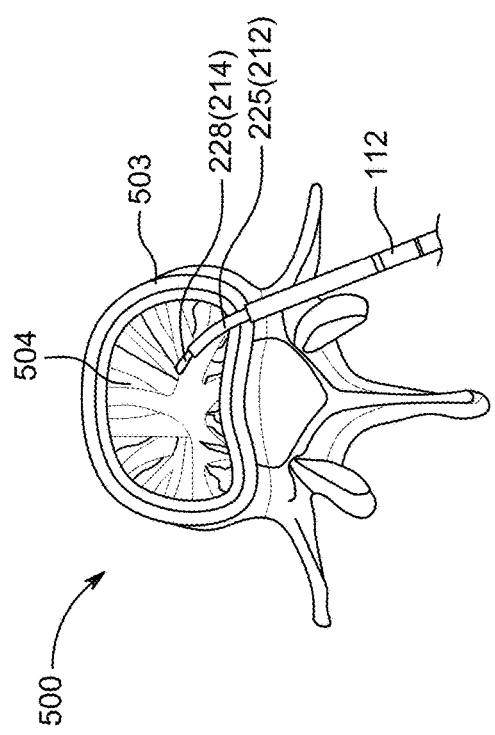
Figure 3G:
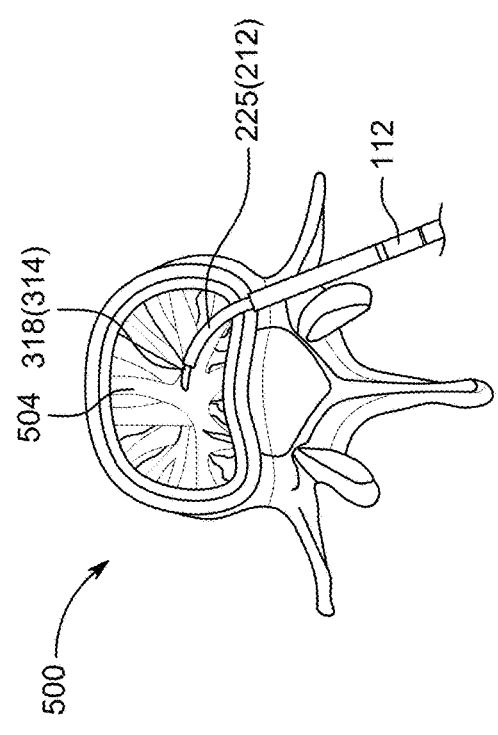

FIGS. 3F-3H illustrate the introducer assembly 110 after the introducer stylet 114 has been inserted within the introducer cannula 112. As indicated above, the proximal handle 116 of the introducer cannula 112 may include mating or engagement features (e.g., coupling features 121) that facilitate automatic (e.g., snap-fit) engagement of the introducer stylet 114 with the proximal handle 116 of the introducer cannula 112.

The proximal handle 126 of the introducer stylet 114 includes an alignment indicator 129, an anti-rotation tab 131, and a press button 134. As shown best in FIG. 3G, the alignment indicator 129 is configured to align with a corresponding alignment indicator 130 on the upper surface of the crossbar portion 115 of the proximal handle 116 of the introducer cannula 112 in order to ensure proper insertion and alignment of the introducer stylet 114 with respect to the introducer cannula 112. The anti-rotation tab 131 is configured to be positioned within the slot 117 of the proximal handle 116 of the introducer cannula 112 and to prevent rotation of the introducer stylet 114 with respect to the introducer cannula 112 during malleting and orienting.

The press button 134 is integrally coupled to the anti-rotation tab 131 such that pressing of the press button 134 extends the anti-rotation tab 131 out of the constraint of the slot 117, thereby allowing the introducer stylet 114 to rotate with respect to the introducer cannula 112 (as shown in FIG.

3H). Pressing the press button 134 also releases engagement of the introducer stylet 114 with the introducer cannula 112 to enable removal of the introducer stylet 114 from the introducer cannula 112. The proximal handle 126 of the introducer stylet 114 may include internal ramps (not shown) configured to provide a mechanical advantage to assist in removal of the introducer stylet 114 from the introducer cannula 112 (especially if bone shards have packed into gaps between the introducer stylet 114 and introducer cannula 112 making removal more difficult) as the proximal handle 126 is rotated (e.g., 120-degree rotation counter-clockwise). The combination of the scalloped distal end portion design and the internal ramps in the proximal handle 126 may provide increased reduction of removal forces by 50%-70% compared to a full diameter (e.g., no scalloped section) distal end portion design with no ramps in the proximal handle 126.

FIGS. 3I and 3J illustrate a side view and a top view of an embodiment of the curved cannula 212. The curved cannula 212 includes a proximal handle 216, a threaded proximal shaft portion 220, a gear wheel 221, a rigid support portion 223, and a distal polymeric shaft portion 224. The proximal handle 216 includes a curved slot 217 and a curved ramp 231 configured to facilitate insertion of the J-stylet 214 into and along a central lumen of the curved cannula 212 extending from the proximal handle 216 to an open distal tip 222 of the distal polymeric shaft portion 224. The central lumen of the curved cannula 212 may be coated with a medical grade silicone lubricant to improve tool insertion and removal.

In the illustrated example, the gear wheel 221 comprises threads configured to interface with corresponding threads of the threaded proximal shaft portion 220 such that rotation of the gear wheel 221 causes controlled proximal and distal translation of the gear wheel 221 along the threaded proximal shaft portion 220. The threaded proximal shaft portion 220 is sized such that when the gear wheel 221 is in its distal-most position, the distal tip 222 of the curved cannula 212 does not extend out of the open distal tip 122 of the introducer cannula 112 when the curved cannula assembly 210 is fully inserted therein. The gear wheel 221 may spin freely about the threaded proximal shaft portion 220. The threads may comprise triple threads and the gear wheel 221 may be configured to traverse the entire length of the threaded proximal shaft portion 220 with four complete rotations of the gear wheel 221.

The rigid support portion 223 may comprise a biocompatible metal or other rigid material, such as stainless steel, titanium, platinum and/or the like, so as to provide additional support to the curved cannula 212 during insertion of the J-stylet 214. The distal polymeric shaft portion 224 may be comprised of a thermoplastic, shape-memory polymer material (such as polyether ether ketone (PEEK), polyurethane, polyethylene terephthalate (PET), and/or the like) and the distal end portion 225 is pre-curved (e.g., shape-set) to have a predetermined curve in a "resting" unconstrained configuration.

FIGS. 3K-3P illustrate an embodiment of the J-stylet 214. FIG. 3K illustrates a side view of the J-stylet 214 in a "resting" normal, unconstrained configuration or state and FIGS. 3L and 3M are close-up views (side view and perspective view, respectively) of a curved distal end portion 227 of the J-stylet 214. The J-stylet 214 comprises a proximal handle 226 and a distal elongate shaft 218. The proximal handle 226 comprises an upper surface that is adapted for malleting by a mallet and a lower surface that is adapted to facilitate removal of the J-stylet 214 by two or more (e.g., two, three, or four) fingers of an operator. The upper surface of the proximal handle 216 includes an alignment indicator 219 (shown, for example, in FIG. 3P) configured to be aligned with the corresponding alignment indicator 130 of the introducer cannula 112 to facilitate insertion, removal, and deployment of the J-stylet 214 (and curved cannula assembly 210).

The distal elongate shaft 218 includes a curved distal end portion 227 having an asymmetric curve profile along its length (e.g., the curved distal end portion does not have a constant full diameter along its length). A distal channeling tip 228 is sized and shaped to facilitate channeling through cancellous bone along a curved path or trajectory. The curved distal end portion 227 comprises a springboard or platform section 229 having a "D-shaped" cross-sectional profile, as shown, for example, by the cross-section profile circle in FIG. 3M. The springboard or platform section 229 may be formed by mechanical grinding of a tubular wire until the desired D-shaped cross section profile is achieved in which a top (e.g., upper) surface of the springboard or platform section 229 is generally smooth and flat. The thickness (e.g., vertical cross-sectional dimension) of the springboard or platform section 229, the predefined set angulation or radius of curvature, and the starting and ending points of the springboard or platform section 229 along the length of the curved distal end portion 227 may be varied to provide J-stylets having different rigidity and bending characteristics for different levels of vertebrae or different densities of bone.

In accordance with several embodiments, a thickness (e.g., a maximum vertical cross-sectional dimension from an upper surface of the springboard or platform section 229 to a lower-most point on a lower surface of the curved distal end portion) is between 40% and 85% (e.g., between 40% and 60%, between 50% and 70%, between 50% and 75%, between 60% and 70%, between 65% and 80%, between 70% and 85%, overlapping ranges thereof, or any value within the recited ranges) of the thickness (e.g., diameter) of the adjacent regions of the curved distal end portion (e.g., the regions just proximal and just distal of the length of the springboard or platform section 229). Instead of percentages, the difference in thickness dimensions could be represented as ratios (e.g., between 2:5 and 4:5, between 2:5 and 3:5, between 1:2 and 3:4, between 3:5 and 4:5, between 3:5 and 6:7). The ending point of the springboard or platform section 229 may be between 4.5 and 9 mm from a distal terminus of the distal elongate shaft 218. The starting point of the springboard or platform section 229 may be between 230 mm and 245 mm from a proximal terminus of the distal elongate shaft 218.

According to several embodiments, the asymmetric curve profile (e.g., profile with D-shaped cross-section) advantageously provides improved cephalad-caudal steering because the curved distal end portion 227 primarily bends inward and not laterally. In addition, the design and material of the curved distal end portion 227 of the J-stylet 214 may enable the angle of curvature of the curved distal end portion 227 to advantageously remain relatively consistent and reproducible across a variety of bone densities, or regardless of bone environment. For example, in one embodiment, the design and material of the curved distal end portion 227 of the J-stylet 214 facilitates consistent and reproducible access to a posterior location (e.g., in posterior half of the vertebral body or to a location approximately 30%-50% of the distance between the posterior-most aspect and the anterior-most aspect of the vertebral body along a sagittal axis or to a geometric center or midpoint within the vertebral body for vertebral bodies having varying bone densities or other desired target location in the vertebral body or other bone). In accordance with several embodiments, the curvature is designed to deviate by less than 25 degrees (e.g., less than 20 degrees, less than 15 degrees, less than 10 degrees) or less than 30% from the predefined set curvature of the curved distal end portion 227 in an unconstrained configuration (even in hard bone).

The J-stylet 214 may be designed and adapted to exert a lateral force of between 6 pounds and 8 pounds. The angle of curvature of the curved distal end portion 227 (with respect to the central longitudinal axis of the straight proximal portion of the distal elongate shaft 218) of the J-stylet 214 in the normal unconstrained state or configuration may be designed to be between 65 degrees and 80 degrees (e.g., 65 degrees, 70 degrees, 75 degrees, 80 degrees, or any other value within the recited range). The radius of curvature of the curved distal end portion 227 may range from 11.5 mm to 15 mm (e.g., from 11.5 mm to 12 mm, from 12 mm to 12.5 mm, from 12 mm to 13 mm, from 12.5 mm to 14 mm, from 13 mm to 15 mm, overlapping ranges thereof, or any value within the recited ranges). The J-stylet 214 may be comprised of nitinol or other metallic alloy material.

FIGS. 3N and 3O are a perspective view and a side cross-section view, respectively, illustrating insertion of the curved distal end portion 227 of the J-stylet 214 into the slot 217 of the proximal handle 216 of the curved cannula 212. As shown in FIG. 3O, the slot 217 comprises a curved ramp 231 and a straight vertical backstop support 233 (e.g., with no trumpeted section) to facilitate insertion of the curved distal end portion 227 of the J-stylet 214. As indicated above, the curved cannula 212 includes the rigid support portion 223 extending into and out of the threaded shaft portion 220 to provide additional support upon insertion of the J-stylet 214 within the central lumen of the curved cannula 212.

FIGS. 3P and 3Q illustrate insertion of the curved cannula assembly 210 into the introducer cannula 112. The curved distal end portion 225 of the curved cannula assembly 210 is inserted from a side angle (e.g., at about a 65 to 75 degree angle (such as a 70 degree starting angle in one embodiment) with respect to the central longitudinal axis LA of the distal hypotube 118 of the introducer cannula 112) into the slot 117 and along the ramp 141 in the proximal handle 116 and then down the central lumen of the distal hypotube 118 of the introducer cannula 112 while the gear wheel 221 of the curved cannula 212 is in a distal-most position along the threaded proximal portion 220 of the curved cannula 212 so as to prevent inadvertent advancement of the curved distal portion of the curved cannula assembly 210 beyond the open distal tip 122 of the introducer cannula 112 until the operator is ready to do so.

FIG. 3Q is a close-up side cross-section view of the proximal portion of the introducer cannula 112 and the curved distal portion of the curved cannula assembly 210 and illustrates insertion of the curved distal end portions of the assembled components of the curved cannula assembly 210 into the introducer cannula 112. As shown, the introducer cannula 112 is shaped so as to provide a backstop support 143 generally aligned with the inner surface of the central lumen of the hypotube 118 so as to facilitate insertion and so that the curved distal end portion 225 of the distal polymeric shaft portion 224 of the curved cannula 212 does not pivot out of the introducer cannula 112 upon insertion. In accordance with several embodiments, the asymmetric "D-shaped" cross-sectional profile of the J-stylet 214 is advantageously designed to prevent twisting during insertion.

FIGS. 3R and 3S illustrate operation of the gear wheel 221 of the curved cannula 212. As shown in FIG. 3R, the gear wheel 221 is rotated until it is in its distal-most position along the threaded proximal portion 220 prior to insertion of the curved cannula assembly 210 within the introducer cannula 112 so as to prevent inadvertent advancement of the curved distal end portions 225, 227 of the curved cannula assembly 210 out of the introducer cannula 112. As shown in FIG. 3S, the gear wheel 221 is rotated to its proximal-most position along the threaded proximal portion 220 to enable full insertion of the curved cannula assembly 210 within the introducer cannula 112 such that the curved distal end portions 225, 227 of the curved cannula assembly 210 extend out of the introducer cannula 112 and along a curved path within the cancellous bone region of the vertebral body or other bone.

FIGS. 3T and 3U illustrate operation of a bail mechanism of the J-stylet 214. The proximal handle 226 of the J-stylet 214 includes a bail actuator 250 configured to be toggled between a first "resting" or "inactive" configuration in which the bail actuator 250 is generally aligned with (e.g., parallel or substantially parallel to) the upper surface of the proximal handle 226 (as shown in FIG. 3T) and a second "active" configuration in which the bail actuator 250 is offset from the upper surface of the proximal handle 226 (as shown in FIG. 3U). The bail actuator 250 is configured to act as a lever to cause a slight axial (proximal-distal) movement of the J-stylet 214 with respect to the curved cannula 212 as the bail actuator 250 is pivoted. When the bail actuator 250 is toggled to the "active" configuration, a flange 253 of the bail actuator 250 contacts the proximal handle 216 of the curved cannula to cause proximal retraction of the J-stylet 214 with respect to the curved cannula 212 such that the distal channeling tip 228 of the J-stylet 214 resides completely within the curved cannula 212 and does not extend out of the open distal tip of the curved cannula 212. In accordance with several embodiments, the bail actuator 250 is advantageously toggled to the "active" configuration (in which the distal channeling tip 228 of the J-stylet 214 resides within the open distal tip of the curved cannulas 212) upon insertion and removal of the curved cannula assembly 210 from the introducer cannula 112 or the J-stylet 214 from the curved cannula 212 (e.g., so as to avoid friction caused by interaction between two metal components). The upper surface of the bail actuator 250 may include an indicator 252 (e.g., colored marking or other visual indicator) that is visible to an operator when the bail actuator 250 is in the active configuration and hidden when the bail actuator 250 is in the inactive configuration.

FIG. 3V illustrates a side view of an embodiment of the straight stylet 314 and FIG. 3W illustrates a distal portion of the straight stylet 314. The straight stylet 314 includes a proximal handle 316 and a distal elongate shaft 318. The proximal handle 316 includes an upper surface adapted for malleting by a mallet or application of pressure by a hand or fingers of an operator. A radiopaque marker band 317 may be positioned along the distal elongate shaft 318 at a position corresponding to the position when a distal channeling tip 319 of the straight stylet 314 is exiting the open distal tip of the curved cannula 212 as the straight stylet 314 is advanced through the curved cannula 212. The length of the straight stylet 314 may be sized such that, when the straight stylet 314 is fully inserted within the curved cannula 212, the length of the portion of the straight stylet 314 extending beyond the open distal tip of the curved cannula 212 is between 25 and 50 mm (e.g., between 25 mm and 35 mm, between 30 mm and 40 mm, between 35 mm and 45 mm, between 40 and 50 mm, overlapping ranges thereof, or any value within the recited ranges). The diameter of the straight stylet 314 is sized so as to be inserted within and through the central lumen of the curved cannula 212.

The distal elongate shaft 318 comprises an inner flexible, shape memory core 360 extending from the proximal handle 316 to the distal channeling tip 319 of the straight stylet 314 and a polymeric outer layer 365 extending from the proximal handle 316 to a distal end of the distal elongate shaft 318 but stopping short (or proximal to) the distal channeling tip 319 so that the inner core 360 protrudes out of the outer layer 365. The straight stylet 314 is flexible enough to bend to traverse the curved distal end portion 225 of the curved cannula 212 without significant friction but sufficiently rigid so as to maintain a straight path once the straight stylet 314 exits the open distal tip of the curved cannula 212. The inner core 360 of the straight stylet 314 may comprise nitinol or other metallic alloy or other flexible material. The outer layer 365 may be comprised of a more rigid, polymeric material (such as PEEK, polyurethane, PET, and/or the like).

FIGS. 3X-3Z illustrate an embodiment of an introducer drill 440 and its interaction with the introducer cannula 112. A kit or system of access instruments (e.g., a kit or kit module designed for accessing hard, or high-density, bone) may optionally include the introducer drill 440. FIG. 3X is a side view of an embodiment of the introducer drill 440. The introducer drill 440 includes a proximal handle 446 and an elongate drill shaft 447. The proximal handle 446 may comprise a generally T-shaped design and may comprise a soft-grip overmolding. The length of the elongate drill shaft 447 may be sized so as to extend from 20 mm to 35 mm beyond the open distal tip of the introducer cannula 112 when the introducer drill 440 is fully inserted within the introducer cannula 112. The elongate drill shaft 447 may include a solid proximal portion 448 and a fluted distal portion 449.

FIG. 3Y is a close-up perspective view of the fluted distal portion 449. The fluted distal portion 449 may comprise a distal cutting tip 450 having a 90 degree cutting angle. The drill flutes 452 of the fluted distal portion 449 may be adapted to taper away from the distal cutting tip 450 (which is a reverse taper or opposite the direction of taper of a typical drill bit) so as to facilitate improved bone chip packing within the open flute volume as bone chips and fragments are generated by operation of the introducer drill 440. The distal cutting tip 450 may have a point angle of between 65 and 75 degrees and a chisel edge angle of between 115 and 125 degrees. The flutes may advantageously be deeper and wider than typical drill bits because the elongate drill shaft 447 is supported by a rigid introducer cannula 112 surrounding at least a portion of the length of the elongate drill shaft (and a portion of the length of the fluted distal portion in most instances) during use. The drill flutes 452 may have a helix angle of between 12 degrees and 18 degrees (e.g., between 12 degrees and 14 degrees, between 13 degrees and 17 degrees, between 14 degrees and 16 degrees, between 14 degrees and 18 degrees, overlapping ranges thereof, or any value within the recited ranges). The fluted distal portion 449 may include two flutes having a length of between 70 mm and 85 mm.

The open flute volume of the fluted distal portion 449 may be advantageously configured to hold all or substantially all (e.g., more than 75%, more than 80%, more than 85%, more than 90%) of the significantly-sized bone chips or fragments removed by the introducer drill 440 as the introducer drill 440 is removed from the introducer cannula 112, thereby reducing the bone fragments left behind in the bone (e.g., vertebral body) or in the introducer cannula 112. In some embodiments, the open flute volume of the fluted distal portion 449 is adapted to hold about 2 ccs of bone. The fluted distal portion 449 may exhibit web tapering (e.g., increase in width or depth, or angle with respect to longitudinal axis of the flutes) along its length from distal to proximal (e.g., reverse taper). There may be no web taper for approximately the first 25 mm at the distal-most region. The web taper may then increase gradually until a maximum web taper is reached near the proximal end of the fluted distal portion 449 so as to facilitate pushing of the bone fragments or chip upward (or proximally) along the fluted distal portion 449. For example, the fluted distal portion 449 may have a negative draft (e.g., 0.77" or ~20 mm negative draft).

FIG. 3Z illustrates the introducer drill 440 fully inserted and engaged with the proximal handle 116 of the introducer cannula 112. The introducer drill 440 is sized so as to be inserted within the central opening 120 of the proximal handle 116 of the introducer cannula 112 and advanced through the central lumen of the hypotube 118 of the introducer cannula 112. The proximal handle 446 of the introducer drill 440 is configured to engage with the coupling or mating features 121 of the proximal handle 116.

FIGS. 3AA-3HH illustrate an embodiment of steps of a method of using the access tools to facilitate access to a location within a vertebral body 500 for treatment (e.g., modulation of intraosseous nerves, such as a basivertebral nerve, bone cement delivery for treatment of vertebral fractures, and/or ablation of bone tumors). With reference to FIG. 3AA, the distal portion of the introducer assembly 110 (including the distal tip 125 of the introducer stylet 114 and the distal tip of the introducer cannula 112) are inserted through a pedicle 502 adjacent the vertebral body 500 by malleting on the proximal handle of the introducer stylet 114 after insertion and aligned engagement of the introducer stylet 114 within the introducer cannula 112.

In accordance with several embodiments, the method may optionally include removing the introducer stylet after initial penetration into the pedicle 502 (for example, if the operator can tell that the density of the bone is going to be sufficiently dense or hard that additional steps and/or tools will be needed to obtain a desired curved trajectory to access a posterior portion (e.g., posterior half) of the vertebral body 500. With reference to FIG. 3BB, the method may optionally include inserting the introducer drill 440 into and through the introducer cannula 112 to complete the traversal of the pedicle 502 and penetration through a cortical bone 503 region of the vertebral body 500 until a cancellous bone region 504 of the vertebral body 500 is reached. The introducer drill 550 may be advanced into the cancellous bone region 504 (especially if the cancellous bone region 504 is determined to be sufficiently hard or dense) or the advancement may stop at the border between the cortical bone region 503 and the cancellous bone region 504. This step may involve both rotating the introducer drill 440 and malleting on the proximal handle 446 of the introducer drill 440 or simply rotating the introducer drill 440 without malleting on the proximal handle 446. With reference to FIG. 3CC, the introducer drill 440 may be removed and the introducer stylet 114 may be re-inserted within the introducer cannula 112. With reference to FIG. 3DD, the introducer assembly 110 may then be malleted so as to advance the distal tip 122 of the introducer cannula 112 to the entry site into (or within) the cancellous bone region 504 of the vertebral body 500. The introducer stylet 114 may then be removed from the introducer cannula 112.

The curved cannula assembly 210 may then be inserted within the introducer cannula 112 with the gear wheel 221 in the distal-most position so as to prevent inadvertent advancement of the curved cannula assembly 210 out of the open distal tip 122 of the introducer cannula 112 prematurely. With reference to FIG. 3EE, after rotation of the gear wheel 221 to a more proximal position, the curved cannula assembly 210 can be malleted so as to advance the collective curved distal end portions of the curved cannula assembly 210 together out of the distal tip 122 of the introducer cannula 112 and along a curved path within the cancellous bone region 504. With reference to FIG. 3FF, the J-stylet 214 may then be removed from the curved cannula 212, with the curved cannula 212 remaining in position. In accordance with several embodiments, the path formed by the prior instruments may advantageously allow the curved cannula assembly 210 to have a head start and begin curving immediately upon exiting the open distal tip 122 of the introducer cannula 112.

With reference to FIG. 3GG, if a further straight path beyond the curved path is desired to reach a target treatment location, the straight stylet 314 may be inserted through the curved cannula 212 such that the distal channeling tip 319 of the straight stylet extends beyond the open distal tip of the curved cannula 212 and along a straight path toward the target treatment location (e.g., a basivertebral nerve trunk or basivertebral foramen). In some embodiments, the straight stylet 314 may not be needed and this step may be skipped.

With reference to FIG. 3HH, a treatment device 501 (e.g., a flexible bipolar radiofrequency probe) may be inserted through the curved cannula 212 (after removal of the straight stylet 314 if used) and advanced out of the open distal tip of the curved cannula 212 to the target treatment location. The treatment device 501 may then perform the desired treatment. For example, if the treatment device 501 is a radiofrequency probe, the treatment device 501 may be activated to ablate intraosseous nerves (e.g., a basivertebral nerve) or a tumor within the vertebral body 500. Bone cement or other agent, or a diagnostic device (such as a nerve stimulation device or an imaging device to confirm ablation of a nerve) may optionally be delivered through the curved cannula 212 after the treatment device 501 is removed from the curved cannula 212.

At certain levels of the spine (e.g., sacral and lumbar levels) and for certain patient spinal anatomies that require a steeper curve to access a desired target treatment location within the vertebral body, a combination curette/curved introducer may first be inserted to start a curved trajectory (e.g., create an initial curve or shelf) into the vertebra. The curette may have a pre-curved distal end portion or be configured such that the distal end portion can be controllably articulated or curved (e.g., manually by a pull wire or rotation of a handle member coupled to one or more pull wires coupled to the distal end portion or automatically by a robotic or artificial intelligence driven navigation system). The combination curette/curved introducer may then be removed and the outer straight cannula and inner curved cannula/curved stylet assembly may then be inserted to continue the curve toward the target treatment location.

In accordance with several implementations, any of the access tools (e.g., cannula or stylet) or treatment devices may comprise a rheological and/or magnetizable material (e.g., magnetorheological fluid) along a distal end portion of the access tool that is configured to be curved in situ after insertion to a desired location within bone (e.g., vertebra). A magnetic field may be applied to the distal end portion of the access tool and/or treatment device with the magnetizable fluid or other material and adjusted or varied using one or more permanent magnets or electromagnets to cause the distal end portion of the access tool and/or treatment device to curve toward the magnetic field. In some implementations, a treatment probe may include a magnetic wire along a portion of its length (e.g., a distal end portion). Voltage applied to the magnetic wire may be increased or decreased to increase or decrease a curve of the magnetic wire. These implementations may advantageously facilitate controlled steering without manual pull wires or other mechanical mechanisms. The voltage may be applied by instruments controlled and manipulated by an automated robotic control system, such as the robotic system described in connection with FIG. 7.

The treatment devices (e.g., treatment probes) may be any device capable of modulating tissue (e.g., nerves, tumors, bone tissue). Any energy delivery device capable of delivering energy can be used (e.g., RF energy delivery devices, microwave energy delivery devices, laser devices, infrared energy devices, other electromagnetic energy delivery devices, ultrasound energy delivery devices, and the like). The treatment device 501 may be an RF energy delivery device. The RF energy delivery device may include a bipolar pair of electrodes at a distal end portion of the device. The bipolar pair of electrodes may include an active tip electrode and a return ring electrode spaced apart from the active tip electrode. The RF energy delivery device may include one or more temperature sensors (e.g., thermocouples, thermistors) positioned on an external surface of, or embedded within, a shaft of the energy delivery device. The RF energy delivery device may not employ internally circulating cooling, in accordance with several implementations.

In some implementations, water jet cutting devices may be used to modulate (e.g., denervate) nerves. For example, a water jet cutter may be configured to generate a very fine cutting stream formed by a very high-pressure jet of water. For example, the pressure may be in the range of 15 MPa to 500 MPa (e.g., 15 MPa to 50 MPa, 30 MPa-60 MPa, 50 MPa-100 MPa, 60 MPa-120 MPa, 100 MPa-200 MPa, 150 MPa-300 MPa, 300 MPa-500 MPa, overlapping ranges thereof, or any value within the recited ranges). In some implementations, a chemical neuromodulation tool injected into a vertebral body or at an endplate may be used to ablate or otherwise modulate nerves or other tissue. For example, the chemical neuromodulation tool may be configured to selectively bind to a nerve or endplate. In some implementations, a local anesthetic (e.g., liposomal local anesthetic) may be used inside or outside a vertebral body or other bone to denervate or block nerves. In some implementations, brachytherapy may be used to place radioactive material or implants within the vertebral body to deliver radiation therapy sufficient to ablate or otherwise denervate the vertebral body. In some implementations, chymopapain injections and/or condoliase injections may be used (e.g., under local anesthesia). Phototherapy may be used to ablate or otherwise modulate nerves after a chemical or targeting agent is bound to specific nerves or to a vertebral endplate.

In accordance with several implementations, thermal energy may be applied within a cancellous bone portion (e.g., by one or more radiofrequency (RF) energy delivery instruments coupled to one or more RF generators) of a vertebral body. The thermal energy may be conducted by heat transfer to the surrounding cancellous bone, thereby heating up the cancellous bone portion. In accordance with several implementations, the thermal energy is applied within a specific frequency range and having a sufficient temperature and over a sufficient duration of time to heat the cancellous bone such that the basivertebral nerve extending through the cancellous bone of the vertebral body is modulated. In several implementations, modulation comprises permanent ablation or denervation or cellular poration (e.g., electroporation). In some implementations, modulation comprises temporary denervation or inhibition. In some implementations, modulation comprises stimulation or denervation without necrosis of tissue.

For thermal energy, temperatures of the thermal energy may range from about 70 to about 115 degrees Celsius (e.g., from about 70 to about 90 degrees Celsius, from about 75 to about 90 degrees Celsius, from about 83 to about 87 degrees Celsius, from about 80 to about 100 degrees Celsius, from about 85 to about 95 degrees Celsius, from about 90 to about 110 degrees Celsius, from about 95 to about 115 degrees Celsius, or overlapping ranges thereof). The temperature ramp may range from 0.1-5 degrees Celsius/second (e.g., 0.1-1.0 degrees Celsius/second, 0.25 to 2.5 degrees Celsius/second, 0.5-2.0 degrees Celsius/second, 1.0-3.0 degrees Celsius/second, 1.5-4.0 degree Celsius/second, 2.0-5.0 degrees Celsius/second). The time of treatment may range from about 10 seconds to about 1 hour (e.g., from 10 seconds to 1 minute, 1 minute to 5 minutes, from 5 minutes to 10 minutes, from 5 minutes to 20 minutes, from 8 minutes to 15 minutes, from 10 minutes to 20 minutes, from 15 minutes to 30 minutes, from 20 minutes to 40 minutes, from 30 minutes to 1 hour, from 45 minutes to 1 hour, or overlapping ranges thereof). Pulsed energy may be delivered as an alternative to or in sequence with continuous energy. For radiofrequency energy, the energy applied may range from 350 kHz to 650 kHz (e.g., from 400 kHz to 600 kHz, from 350 kHz to 500 kHz, from 450 kHz to 550 kHz, from 500 kHz to 650 kHz, overlapping ranges thereof, or any value within the recited ranges, such as 450 kHz±5 kHz, 475 kHz±5 kHz, 487 kHz±5 kHz). A power of the radiofrequency energy may range from 5 W to 30 W (e.g., from 5 W to 15 W, from 5 W to 20 W, from 8 W to 12 W, from 10 W to 25 W, from 15 W to 25 W, from 20 W to 30 W, from 8 W to 24 W, and overlapping ranges thereof, or any value within the recited ranges). In accordance with several implementations, a thermal treatment dose (e.g., using a cumulative equivalent minutes (CEM) 43 degrees Celsius thermal dose calculation metric model) is between 200 and 300 CEM (e.g., between 200 and 240 CEM, between 230 CEM and 260 CEM, between 240 CEM and 280 CEM, between 235 CEM and 245 CEM, between 260 CEM and 300 CEM) or greater than a predetermined threshold (e.g., greater than 240 CEM). The CEM number may represent an average thermal cumulative dose value at a target treatment region or location and may represent a number that expresses a desired dose for a specific biological end point. Thermal damage may occur through necrosis or apoptosis.

Cooling may optionally be provided to prevent surrounding tissues from being heated during the nerve modulation procedure. The cooling fluid may be internally circulated through the delivery device from and to a fluid reservoir in a closed circuit manner (e.g., using an inflow lumen and an outflow lumen). The cooling fluid may comprise pure water or a saline solution having a temperature sufficient to cool electrodes (e.g., 2-10 degrees Celsius, 5-10 degrees Celsius, 5-15 degrees Celsius). Cooling may be provided by the same instrument used to deliver thermal energy (e.g., heat) or a separate instrument. In accordance with several implementations, cooling is not used.

In some implementations, ablative cooling may be applied to the nerves or bone tissue instead of heat (e.g., for cryoneurolysis or cryoablation applications). The temperature and duration of the cooling may be sufficient to modulate intraosseous nerves (e.g., ablation, or localized freezing, due to excessive cooling). The cold temperatures may destroy the myelin coating or sheath surrounding the nerves. The cold temperatures may also advantageously reduce the sensation of pain. The cooling may be delivered using a hollow needle under fluoroscopy or other imaging modality.

In some implementations, one or more fluids or agents may be delivered to a target treatment site to modulate a nerve. The agents may comprise bone morphogenetic proteins, for example. In some implementations, the fluids or agents may comprise chemicals for modulating nerves (e.g., chemoablative agents, alcohols, phenols, nerve-inhibiting agents, or nerve stimulating agents). The fluids or agents may be delivered using a hollow needle or injection device under fluoroscopy or other imaging modality.

One or more treatment devices (e.g., probes) may be used simultaneously or sequentially. For example, the distal end portions of two treatment devices may be inserted to different locations within a vertebral body or other bone or within different vertebral bodies or bones. Radiofrequency treatment probes may include multiple electrodes configured to act as monopolar, or unipolar, electrodes or as pairs of bipolar electrodes. The treatment device(s) may also be pre-curved or curveable such that the curved stylet is not needed or may have sharp distal tips such that additional sharpened stylets are not needed. In some implementations, any or all of the access tools and the treatment devices are MR-compatible so as to be visualized under MR imaging.

The one or more treatment devices (e.g., probes such as radiofrequency probes, treatment device 501 of a kit or system) may include an indicator configured to alert a clinician as to a current operation state of the treatment device. For example, the indicator may include a light ring disposed along a length of, and extending around a circumference of, the treatment device. The light ring may be configured to light up with different colors and/or exhibit other visible effects (e.g., pulsing on and off with certain patterns). The one or more treatment devices may also be configured to provide audible alerts (e.g., beeps having a certain frequency or intonation) corresponding to different operational states. In one implementation, the light ring may be dark or not lit up when the treatment device is not connected to a radiofrequency generator or not ready for RF energy delivery. The light ring may pulse at a first rate (e.g., 1 pulse every 2-3 seconds) to indicate an operational state in which the treatment device and generator system are ready to initiate RF energy delivery. The light ring may be continuously lit up to indicate an operational state in which the treatment device is actively delivering RF energy. The light ring may pulse at a second rate different than (e.g., faster than, slower than) the first rate to indicate an operational state in which an error has been detected by the generator or if a particular treatment parameter is determined to be outside an acceptable range of values. In one implementation, the second rate is greater than the first rate (e.g., 2 pulses per second). Haptic feedback may also be provided to the clinician for at least some of the operational states to provide a further alert in addition to a visible alert.

In some implementations, the treatment device (e.g., treatment device 501) includes a microchip that is preprogrammed with treatment parameters (e.g., duration of treatment, target temperature, temperature ramp rate). Upon electrical connection of the treatment device to the generator, the treatment parameters are transmitted to the generator and displayed on a display of the generator to provide confirmation of desired treatment to a clinician.

Figure 4:
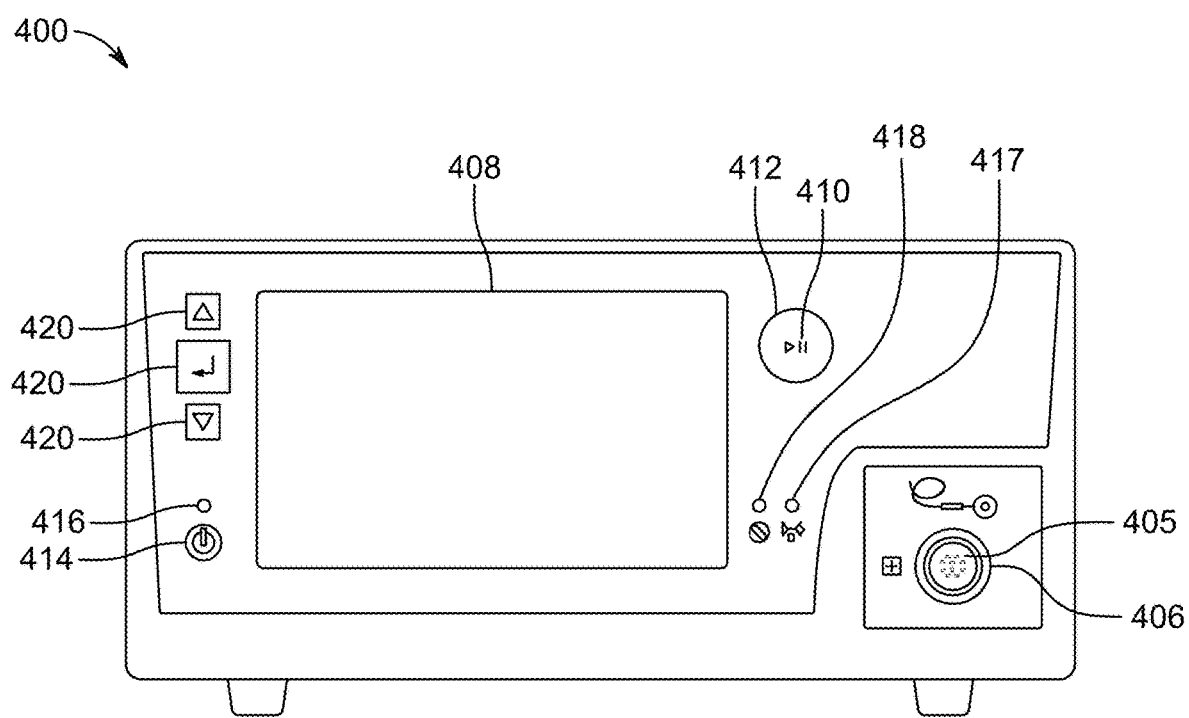
FIG. 4 illustrates an example radiofrequency generator.

FIG. 4 illustrates a front view of an embodiment of a generator 400 (e.g., radiofrequency energy generator). The generator 400 includes an instrument connection port 405 to which a treatment device (e.g., RF energy delivery probe) may be connected. The generator 400 may be configured for use without a neutral electrode (e.g., grounding pad). The instrument connection port 605 is surrounded by an indicator light 406 configured to illuminate when the treatment device is properly connected to the instrument connection port 405. As shown, the indicator light 406 may comprise a circular LED indicator light. The indicator light 406 may be configured to continuously illuminate in a solid color (e.g., white, blue, green) when a treatment device is connected to the instrument connection port 405. The indicator light 406 may flash at a first pulsing rate (e.g., 1 Hz) to prompt a clinician to connect the treatment device to the instrument connection port 405. The indicator light 406 may flash at a second pulsing rate different than (e.g., faster than) the first pulsing rate (e.g., 2 Hz, 3 Hz, 4 Hz) to indicate an error condition.

The generator 400 also includes a display 408 configured to display information to the clinician or operator. During startup and use, the current status of the generator 400 and energy delivery (treatment) parameters may be displayed on the display 408. During energy delivery, the display 408 may be configured to display remaining treatment time, temperature, impedance, and power information (alphanumerically and/or graphically). For example, graphical representations of power vs. time and impedance vs. time may be displayed. In one implementation, the display may comprise a color, active matrix display. The generator 400 further includes a start/pause button 410 configured to be pressed by an operator to initiate and stop energy delivery. Similar to the indicator light 406 surrounding the instrument connection port 405, a second indicator light 412 may surround the start/pause button 410. The second indicator light 412 may also comprise a circular LED indicator light. The second indicator light 412 may be configured to continuously illuminate in a solid color (e.g., white, blue, green) when the generator 400 is powered on and ready to initiate energy delivery. The indicator light 412 may flash at a first pulsing rate (e.g., 1 Hz) to prompt a clinician to press the start/pause button 410 to initiate energy delivery. The indicator light 412 may flash at a second pulsing rate different than (e.g., faster than) the first pulsing rate (e.g., 2 Hz, 3 Hz, 4 Hz) when energy delivery has been paused or stopped. The generator 400 may also be configured to output audible alerts indicative of the different operating conditions (e.g., to coincide with the output of the indicator lights 406, 412.

The generator 400 may also include a power button 414 configured to power on and off the generator 400, a standby power indicator light 416 configured to illuminate (e.g., in solid green color) when an AC power switch (not shown) of the generator 400 is switched on, an RF active indicator light 417 configured to illuminate (e.g., in solid blue color) during RF energy delivery, and a system fault indicator light 418 configured to illuminate (e.g., in solid red color) during a system fault condition. The generator 400 may also include user input buttons 420 configured to facilitate navigation and selection of options (e.g., menu options, configuration options, acknowledgement requests) that appear on the display 408 (e.g., arrow buttons to toggle up and down between options and an "enter" button for user selection of a desired option).

Access to Locations Outside Vertebral Body

For access to locations outside bone (e.g., extraosseous locations, such as outside a vertebral body), visualization or imaging modalities and techniques may be used to facilitate targeting. For example, a foramen of a vertebral body (e.g., basivertebral foramen) may be located using MRI guidance provided by an external MR imaging system, CT guidance provided by an external tomography imaging system, fluoroscopic guidance using an external X-ray imaging system, and/or an endoscope inserted laparoscopically. Once the foramen is located, therapy (e.g., heat or energy delivery, chemoablative agent delivery, cryotherapy, brachytherapy, and/or mechanical severing) may be applied to the foramen sufficient to modulate (e.g., ablate, denervate, stimulate) any nerves entering through the foramen. For example, an endoscope may be used to locate the foramen under direct visualization and then the basivertebral nerve may be mechanically transected near the foramen. In some implementations, an intervertebral disc and vertebral body may be denervated by treating (e.g., ablating) a sinuvertebral nerve prior to the sinuvertebral nerve branching into the basivertebral nerve that enters the basivertebral foramen of the vertebral body. Because vertebral endplates are cartilaginous, radiation or high-intensity focused ultrasound energy may be applied to vertebral endplates from a location external to a subject's body altogether to denervate nerves in the vertebral endplates.

Target Identification and Patient Screening

In accordance with several implementations, target, or candidate, vertebrae for treatment can be identified prior to treatment. The target, or candidate, vertebrae may be identified based on identification of various types of, or factors associated with, endplate degeneration and/or defects (e.g., focal defects, erosive defects, rim defects, corner defects, all of which may be considered pre-Modic change characteristics). For example, one or more imaging modalities (e.g., MRI, CT, X-ray, fluoroscopic imaging) may be used to determine whether a vertebral body or vertebral endplate exhibits active Modic characteristics or "pre-Modic change" characteristics (e.g., characteristics likely to result in Modic changes, such as Type 1 Modic changes that include findings of inflammation and edema or type 2 Modic changes that include changes in bone marrow (e.g., fibrosis) and increased visceral fat content). For example, images obtained via MRI (e.g., IDEAL MRI) may be used to identify (e.g., via application of one or more filters) initial indications or precursors of edema or inflammation at a vertebral endplate prior to a formal characterization or diagnosis as a Type 1 Modic change. Examples of pre-Modic change characteristics could include mechanical characteristics (e.g., loss of soft nuclear material in an adjacent intervertebral disc of the vertebral body, reduced disc height, reduced hydrostatic pressure, microfractures, focal endplate defects, erosive endplate defects, rim endplate defects, corner endplate defects, osteitis, spondylodiscitis, Schmorl's nodes) or bacterial characteristics (e.g., detection of bacteria that have entered an intervertebral disc adjacent to a vertebral body, a disc herniation or annulus tear which may have allowed bacteria to enter the intervertebral disc, inflammation or new capilarisation that may be caused by bacteria) or other pathogenetic mechanisms that provide initial indications or precursors of potential Modic changes or vertebral endplate degeneration or defects.

Accordingly, vertebral bodies may be identified as target candidates for treatment before Modic changes occur (or before painful symptoms manifest themselves to the patient) so that the patients can be proactively treated to prevent, or reduce the likelihood of, chronic low back pain before it occurs. In this manner, the patients will not have to suffer from debilitating lower back pain for a period of time prior to treatment. Modic changes may or may not be correlated with endplate defects and may or may not be used in candidate selection or screening. In accordance with several embodiments, Modic changes are not evaluated and only vertebral endplate degeneration and/or defects (e.g., pre-Modic change characteristics prior to onset or prior to the ability to identify Modic changes) are identified. Rostral and/or caudal endplates may be evaluated for pre-Modic changes (e.g., endplate defects that manifest before Modic changes that may affect subchondral and vertebral bone marrow adjacent to a vertebral body endplate).

In some implementations, a level of biomarker(s) (e.g., substance P, cytokines, high-sensitivity C-reactive protein, or other compounds associated with inflammatory processes and/or pain and/or that correlate with pathophysiological processes associated with vertebral endplate degeneration or defects (e.g., pre-Modic changes) or Modic changes such as disc resorption, Type III and Type IV collagen degradation and formation, or bone marrow fibrosis) may be obtained from a patient (e.g., through a blood draw (e.g., blood serum) or through a sample of cerebrospinal fluid) to determine whether the patient is a candidate for basivertebral nerve ablation treatment (e.g., whether they have one or more candidate vertebral bodies exhibiting factors or symptoms associated with endplate degeneration or defects (e.g., pre-Modic change characteristics)). Cytokine biomarker samples (e.g., pro-angiogenic serum cytokines such as vascular endothelial growth factor (VEGF)-C, VEGF-D, tyrosine-protein kinase receptor 2, VEGF receptor 1, intercellular adhesion molecule 1, vascular cell adhesion molecule 1) may be obtained from multiple different discs or vertebral bodies or foramina of the patient and compared with each other in order to determine the vertebral bodies to target for treatment. Other biomarkers may be assessed as well, such as neo-epitopes of type III and type IV pro-collagen (e.g., PRO-C3, PRO-C4) and type III and type IV collagen degradation neo-epitopes (e.g., C3M, C4M).

In some implementations, samples are obtained over a period of time and compared to determine changes in levels over time. For example, biomarkers may be measured weekly, bi-monthly, monthly, every 3 months, or every 6 months for a period of time and compared to analyze trends or changes over time. If significant changes are noted between the biomarker levels (e.g., changes indicative of endplate degeneration or defects (e.g., pre-Modic change characteristics) or Modic changes, as described above), treatment may be recommended and performed to prevent or treat back pain. Biomarker levels (e.g., substance P, cytokine protein levels, PRO-C3, PRO-C4, C3M, C4M levels) may be measured using various in vivo or in vitro kits, systems, and techniques (e.g., radio-immunoassay kits/methods, enzyme-linked immunosorbent assay kits, immunohistochemistry techniques, array-based systems, bioassay kits, in vivo injection of an anticytokine immunoglobulin, multiplexed fluorescent microsphere immune-assays, homogeneous time-resolved fluorescence assays, bead-based techniques, interferometers, flow cytometry, etc.). Cytokine proteins may be measured directly or indirectly, such as by measuring mRNA transcripts.

The identification of pre-Modic change characteristics may involve determining a quantitative or qualitative endplate score based on severity, extent, and/or quantity of the identified pre-Modic change characteristics (e.g., vertebral endplate defects) and vertebrae having a quantitative endplate score above a threshold may be deemed as potential candidates for treatment (e.g., basivertebral nerve ablation). The pre-Modic change characteristics may be combined with age, gender, body mass index, bone mineral density measurements, back pain history, and/or other known risk factors for vertebral endplate degeneration or defects (such as smoking, occupational or recreational physical demands or situations) in identifying candidate patients and/or candidate vertebral bodies for treatment (e.g., basivertebral nerve ablation).

Lesion Shaping and Formation

Shaping

In some implementations, a target treatment region within a vertebral body may be clarified using pre-operative imaging (e.g., using bilateral fluoroscopy images or both anterior-posterior and lateral fluoroscopy images) of the vertebral body. The target treatment region may be identified as where a tip of a channeling stylet transects a basivertebral foramen (based on the images). In some implementations, an ideal target treatment region may be located at or about 1 cm from a posterior wall of the vertebral body (e.g., between 10 mm and 11 mm, between 10.5 mm and 11.5 mm, 10 mm, 10.5 mm, 11 mm, 11.5 mm). For certain vertebral body levels, it may be desirable to target an edge of a safety boundary.

In accordance with several implementations, lesion zones, or ablation zones, may advantageously be preferentially shaped to provide sufficient coverage to ablate a basivertebral nerve or other intraosseous nerve but not permanently ablate or damage surrounding or adjacent tissue, thereby minimizing extent of injury or damage. The shape of the lesion zone may be preferentially shaped by providing specific energy treatment algorithms or recipes. For example, a certain amount of power may be applied to heat a target treatment zone to within a certain temperature range for a period of time within a certain time range sufficient to form a lesion zone that ablates a targeted nerve within bone (e.g., basivertebral nerve) but limits the size of the lesion zone to isolate the nerve (e.g., a focused or targeted lesion zone).

In implementations involving radiofrequency energy delivery devices, multiple different sized electrodes may be included along the device and/or the layout of the electrodes may be varied to increase a diameter and/or length (e.g., major diameter along a long axis of the zone and/or minor diameter along a short axis of the zone) or otherwise adjust a shape of a lesion zone. The frequency applied to the electrodes, the power applied to the electrodes, the target temperature, cooling of the electrodes, duration of treatment, and/or the length or diameter of the electrodes may be varied to vary an overall diameter or shape of a lesion. Pulsing of the applied power may also be used to change lesion shape. Power output may be adjusted based on real-time temperature measurements obtained from one or more temperature sensors positioned within and/or along the treatment device or in separate temperature probes inserted within the target treatment zone. The treatment device may also be moved (e.g., rotated and/or translated) at various times during the treatment procedure to affect lesion shape. In other words, the lesion shape may be controlled by rotational attributes. In some implementations, shaping of lesions is effected by controlling an amount of electrode surface area that is exposed (e.g., masking of electrodes to control delivery of energy). In accordance with several implementations, a thermal treatment dose (e.g., using a cumulative equivalent minutes (CEM) 43 degrees Celsius model) is between 200 and 300 CEM (e.g., between 200 and 240 CEM, between 230 CEM and 260 CEM, between 235 CEM and 245 CEM, between 240 CEM and 280 CEM, between 260 CEM and 300 CEM) or greater than a predetermined threshold (e.g., greater than 240 CEM).

In some implementations, a heating, or lesion, zone is established and controlled within a vertebral body so as not to heat any portion of the vertebral body within 1 cm of the posterior wall (e.g., posterior-most border) of the vertebral body. In some implementations, the targeted heating zone is maintained to a region that is between about 10% and about 80%, between about 5% and about 70%, between about 10% and about 65%, between about 20% and about 60%, between about 30% and about 55%, or overlapping ranges thereof, of the distance from the posterior wall to the anterior wall of the vertebral body. The heating zone may be specifically designed and configured to encompass a terminus of a basivertebral nerve or other intraosseous nerve (or of a basivertebral foramen). The terminus may be located approximately mid-body in the vertebral body (e.g., approximately 30%-50% across the sagittal vertebral body width). In various implementations, the heating zone may range from 8 mm to 20 mm (e.g., 8 to 10 mm, 10 to 12 mm, 11 to 13 mm, 12 to 14 mm, 13 to 15 mm, 14 to 20 mm, overlapping ranges thereof, or any value within the recited ranges) in maximum dimension (e.g., largest diameter).

In accordance with several embodiments, a desired target treatment location or region of a vertebral body may be any location at which 75% of the basivertebral nerve branches are sufficiently denervated (e.g., ablated) by applying a thermal treatment dose (e.g., using a cumulative equivalent minutes (CEM) 43 degrees Celsius model) of between 200 and 300 CEM (e.g., between 200 and 240 CEM, between 230 CEM and 260 CEM, between 235 CEM and 245 CEM, between 240 CEM and 280 CEM, between 260 CEM and 300 CEM) or greater than a predetermined threshold (e.g., greater than 240 CEM). In some embodiments, the desired target treatment location or region of a vertebral body is a location that is no more anterior than a location corresponding to 25% arborization of nerve branches of the basivertebral nerve from the exit point at the basivertebral foramen. Arborization may be defined by its ordinary meaning in a medical dictionary and may mean branching off of nerve branches from a main origin nerve (e.g., terminus or entry/exit point of a basivertebral nerve in a vertebral body). 25% arborization may mean that 25% of the total nerve branches within a particular vertebral body have branched off from a main origin nerve. In some embodiments, the desired target treatment location comprises a geometric center or midpoint of the vertebral body. The treatment (e.g., basivertebral nerve ablation) may be performed within multiple different vertebral bodies simultaneously or sequentially using the same parameters. The vertebral bodies may be adjacent or spaced-apart vertebral bodies of the same spine level or a different spine level (e.g., sacral, lumbar, thoracic, cervical).

In accordance with several embodiments, a thermal treatment dose (e.g., using a cumulative equivalent minutes (CEM) 43 degrees Celsius model) of between 200 and 300 CEM (e.g., between 200 and 240 CEM, between 230 CEM and 260 CEM, between 235 CEM and 245 CEM, between 240 CEM and 280 CEM, between 260 CEM and 300 CEM) or greater than a predetermined threshold (e.g., greater than 240 CEM) to form a lesion of a smallest volume that still achieves denervation (e.g., ablation) of 75% of the nerve branches of a basivertebral nerve within a vertebral body. For example, the lesion zone may form a 1 cm diameter sphere that may be elongated or adjusted so as to achieve the 75% denervation depending on the vertebral body characteristics (e.g., level, bone mass density, etc.). A major axis may be between 10 mm and 30 mm (e.g., between 10 mm and 20 mm, between 10 mm and 15 mm, between 15 mm and 25 mm, between 10 mm and 25 mm, between 15 mm and 30 mm, overlapping ranges thereof or any value within the recited ranges) and a minor axis may be between 5 mm and 20 mm (e.g., between 5 mm and 10 mm, between 5 mm and 15 mm, between 8 mm and 15 mm, between 10 mm and 15 mm, between 15 mm and 20 mm, overlapping ranges thereof, or any value within the recited ranges). A major axis length to minor axis length ratio may be between 1:1 and 5:1 (e.g., between 1:1 and 2.5:1, between 1:1 and 2:1, between 1:1 and 3:1, between 1.5:1 and 3:1, between 2:1 and 4:1, overlapping ranges thereof, or any value within the recited ranges, such as 1.2:1, 1.8:1, 1.5:1, 2:1, 2.5:1, 3:1, 3.5:1, 4:1, 4.5:1, or 5:1).

Figure 5B:
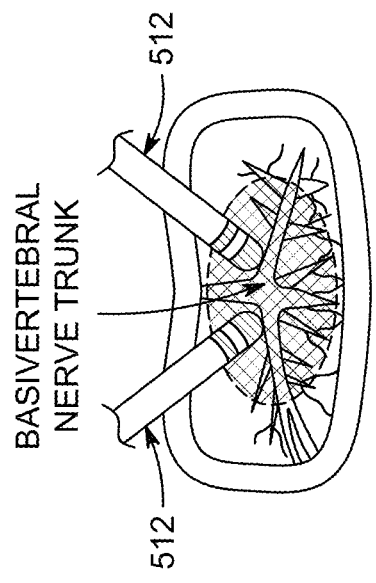
FIG. 5A-5D illustrate example lesion shapes configured to be formed to ablate intraosseous nerves within bone (e.g., vertebral body).
Figure 5D:
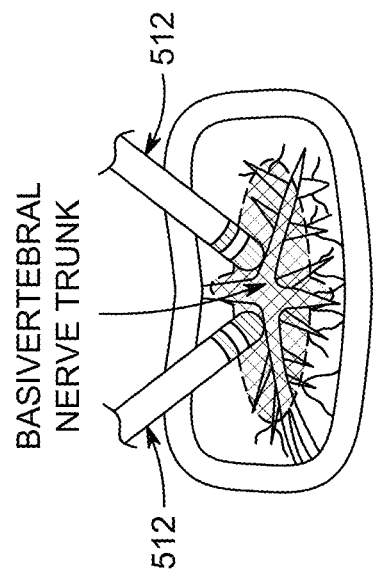
Figure 5A:
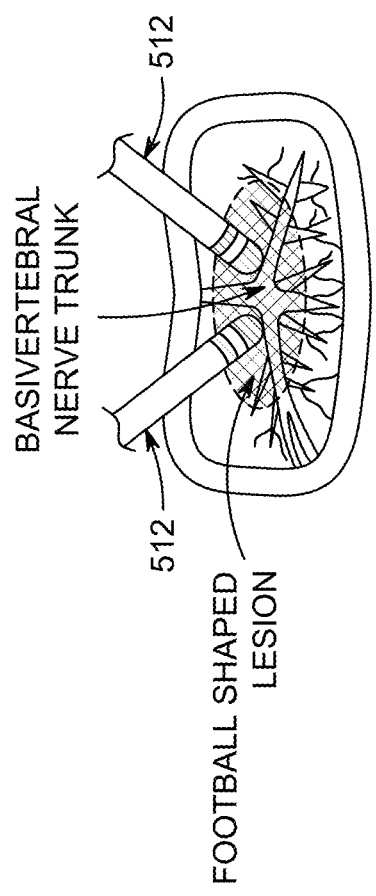
Figure 5C:
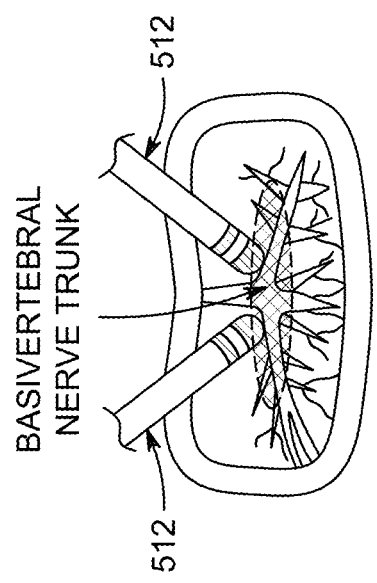

The various treatment parameters described herein may be adjusted to effect a desired lesion shape. FIGS. 5A-5D Illustrate various lesion shapes that may be generated by one or more treatment devices 712. For example, as shown in FIG. 5A, a desired lesion shape may be football-shaped or elliptical-shaped to obtain more anterior-posterior coverage. In some implementations, medial-lateral coverage could be sacrificed to obtain more anterior-posterior coverage. The desired maximum length (dimension of longer axis) and width (dimension of shorter axis) of the football-shaped lesion may be, for example, 30 mm×10 mm, 25 mm×10 mm, 20 mm×10 mm, 30 mm×15 mm, 25 mm×15 mm. In some implementations, the football-shaped lesion has a maximum length to maximum width ratio of about 1.8:1, 1.5:1, 2:1, 2.5:1, 3:1, 3.5:1, 4:1, 4.5:1, or 5:1. The lesion shape may be oval, elliptical (FIG. 5B), cigar-shaped or disc-shaped (FIG. 5C), UFO-shaped (FIG. 5D), rectangular, X-shaped, cross-shaped, or amorphous in various embodiments.

Impedance may be monitored during energy delivery and if impedance is deemed to be outside of a safety threshold range, the energy delivery may be automatically terminated or an alert may be generated so as to prevent, or reduce the likelihood of occurrence of, charring. High impedance measurements may be triggered by increased blood flow in or near the treatment region, thereby resulting in undesired stoppages or interruptions in treatment even though these high impedance measurements do not present safety risks. In accordance with several implementations involving radiofrequency energy delivery devices, detection of regions of high blood flow in or near the target treatment region may be performed in order to position the electrodes in a location that does not have high blood flow in order to avoid these undesired interruptions in energy delivery once energy delivery is initiated. In addition, blood flow may be detected and/or monitored during the treatment procedure and adjustments may be made to the energy delivery algorithm so as not to terminate or interrupt energy delivery when the "false positive" high impedance measurements are obtained as a result of increased blood flow. Multiple thermocouples may be positioned along a length of a treatment probe to steer the treatment probe toward or away from locations of high blood flow.

For implementations involving two treatment probes, each treatment probe can include two or more electrodes and voltage differentials may be applied between different pairs of electrodes on the two probes to adjust the shape of the lesion. The paired electrodes may vary or be toggled such that different pair combinations of electrodes are formed for various durations of time in a predetermined pattern or based on feedback from one or more sensors. The pairs of electrodes may include two electrodes on the same probe and/or two electrodes on different probes. In one implementation, a voltage differential may be applied between electrodes of the same probes for a certain duration and then the voltage differential may be applied between electrode "pairs" disposed on different probes for a certain duration. The durations may be the same or different, depending on the shape of the lesion desired. As an example of an implementation involving use of two probes each having two electrodes, a distal electrode of a first probe may be paired with a distal electrode of a second probe and a proximal electrode of the first probe may be paired with a proximal electrode of the second probe for a first duration of time. Then, the distal electrode of the first probe may be paired with the proximal electrode of the second probe and the distal electrode of the second probe may be paired with the proximal electrode of the first probe for a second duration of time. This pattern may be repeated multiple times over a total treatment duration. The energy delivery devices (e.g., probes) may be connected to a single energy source (e.g., generator) or separate energy sources (e.g., generators).

The durations may vary as desired and/or required (e.g., 20 seconds to 60 seconds, 30 seconds to 90 seconds, 45 seconds to 90 seconds, 1 minute to 2 minutes, 90 seconds to 3 minutes, 2 minutes to 4 minutes, 3 minutes to 5 minutes, 4 minutes to 6 minutes, 6 minutes to 15 minutes, overlapping ranges thereof, or any value within the recited ranges). The corresponding pairs of electrodes may be switched or toggled as many times as desired to form different lesion patters and to adjust overall lesion shape.

Use of two devices or probes may advantageously form synergistic lesions that provide greater surface area or coverage (or the same amount of coverage or treatment efficacy but in a more efficient manner) than could be achieved by independent lesions formed by the separate devices or probes or by a single probe that is moved to different locations. In accordance with several embodiments, the use of two probes and switching patterns of energy delivery between pairs of electrodes may advantageously allow for replenishment of blood in the target treatment region to reduce impedance stoppages.

Figure 6:
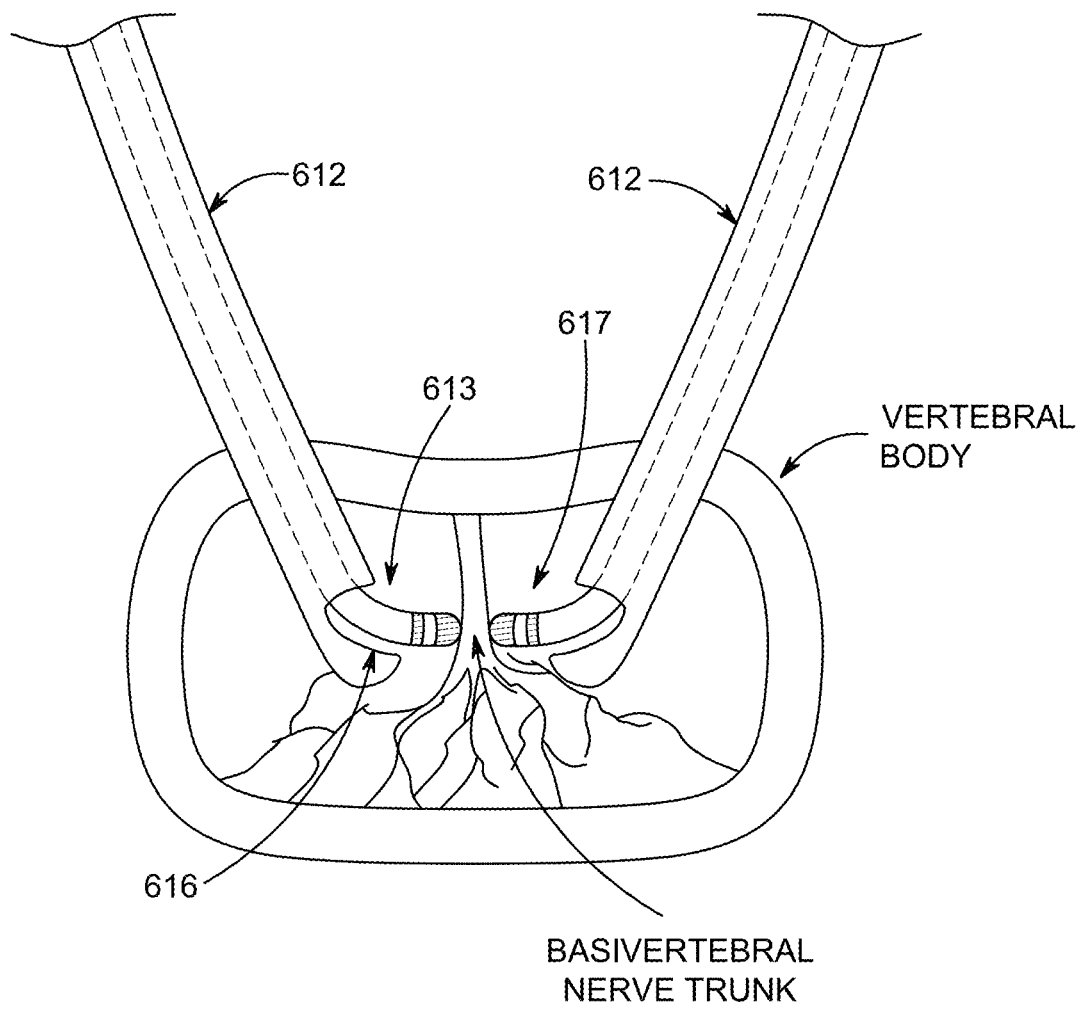
FIG. 6 illustrates an example of a system including two probes and two introducer assemblies configured to facilitate formation of a desired lesion.

With reference to FIG. 6, in implementations involving two treatment devices or probes, the access tools may include two cannulas or introducers 612 each having a radial, or lateral side, window 613 at its distal end and a curved or angled ramp 616 to guide a treatment probe 617 (e.g., treatment device 312) inserted therethrough in a curved or angled direction upon exiting the radial window 613. The windows 613 of the two introducers 612 may be positioned to face toward each other so that the treatment devices or probes 617 curve out of the radial windows 613 toward each other to more effectively control lesion formation and shape as opposed to two probes simply being inserted straight in to the vertebral body (e.g., through separate pedicles). In some implementations, the windows 613 of the introducers/cannulas 612 are visible under fluoroscopy or CT imaging so as to facilitate positioning within a vertebral body or other bone. The introducers 612 may be inserted in combination with an introducer stylet transpedicularly or extrapedicularly into the vertebral body. The introducer stylets may then be removed and the treatment devices or probes 617 then inserted. In some implementations, the introducers 612 have a sharp distal tip and introducer stylets are not required. In some implementations, initial paths are created through the cortical shell of the vertebral body by a separate access instrument and then the introducers 612 are introduced into the vertebral body.

Nerve detection and/or monitoring techniques may be performed during insertion of access tools or treatment devices to increase efficacy and/or targeting. Determined distances between the treatment device and target nerves may be used to adjust treatment parameters to increase efficacy of the treatment. For example, if it is determined from the techniques that a treatment device is in contact with a nerve or within a certain threshold distance from the nerve, ablation time duration may be decreased. However, if it is determined from the nerve detection and/or monitoring techniques that the treatment device (e.g., energy delivery device) is greater than a threshold distance away from the nerve, the ablation time duration may not change or may be increased. The distance between (or contact between) the treatment device and the target nerve may be monitored intra-procedurally and parameters may be adjusted in real time.

The nerve detection techniques may be performed by a laparoscopic device (e.g., catheter or probe with one or multiple stimulation and/or sensory electrodes). The device may be manually controlled or robotically controlled (e.g., using a robotic system such as the robotic system described in connection with FIG. 7). The device may be in electrical communication with an analyzer unit programmed to analyze signals from the device to determine the proximity of the device to the nerve. The analyzer unit may be coupled to an output device (such as a speaker or visual display with a graphical user interface) that is configured to output a quantitative or qualitative output indicative of proximity. The qualitative output may comprise a change in intensity, frequency, volume, or sound of an audible output or a change in color corresponding to distance on a visual display. The quantitative output may comprise actual numeric values of distances displayed on a display screen (e.g., display 408 of generator 400).

Lesion Formation Assessment

Lesion assessment may be performed in real-time during treatment to provide confirmation of treatment or other feedback to a clinician performing the treatment. For example, real-time input of lesion characteristics or lesion formation (e.g., size, temperature, tissue viability, nerve conduction) may be monitored to assure coverage and/or efficacy. Such techniques may advantageously provide intra-operative, real-time confirmation of ablation. Lesion characteristics may be obtained from a variety of sensors (e.g., temperature sensors, impedance sensors) and/or from intra-procedural images.

In some implementations, infrared sensing techniques may be performed to confirm that the treatment device is in a desired treatment location within the vertebral body or other bone and providing sufficient coverage to effect ablation of the basivertebral nerve or tumor without over-extending the coverage. For example, the lesion may be thermally mapped using multiple thermocouples (e.g., two, three, four, five, six, or more than six) positioned at different locations within the vertebral body or other bone and calculations using bioheat transfer equations may be performed by a computer or processor to transform the measurements obtained from the multiple thermocouples into a graphical visualization of the lesion shape or zone in real time (e.g., thermal map). The graphical visualization, or thermal map, may be generated and displayed on a graphical user interface of a display device (e.g., display 608 of generator 600). Different colors may be used to represent different temperature ranges. The treatment procedure may be continued until the lesion reaches a certain desired size or shape as determined from the graphical visualization. The graphical visualization may be sufficiently sized such that it can be overlaid on top of actual anatomical images of the vertebral body so as to facilitate determination of proper lesion formation sufficient to ablate the basivertebral nerve within the vertebral body.

In some implementations, heat markers (e.g., temperature-dependent indicators) may be added to the target treatment zone that under MR or CT imaging manifest in a different way so that a clinician can visualize the lesion growing in real time. For example, once a particular temperature has been reached and maintained for an amount of time sufficient to ensure ablation, the heat marker may appear differently under imaging.

In other implementations, an ultrasound balloon catheter (e.g., having a sensor/emitter combination) may be inserted through one of the pedicles (e.g., on a contralateral side) to map water density changes during ablation, which would be indicative of ablation, edema, etc.

In some implementations, a high-frequency emitter and multiple thermocouples may be used to generate a radar map of bone that can be displayed on a display device (e.g., of the radiofrequency generator). In some implementations, a closed loop system may be employed in which a robotic controller is actively moving a device that changes configuration (e.g., based on artificial intelligence feedback). For example, a probe may be driven to a preselected target using imaging and live feedback.

In accordance with several implementations, biomarkers may be used to confirm treatment efficacy (e.g., whether the procedure resulted in effective ablation of a basivertebral nerve within a vertebral body or an intraosseous nerve within another bone and achieved a desirable therapeutic response). Biomarkers can include anatomical, physiological, biochemical, molecular parameters or imaging features that can be used to confirm treatment efficacy. Biomarkers can be detected and measured by a variety of methods, including but not limited to, physical examination, laboratory assays (such as blood samples), and medical imaging. Biomarkers may be obtained via biological tissue sampling or in a minimally invasive manner (e.g., from blood, saliva, cerebrospinal fluid, or urine). Tissue imaging may also be used to detect and measure biomarkers. Biomarker levels (e.g., substance P or cytokine or heat shock protein levels) may be measured using various in vivo or in vitro (ex vivo) kits, systems, and techniques (e.g., radio-immunoassay kits/methods, enzyme-linked immunosorbent assay kits, immunohistochemistry techniques, array-based systems, bioassay kits, in vivo injection of an anticytokine immunoglobulin, multiplexed fluorescent microsphere immune-assays, homogeneous time-resolved fluorescence assays, bead-based techniques, interferometers, flow cytometry, etc.). Cytokine proteins may be measured directly or indirectly, such as by measuring mRNA transcripts.

The measurement of biomarker levels can utilize one or more capture or detection agents that specifically bind to the biomarker, such as a labeled antibody to bind and detect a biomarker. In some implementations, measurement of biomarkers may utilize a detection agent that has a functional interaction with the biomarker. In other implementations, measurement of biomarkers may be carried out using imaging/spectroscopy techniques that allow biomarkers levels to be assessed in a non-invasive manner or by tissue sampling. Capture or detection agents may be used. In some implementations, binding of a biomarker to a capture agent and/or interaction of the biomarker with a detection agent results in a quantitative, or detectable, signal. The signal may include, for example, a colorimetric, fluorescent, heat, energy, or electric signal. The detectable, quantitative signal may be transmitted to an external output or monitoring device. In some implementations, binding of a biomarker to a capture agent results in a signal that can be transmitted to an external monitoring device. For example, binding of a biomarker to a capture or detection agent may be detected using a high sensitivity fluorescence technique such as a resonance energy transfer method (e.g., Forster resonance energy transfer, bioluminescence resonance energy transfer, or surface plasmon resonance energy transfer).

In various implementations, the measurement of pre- and post-treatment biomarker levels may be carried out using the same device that is used to carry out the treatment (e.g., ablation, denervation) or a component attached to the treatment device. Alternatively, biomarker level or activity may be carried out using a separate device from the treatment device. The separate biomarker assessment device may be inserted through the same introducer as the treatment device or a separate introducer.

Biomarkers may include genetic markers, products of gene expression, autoantibodies, cytokine/growth factors, proteins or enzymes (such as heat shock proteins), and/or acute phase reactants. Biomarkers may include compounds correlated to back pain, such as inflammatory cytokines, Interleukin-1-beta (IL-1-beta), interleukin-1-alpha (IL-1-alpha), interleukin-6 (IL-6), IL-8, IL-10, IL-12, tumor necrosis factor-alpha (TNF-alpha), granulocyte-macrophage colony stimulating factor (GM-CSF), interferon gamma (INF-gamma), and prostaglandin E2 (PGE2). Biomarkers may also be indicative of presence of tumor cells or tissue if tumor tissue is being targeted by the treatment. Biomarkers may be found in blood serum/plasma, urine, synovial fluid, tissue biopsy, foramina, intervertebral discs, cerebrospinal fluid, or cells from blood, fluid, lymph node, and/or tissue.

One or more samples, images, and/or measurements may be obtained from a patient prior to treatment and after treatment and the presence of one or more biomarkers in the pre-treatment and post-treatment samples may be compared to confirm treatment efficacy. The comparison may involve comparison of levels or activity of the biomarkers within the samples. For example, there may be a burst or spike in biomarker concentration following ablation of the basivertebral nerve trunk or branches thereof that can be detected or measured within a collected biological sample.

As another example, the change in the level or activity of the biomarker(s) may be an indirect response to ablation of the basivertebral nerve trunk or branches thereof (e.g., an inflammatory or anti-inflammatory protein, such as a cytokine protein, a heat shock protein, or a stress response protein that is triggered in response to ablative energy being applied to the target treatment region or a non-protein biomarker associated with nervous activity, such as catecholamines, neurotransmitters, norepinephrine levels, neuropeptide Y levels, epinephrine levels, and/or dopamine levels). The post-treatment samples may be obtained immediately following treatment (e.g., within seconds after treatment, within about 15 minutes following treatment, or within about 30 minutes following treatment) and/or may be obtained after a more significant amount of time following treatment (e.g., 24 hours after treatment, 3 days after treatment, 1 week after treatment, 2 weeks after treatment, 1 month after treatment, 3 months after treatment, 6 months after treatment).

Brain imaging or monitoring of brain activity (e.g., electroencephalography, magnetoencephalography) may also be used to confirm efficacy of treatment. The brain imaging or monitoring may be used to determine perception of pain by the patient. Such imaging and/or temperature and/or impedance measurements may also be used in combination with, or as an alternative to, biomarkers to assess lesion formation or confirmation of denervation. Various inputs (e.g., biomarker activity or levels, physiological parameter measurements indicative of neuronal activity, temperature measurements, impedance measurements, and/or images), may be combined (e.g., weighted combinations) to generate a quantitative pain score that can be used to confirm pain relief (as an adjunct or as an alternative to subjective pain relief confirmation). The pain score may be generated using an automated algorithm executed by a processor of a pain analyzer system. The pain analyzer system may receive input from various sensors, imaging devices, and/or the like and the input may be weighted and/or processed by one or more circuits or processing modules of the pain analyzer system to generate the quantitative pain score. The quantitative pain score may be output on a display (e.g., of a generator).

Robotically-Assisted Access and/or Treatment

Figure 7:
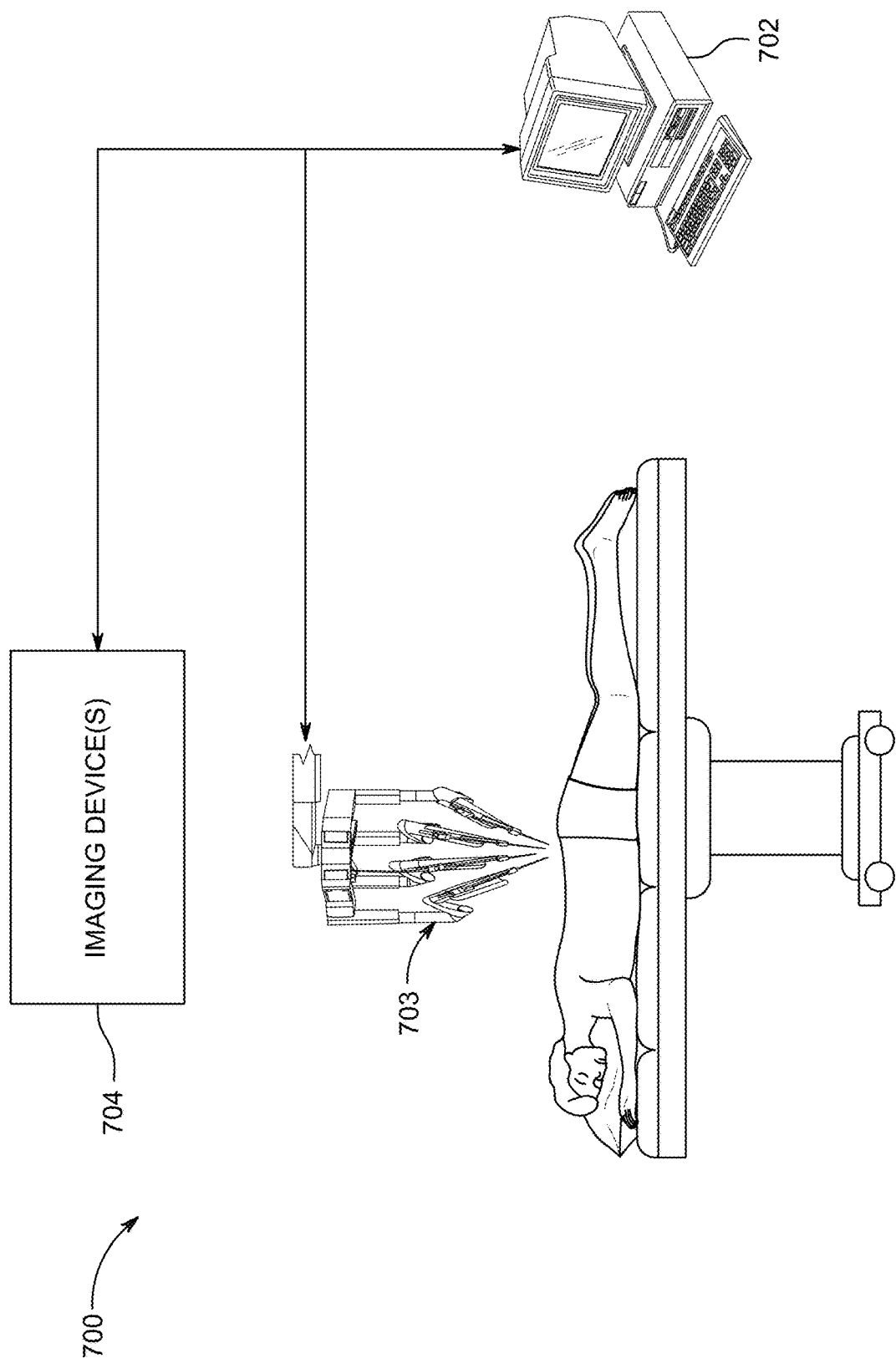
FIG. 7 illustrates a schematic block diagram of a robotically-enabled system.

Access to and/or treatment within or adjacent bones (e.g., vertebral bodies) may be facilitated by the use of robotic navigation systems or robotically-controlled devices (e.g., computer-aided or computer-assisted systems or devices). For example, robotics may be used to facilitate or assist in positioning, targeting, deployment (e.g., hammering) so as to avoid over-insertion that might cause injury or damage, and/or to facilitate nerve sensing. FIG. 7 schematically illustrates an example of a robotically-enabled system 700. The robotic system 700 may be a robotic control, surgical, and/or navigation system capable of performing a variety of medical and/or diagnostic procedures and/or providing guidance and enhanced imaging to a clinician. The robotic system 700 may be a robotic assisted spinal surgery system, or a spinal robotics system.

The robotic system 700 may include an operator workstation or control console 702 from which a clinician can control movement of one or more robotic arms 703 to provide improved ease of use and fine control of movement. The workstation or control console 702 may include a computer-based control system that stores and is configured to execute (e.g., using one or more processors) program instructions stored on a non-transitory computer-readable storage medium (e.g., solid state storage drive, magnetic storage drive, other memory).

The robotic arms 703 may be configured to move with six or more degrees of freedom and to support or carry the access tools, treatment devices, and/or diagnostic devices. The robotic arms 703 may be coupled to a support system and controlled by one or more instrument drive systems that are in turn controlled by the control console 702. The instrument drive systems may include electro-mechanical components and mechanisms (e.g., gears, pulleys, joints, hydraulics, wires, etc.) configured to actuate and move the robotic arms 703.

The robotic system 700 may also include one or more imaging devices 704 (cameras, endoscopes, laparoscopes, ultrasound imaging modality, fluoroscopic imaging modality, MR imaging modality, and/or the like). The imaging devices 704 may be supported or carried by one or more of the robotic arms 703. The imaging devices 704 may be components of an imaging system that facilitates 360-degree scanning of a patient. The imaging devices 704 may include stereotactic cameras and/or electromagnetic field sensors. In some implementations, the imaging devices 704 of the robotic system 700 reduce an amount of patient exposure to radiation. The imaging devices 704 may be calibrated to patient anatomy or using reference pins or trackers positioned at one or more locations of the patient's body by a registration, or localization, system. The registration system may include multiple computing devices (e.g., processors and computer-readable memory for storing instructions to be executed by the processor(s)). The registration may involve identification of natural landmarks of one or more vertebrae (e.g., using a pointer device or the registration system).

The imaging system may be configured to communicate with software (e.g., running on the operator workstation or control console 702 or the registration system) that is configured to generate a real-time 3D map that may be registered with the robotic arms 703 or instruments carried by the robotic arms 703. The software may include surgery planning software configured to plan, based on pre-operative images (e.g., obtained via CT, MRI, fluoroscopy, or other imaging modalities) a desired trajectory for access to a target treatment location within a vertebral body or other bone. However, pre-operative planning may not be used in some implementations and navigation may be performed intraoperatively. The software may include navigation software configured to control the robotic arms 703 and provide feedback regarding navigation (e.g., trajectory and positioning information) to an operator at the operator workstation or on a separate display device. A computing device of the control console 702 is configured to direct movement of the robotic arms 703 based on instructions executed by the computing device (either via inputs (e.g., joystick controls) from a clinician or via automated programs and artificial intelligence algorithms stored in memory). The computing device includes one or more specialized processors. The robotic system 700 may be used to carry out any of the methods of access, diagnosis, or treatment described herein while providing controlled movements to reduce likelihood of injury caused by manual operator error or error in judgment.

In some implementations, the robotic system 700 includes a closed-loop system that alters trajectory of access tools or treatment devices based on feedback (e.g., artificial intelligence). The neuromodulation may also be robotically implemented based on intelligent (e.g., artificial intelligence) feedback. The robotic system 700 may include a machine-driven navigation system deploying an energy source towards a target within a vertebral body to be treated. Detection and monitoring of the energy source's proximity to the target may be provided by the one or more imaging devices. The robotic system 700 can independently modify the trajectory in response to imaging or other registration modalities. Modification of the trajectory may be via change in the configuration of a driving system (e.g., robotic arms 703) and/or by change of the configuration of the energy delivery device or assembly. Modification of trajectory may be automatic (e.g., closed-loop) or based on a feedback mechanism to an operator (e.g., open-loop). The open-loop mode may include boundary conditions (e.g., haptic conditions) or not. The detection and monitoring functions may rely on pre-operative and/or intra-operative data. Registration and targeting may be a priori or interactive.

CONCLUSION

In some implementations, the system comprises various features that are present as single features (as opposed to multiple features). For example, in one embodiment, the system includes a single radiofrequency generator, a single introducer cannula with a single stylet, a single radiofrequency energy delivery device or probe, and a single bipolar pair of electrodes. A single thermocouple (or other means for measuring temperature) may also be included. Multiple features or components are provided in alternate embodiments.

In some implementations, the system comprises one or more of the following: means for tissue modulation (e.g., an ablation or other type of modulation catheter or delivery device), means for monitoring temperature (e.g., thermocouple, thermistor, infrared sensor), means for imaging (e.g., MRI, CT, fluoroscopy), means for accessing (e.g., introducer assembly, curved cannulas, drills, curettes), etc.

Although certain embodiments and examples have been described herein, aspects of the methods and devices shown and described in the present disclosure may be differently combined and/or modified to form still further embodiments. Additionally, the methods described herein may be practiced using any device suitable for performing the recited steps. Further, the disclosure (including the figures) herein of any particular feature, aspect, method, property, characteristic, quality, attribute, element, or the like in connection with various embodiments can be used in all other embodiments set forth herein. The section headings used herein are merely provided to enhance readability and are not intended to limit the scope of the embodiments disclosed in a particular section to the features or elements disclosed in that section.

While the embodiments are susceptible to various modifications, and alternative forms, specific examples thereof have been shown in the drawings and are herein described in detail. It should be understood, however, that the embodiments are not to be limited to the particular forms or methods disclosed, but to the contrary, the embodiments are to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "applying thermal energy" include "instructing the applying of thermal energy."

The terms "top," "bottom," "first," "second," "upper," "lower," "height," "width," "length," "end," "side," "horizontal," "vertical," and similar terms may be used herein; it should be understood that these terms have reference only to the structures shown in the figures and are utilized only to facilitate describing embodiments of the disclosure. The terms "proximal" and "distal" are opposite directional terms. For example, the distal end of a device or component is the end of the component that is furthest from the operator during ordinary use. A distal end or tip does not necessarily mean an extreme distal terminus. The proximal end refers to the opposite end, or the end nearest the operator during ordinary use. Various embodiments of the disclosure have been presented in a range format. It should be understood that the description in range format is merely for convenience and brevity and should not be construed as an inflexible limitation on the scope of the invention. The ranges disclosed herein encompass any and all overlap, sub-ranges, and combinations thereof, as well as individual numerical values within that range. For example, description of a range such as from 70 to 115 degrees should be considered to have specifically disclosed subranges such as from 70 to 80 degrees, from 70 to 100 degrees, from 70 to 110 degrees, from 80 to 100 degrees etc., as well as individual numbers within that range, for example, 70, 80, 90, 95, 100, 70.5, 90.5 and any whole and partial increments therebetween. Language such as "up to," "at least," "greater than," "less than," "between," and the like includes the number recited. Numbers preceded by a term such as "about" or "approximately" include the recited numbers. For example, "about 2:1" includes "2:1." For example, the terms "approximately", "about", and "substantially" as used herein represent an amount close to the stated amount that still performs a desired function or achieves a desired result.

What is claimed is:

1. An introducer system adapted to facilitate percutaneous access to a target treatment location within bone, the introducer system comprising:
    an introducer cannula comprising a proximal handle and a distal elongate hypotube extending from the proximal handle; and
    an introducer stylet comprising a proximal handle and a distal elongate shaft extending from the proximal handle,
    wherein the proximal handle of the introducer cannula comprises a central opening in its upper surface that is coupled to a lumen of the distal elongate hypotube to facilitate insertion of the introducer stylet into the central opening and into the distal elongate hypotube,
    wherein the proximal handle of the introducer cannula comprises one or more slots configured to receive at least a portion of the proximal handle of the introducer stylet so as to facilitate engagement and alignment between the introducer stylet and the introducer cannula,
    wherein at least one of the one or more slots is in communication with the central opening of the proximal handle of the introducer cannula,
    wherein the proximal handle of the introducer stylet comprises an anti-rotation tab configured to be received within one of the one or more slots so as to prevent rotation of the introducer stylet within the introducer cannula,
    wherein a distal end of the distal elongate shaft of the introducer stylet comprises a distal cutting tip and a scalloped section proximal to the distal cutting tip so as to provide gaps between an outer diameter of the distal end of the distal elongate shaft and the inner diameter of the introducer cannula, and
    wherein the proximal handle of the introducer stylet further comprises a press button that, when pressed: (a) disengages the anti-rotation tab and allows for rotation of the introducer stylet within the introducer cannula, and (b) allows for removal of the introducer stylet from the introducer cannula.

2. The introducer system of claim 1:
    wherein the press button is integrally coupled to the anti-rotation tab,
    wherein the scalloped section gradually tapers from a full diameter proximal portion to a narrow-most middle portion and then gradually tapers back to a full diameter distal portion, and
    wherein the proximal handle of the introducer cannula comprises a T-shaped design.

3. The introducer system of claim 1, further comprising a curved cannula assembly, the curved cannula assembly comprising:
    a cannula comprising a proximal handle with a curved insertion slot and a distal polymeric tube,
    wherein the distal polymeric tube comprises a curved distal end portion having a preformed curvature but configured to bend when placed under constraint;

a stylet comprising a proximal handle and a distal elongate shaft, wherein the distal elongate shaft comprises:
- a curved distal end portion having a preformed curvature but configured to bend when placed under constraint and
- a distal channeling tip.

4. The introducer system of claim 1, further comprising an introducer drill adapted to be introduced into and through the introducer cannula to form a further path within the bone after removal of the introducer stylet from the introducer cannula.

5. The introducer system of claim 4, wherein the introducer drill comprises a fluted distal portion and a distal drill tip.

6. The introducer system of claim 5, wherein drill flutes of the fluted distal portion taper away from the distal drill tip so as to facilitate bone chip packing within an open volume defined by the drill flutes as bone chips are generated by operation of the introducer drill.

7. The introducer system of claim 1, wherein the scalloped section comprises a plurality of grooves sized to hold bone debris.

8. The introducer system of claim 1, wherein the at least one of the one or more slots is a curved insertion slot.

9. An introducer system adapted to facilitate percutaneous access to a target treatment location within bone, the introducer system comprising:
- an introducer cannula comprising a proximal handle and a distal elongate hypotube extending from the proximal handle; and
- an introducer stylet comprising a proximal handle and a distal elongate shaft extending from the proximal handle,
- wherein the proximal handle of the introducer cannula comprises a central opening in its upper surface that is coupled to a lumen of the distal elongate hypotube to facilitate insertion of the introducer stylet into the central opening and into the distal elongate hypotube,
- wherein the proximal handle of the introducer cannula comprises one or more slots configured to receive at least a portion of the proximal handle of the introducer stylet so as to facilitate engagement and alignment between the introducer stylet and the introducer cannula,
- wherein at least one of the one or more slots is in communication with the central opening of the proximal handle of the introducer cannula,
- wherein the proximal handle of the introducer stylet comprises an anti-rotation tab configured to be received within one of the one or more slots so as to prevent rotation of the introducer stylet within the introducer cannula,
- wherein a distal end of the distal elongate shaft of the introducer stylet comprises a distal cutting tip and a scalloped section proximal to the distal cutting tip so as to provide gaps between an outer diameter of the distal end of the distal elongate shaft and the inner diameter of the introducer cannula.

10. The introducer system of claim 9:
- wherein the scalloped section gradually tapers from a full diameter proximal portion to a narrow-most middle portion and then gradually tapers back to a full diameter distal portion,
- wherein the proximal handle of the introducer stylet comprises a ramp configured to provide a mechanical assist for removal of the introducer stylet from the introducer cannula; and
- wherein the proximal handle of the introducer cannula comprises a T-shaped design.

11. The introducer system of claim 9, wherein the scalloped section gradually tapers from a full diameter proximal portion to a narrow-most middle portion and then gradually tapers back to a full diameter distal portion.

12. The introducer of claim 11, wherein the taper is symmetric.

13. The introducer system of claim 9, wherein the scalloped section comprises multiple scallops sized to hold bone debris.

14. The introducer system of claim 9, wherein the scalloped section comprises a side profile having an hourglass shape.

15. The introducer system of claim 9, wherein the press button is integrally coupled to the anti-rotation tab such that pressing of the press button extends the anti-rotation tab out of a constraint of the one or more slots.

16. The introducer system of claim 9, wherein a length of the distal elongate shaft is between 8 mm and 14 mm.

17. An introducer system adapted to facilitate percutaneous access to a target treatment location within bone, the introducer system comprising:
- an introducer cannula comprising a proximal handle and a distal elongate hypotube extending from the proximal handle; and
- an introducer stylet comprising a proximal handle and a distal elongate shaft extending from the proximal handle,
- wherein the proximal handle of the introducer cannula comprises a central opening in its upper surface that is coupled to a lumen of the distal elongate hypotube to facilitate insertion of the introducer stylet into the central opening and into the distal elongate hypotube,
- wherein the proximal handle of the introducer cannula comprises one or more slots configured to receive at least a portion of the proximal handle of the introducer stylet so as to facilitate engagement and alignment between the introducer stylet and the introducer cannula,
- wherein at least one of the one or more slots is in communication with the central opening of the proximal handle of the introducer cannula, and
- wherein the proximal handle of the introducer stylet comprises an anti-rotation tab configured to be received within one of the one or more slots so as to prevent rotation of the introducer stylet within the introducer cannula.

18. The introducer system of claim 17, wherein the proximal handle of the introducer stylet further comprises a press button that, when pressed: (a) disengages the anti-rotation tab and allows for rotation of the introducer stylet within the introducer cannula, and (b) allows for removal of the introducer stylet from the introducer cannula.

19. The introducer system of claim 17, wherein the press button is integrally coupled to the anti-rotation tab such that pressing of the press button extends the anti-rotation tab out of a constraint of the one or more slots.

20. The introducer system of claim 17, wherein a length of the distal elongate shaft is between 8 mm and 14 mm.

21. The introducer system of claim 17, wherein the proximal handle of the introducer stylet comprises a ramp configured to provide a mechanical assist for removal of the introducer stylet from the introducer cannula.

\* \* \* \* \*

UNITED STATES PATENT AND TRADEMARK OFFICE
CERTIFICATE OF CORRECTION

Page 1 of 3

PATENT NO. : 11,123,103 B2
APPLICATION NO. : 17/138203
DATED : September 21, 2021
INVENTOR(S) : Brian W. Donovan It is certified that error appears in the above-identified patent and that said Letters Patent is hereby corrected as shown below:

On the Title Page

On page 2, in Column 1, item (56), U.S. Patent Documents, Line 7, delete "Corbin et al." and insert --Corgin et al.--.

On page 3, in Column 1, item (56), U.S. Patent Documents, Line 21, delete "Stru et al." and insert --Strul et al.--.

On page 3, in Column 1, item (56), U.S. Patent Documents, Line 25, delete "Bertin et al." and insert --Bettin et al.--.

On page 3, in Column 2, item (56), U.S. Patent Documents, Line 29, delete "MeWha" and insert --McWha--.

On page 3, in Column 2, item (56), U.S. Patent Documents, Line 37, delete "Eggers" and insert --Eggers et al.--.

On page 4, in Column 1, item (56), U.S. Patent Documents, Line 41, delete "Sluitjer et al." and insert --Sluijter et al.--.

On page 4, in Column 2, item (56), U.S. Patent Documents, Line 8, delete "6,253,086" and insert --6,258,086--.

On page 4, in Column 2, item (56), U.S. Patent Documents, Line 12, delete "Sluigter" and insert --Sluijter--.

On page 4, in Column 2, item (56), U.S. Patent Documents, Line 44, delete "Hissang" and insert --Hissong--.

On page 5, in Column 1, item (56), U.S. Patent Documents, Line 18, delete "Thapliyai et al." and Signed and Sealed this
Fifth Day of April, 2022

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 11,123,103 B2 insert --Thapliyal et al.--.

On page 5, in Column 1, item (56), U.S. Patent Documents, Line 38, delete "Relley et al." and insert --Reiley et al.--.

On page 5, in Column 1, item (56), U.S. Patent Documents, Line 58, delete "Woioszko et al." and insert --Woloszko et al.--.

On page 6, in Column 2, item (56), U.S. Patent Documents, Line 38, delete "8,562,593" and insert --8,562,598--.

On page 6, in Column 2, item (56), U.S. Patent Documents, Line 45, delete "8,603,083" and insert --8,603,088--.

On page 7, in Column 2, item (56), U.S. Patent Documents, Line 45, delete "9,331,045" and insert --9,381,045--.

On page 8, in Column 1, item (56), U.S. Patent Documents, Line 9, delete "Bieier" and insert --Bleier--.

On page 8, in Column 1, item (56), U.S. Patent Documents, Line 62, delete "10,232,719" and insert --10,292,719--.

On page 8, in Column 2, item (56), U.S. Patent Documents, Line 54, delete "2002/0193769" and insert --2002/0193789--.

On page 9, in Column 1, item (56), U.S. Patent Documents, Line 45, after "2006/0129101 A1 6/2006 McGuckin" delete "2006/0173670 A1 8/2006 Woloszko et al.".

On page 9, in Column 2, item (56), U.S. Patent Documents, Line 65, delete "2011/0296261" and insert --2011/0295261--.

On page 10, in Column 1, item (56), U.S. Patent Documents, Line 27, delete "Comacchia" and insert --Cornacchia--.

On page 10, in Column 1, item (56), U.S. Patent Documents, Line 44, delete "2014/0283546" and insert --2014/0288546--.

On page 10, in Column 2, item (56), U.S. Patent Documents, Line 51, delete "Shlkhman et al." and insert --Shikhman et al.--.

On page 12, in Column 2, item (56), Other Publications, Line 44, delete "Wiliams" and insert --Williams--.

On page 12, in Column 2, item (56), Other Publications, Line 56, delete "Nikolal," and insert --Nikolai,--.

CERTIFICATE OF CORRECTION (continued)
U.S. Pat. No. 11,123,103 B2

On page 13, in Column 2, item (56), Other Publications, Line 19, delete "Wiliam" and insert --William--.

In the Claims

In Column 44, Line 11 approx., Claim 12, delete "introducer" and insert --introducer system--.